(12) United States Patent
Peled et al.

(10) Patent No.: US 11,648,293 B2
(45) Date of Patent: *May 16, 2023

(54) COMPOSITIONS AND METHODS FOR TREATING CANCER

(71) Applicants: Biokine Therapeutics Ltd., Nes Ziona (IL); BioLineRx Ltd., Modiin (IL)

(72) Inventors: Amnon Peled, Tel-Aviv (IL); Yaron Pereg, Shoham (IL)

(73) Assignees: Biokine Therapeutics Ltd., Nes Ziona (IL); BioLineRx Ltd., ModiIn (IL)

( * ) Notice: Subject to any disclaimer, the term of this patent is extended or adjusted under 35 U.S.C. 154(b) by 330 days.

This patent is subject to a terminal disclaimer.

(21) Appl. No.: 16/866,600

(22) Filed: May 5, 2020

(65) Prior Publication Data

US 2020/0268842 A1  Aug. 27, 2020

Related U.S. Application Data

(63) Continuation of application No. 15/571,505, filed as application No. PCT/IL2016/050764 on Jul. 14, 2016, now Pat. No. 10,682,390.

(60) Provisional application No. 62/291,039, filed on Feb. 4, 2016, provisional application No. 62/291,006, filed on Feb. 4, 2016, provisional application No. 62/259,182, filed on Nov. 24, 2015, provisional application No. 62/193,201, filed on Jul. 16, 2015.

(51) Int. Cl.

| | | |
|---|---|---|
| *A61K 39/00* | (2006.01) |
| *C07K 16/28* | (2006.01) |
| *A61K 38/17* | (2006.01) |
| *A61K 38/04* | (2006.01) |
| *A61K 47/64* | (2017.01) |
| *A61P 35/00* | (2006.01) |
| *A61K 38/10* | (2006.01) |
| *A61K 39/12* | (2006.01) |
| *A61K 39/395* | (2006.01) |
| *C07K 16/30* | (2006.01) |

(52) U.S. Cl.
CPC .......... *A61K 38/1761* (2013.01); *A61K 38/04* (2013.01); *A61K 38/10* (2013.01); *A61K 38/395* (2013.01); *A61K 39/12* (2013.01); *A61K 39/3955* (2013.01); *A61K 47/646* (2017.08); *A61P 35/00* (2018.01); *C07K 16/2818* (2013.01); *C07K 16/2827* (2013.01); *C07K 16/30* (2013.01); *A61K 2039/55522* (2013.01); *C07K 2317/76* (2013.01)

(58) Field of Classification Search
None
See application file for complete search history.

(56) References Cited

U.S. PATENT DOCUMENTS

| | | |
|---|---|---|
| 4,179,337 A | 12/1979 | Davis et al. |
| 4,239,905 A | 12/1980 | Kodama et al. |
| 4,342,828 A | 8/1982 | Takaku et al. |
| 5,206,018 A | 4/1993 | Sehgal et al. |
| 5,250,732 A | 10/1993 | Kogan et al. |
| 5,492,126 A | 2/1996 | Hennige et al. |
| 5,595,756 A | 1/1997 | Bally et al. |
| 6,128,522 A | 10/2000 | Acker et al. |
| 6,294,459 B1 | 9/2001 | Yin et al. |
| 6,365,583 B1 | 4/2002 | MacFarland et al. |
| 6,576,875 B1 | 6/2003 | Kleffner et al. |
| 6,747,036 B2 | 6/2004 | Gourdeau et al. |
| 6,875,738 B1 | 4/2005 | Clark-Lewis et al. |
| 6,946,445 B1 | 9/2005 | Clark-Lewis et al. |
| 7,138,488 B2 | 11/2006 | Fujii |
| 7,169,750 B2 | 1/2007 | Bridger et al. |
| 7,291,631 B2 | 11/2007 | Bridger et al. |
| 7,419,667 B2 | 9/2008 | Hatake et al. |
| 7,423,007 B2 | 9/2008 | Fujii et al. |
| 7,595,298 B2 | 9/2009 | Fujii |
| 7,630,750 B2 | 12/2009 | Liang et al. |
| 8,017,585 B2 | 9/2011 | Fujii et al. |
| 8,357,690 B2 | 1/2013 | Armstrong et al. |
| 8,410,059 B2 | 4/2013 | Fujii et al. |
| 8,455,450 B2 | 6/2013 | Peled et al. |
| 10,682,390 B2 | 6/2020 | Peled et al. |

(Continued)

FOREIGN PATENT DOCUMENTS

| | | |
|---|---|---|
| CA | 1297007 | 3/1992 |
| CN | 102421899 | 4/2012 |

(Continued)

OTHER PUBLICATIONS

Final Official Action dated Nov. 30, 2020 from the US Patent and Trademark Office Re. U.S. Appl. No. 15/570,389. (35 pages).
Official Action dated Jul. 5, 2022 from US Patent and Trademark Office Re. U.S. Appl. No. 16/866,592. (102 pages).
Notice of Reason for Rejection dated Nov. 4, 2020 From the Japan Patent Office Re. Application No. 2017-563950 and Its Translation Into English. (9 Pages).
Final Official Action dated Oct. 9, 2020 from the US Patent and Trademark Office Re. U.S. Appl. No. 14/771,513. (73 pages).

(Continued)

*Primary Examiner* — Michail A Belyavskyi

(57) ABSTRACT

Use of a CXCR4 antagonistic peptide and an immune-checkpoint regulator in the treatment of cancer is provided. Accordingly there is provided a method of treating cancer in a subject in need thereof, the method comprising administering to the subject a therapeutically effective amount of a peptide having an amino acid sequence as set forth in SEQ ID NO: 1 or an analog or derivative thereof; and a therapeutically effective amount of a PD1 antagonist, a PDL-1 antagonist, a CTLA-4 antagonist, a LAG-3 antagonist, a TIM-3 antagonist, a KIR antagonist, an IDO antagonist, an OX40 agonist, a CD137 agonist, a CD27 agonist, a CD40 agonist, a GITR agonist, a CD28 agonist or an ICOS agonist, thereby treating the cancer in the subject. Also provided are pharmaceutical compositions and articles of manufacture.

4 Claims, No Drawings

Specification includes a Sequence Listing.

(56) References Cited

U.S. PATENT DOCUMENTS

| | | |
|---|---|---|
| 10,786,547 B2 | 9/2020 | Peled et al. |
| 2002/0156034 A1 | 10/2002 | Tudan et al. |
| 2002/0159996 A1 | 10/2002 | Hariharan et al. |
| 2004/0116655 A1 | 6/2004 | Fujii |
| 2004/0197305 A1 | 10/2004 | Garzino-Demo et al. |
| 2004/0209921 A1 | 10/2004 | Bridger et al. |
| 2004/0241169 A1 | 12/2004 | Lowy et al. |
| 2005/0002939 A1 | 1/2005 | Zlotnik et al. |
| 2005/0043367 A1 | 2/2005 | Bridger et al. |
| 2005/0265969 A1 | 12/2005 | Clark-Lewis et al. |
| 2006/0008465 A1 | 1/2006 | Steinaa et al. |
| 2006/0035829 A1 | 2/2006 | Bridger et al. |
| 2006/0079492 A1 | 4/2006 | Ahlem et al. |
| 2006/0264378 A1 | 11/2006 | Fujii et al. |
| 2006/0264605 A1 | 11/2006 | Fujii |
| 2007/0119969 A1 | 5/2007 | Collins, Jr. et al. |
| 2007/0129760 A1 | 6/2007 | Demarais et al. |
| 2007/0167459 A1 | 7/2007 | Habashita et al. |
| 2008/0233053 A1 | 9/2008 | Gross et al. |
| 2009/0181897 A1 | 7/2009 | Fujii et al. |
| 2010/0143334 A1 | 6/2010 | Peled et al. |
| 2010/0166715 A1 | 7/2010 | Peled et al. |
| 2010/0184694 A1 | 7/2010 | Peled et al. |
| 2010/0222256 A1 | 9/2010 | Fujii |
| 2011/0269686 A1 | 11/2011 | Fujii et al. |
| 2012/0082687 A1 | 4/2012 | Yeung et al. |
| 2012/0094907 A1 | 4/2012 | Abraham et al. |
| 2012/0207748 A1 | 8/2012 | Peled et al. |
| 2013/0303460 A1 | 11/2013 | Peled |
| 2014/0030211 A1 | 1/2014 | Peled et al. |
| 2014/0147411 A1 | 5/2014 | Pollack et al. |
| 2014/0322208 A1 | 10/2014 | Kuhne et al. |
| 2015/0125549 A1 | 5/2015 | Peled et al. |
| 2016/0082071 A1 | 3/2016 | Peled et al. |
| 2016/0243187 A1 | 8/2016 | Peled et al. |
| 2018/0140660 A1 | 5/2018 | Peled et al. |
| 2018/0140670 A1 | 5/2018 | Peled et al. |
| 2018/0142211 A1 | 5/2018 | Peled et al. |
| 2018/0161366 A1 | 6/2018 | Peled et al. |
| 2018/0311308 A1 | 11/2018 | Peled et al. |
| 2018/0344801 A1 | 12/2018 | Peled et al. |
| 2019/0038703 A1 | 2/2019 | Peled et al. |
| 2019/0046602 A1 | 2/2019 | Pereg et al. |
| 2020/0268840 A1 | 8/2020 | Peled et al. |
| 2020/0268841 A1 | 8/2020 | Peled et al. |
| 2020/0268843 A1 | 8/2020 | Peled et al. |
| 2020/0268844 A1 | 8/2020 | Peled et al. |
| 2020/0268845 A1 | 8/2020 | Peled et al. |
| 2020/0268846 A1 | 8/2020 | Peled et al. |
| 2020/0276267 A1 | 9/2020 | Peled et al. |
| 2020/0297802 A1 | 9/2020 | Peled et al. |
| 2020/0297803 A1 | 9/2020 | Peled et al. |
| 2020/0297804 A1 | 9/2020 | Peled et al. |
| 2020/0297805 A1 | 9/2020 | Peled et al. |
| 2020/0297806 A1 | 9/2020 | Peled et al. |
| 2020/0297807 A1 | 9/2020 | Peled et al. |
| 2020/0297808 A1 | 9/2020 | Peled et al. |
| 2020/0297809 A1 | 9/2020 | Peled et al. |
| 2020/0297810 A1 | 9/2020 | Peled et al. |
| 2020/0297811 A1 | 9/2020 | Peled et al. |
| 2020/0297812 A1 | 9/2020 | Peled et al. |
| 2020/0390855 A1 | 12/2020 | Peled et al. |
| 2022/0010016 A1 | 1/2022 | Vainstein-Haras et al. |

FOREIGN PATENT DOCUMENTS

| | | |
|---|---|---|
| CN | 105163749 | 12/2015 |
| EP | 0243153 | 10/1987 |
| EP | 0396158 | 11/1990 |
| EP | 0215126 | 7/1991 |
| EP | 0220520 | 9/1991 |
| EP | 0459516 | 12/1991 |
| EP | 0459795 | 12/1991 |
| EP | 0231819 | 4/1992 |
| EP | 0355811 | 12/1993 |
| EP | 0373679 | 6/1994 |
| EP | 0331186 | 8/1994 |
| EP | 0344796 | 9/1994 |
| EP | 0263490 | 1/1995 |
| EP | 0230980 | 3/1996 |
| EP | 0401384 | 3/1996 |
| EP | 0272703 | 10/1997 |
| EP | 0370205 | 7/1998 |
| EP | 0459630 | 8/1998 |
| EP | 0217404 | 1/1999 |
| EP | 0237545 | 8/1999 |
| EP | 0169566 | 7/2000 |
| EP | 0335423 | 3/2003 |
| EP | 1323730 | 7/2003 |
| EP | 0473268 | 10/2003 |
| EP | 1541585 | 6/2005 |
| EP | 2058395 | 5/2009 |
| JP | 2001-523958 | 11/2001 |
| JP | 2001-526689 | 12/2001 |
| JP | 2002-506830 | 3/2002 |
| JP | 2002-247843 | 8/2002 |
| JP | 2003-532683 | 11/2003 |
| JP | 2004-107333 | 4/2004 |
| JP | 2007-502330 | 2/2007 |
| JP | 6294459 | 3/2018 |
| KR | 10-2015-0135432 | 12/2015 |
| WO | WO 91/07988 | 6/1991 |
| WO | WO 93/15211 | 8/1993 |
| WO | WO 95/10534 | 4/1995 |
| WO | WO 98/42752 | 10/1998 |
| WO | WO 98/52598 | 11/1998 |
| WO | WO 99/47158 | 9/1999 |
| WO | WO 00/06086 | 2/2000 |
| WO | WO 00/09152 | 2/2000 |
| WO | WO 01/38352 | 5/2001 |
| WO | WO 01/64716 | 9/2001 |
| WO | WO 01/85196 | 11/2001 |
| WO | WO 02/20561 | 3/2002 |
| WO | WO 03/072599 | 9/2003 |
| WO | WO 2004/020462 | 3/2004 |
| WO | WO 2004/024178 | 3/2004 |
| WO | WO 2004/087068 | 10/2004 |
| WO | WO 2006/126188 | 11/2006 |
| WO | WO 2007/022523 | 2/2007 |
| WO | WO 2007/067280 | 6/2007 |
| WO | WO 2007/146432 | 12/2007 |
| WO | WO 2008/017025 | 2/2008 |
| WO | WO 2008/075369 | 6/2008 |
| WO | WO 2008/075370 | 6/2008 |
| WO | WO 2008/075371 | 6/2008 |
| WO | WO 2009/091826 | 7/2009 |
| WO | WO 2010/146578 | 12/2010 |
| WO | WO 2010/146584 | 12/2010 |
| WO | WO 2011/069121 | 6/2011 |
| WO | WO 2012/095849 | 7/2012 |
| WO | WO 2013/160895 | 10/2013 |
| WO | WO 2014/155376 | 10/2014 |
| WO | WO 2015/016718 | 2/2015 |
| WO | WO 2015/019284 | 2/2015 |
| WO | WO 2015/063768 | 5/2015 |
| WO | WO 2015/069770 | 5/2015 |
| WO | WO 2016/185475 | 11/2016 |
| WO | WO 2016/185476 | 11/2016 |
| WO | WO 2017/009842 | 1/2017 |
| WO | WO 2017/009843 | 1/2017 |
| WO | WO 2017/145161 | 8/2017 |

OTHER PUBLICATIONS

Biology for Life "Interpreting Error Bars", Retrieved from the Internet, Aug. 27, 2018, 4 pages.

Curtis et al. "High-Dose Cytosine Arabinoside in the Treatment of Acute Myelogenous Leukemia: Contributions to Outcome of Clinical and Laboratory Attributes", Journal of Clinical Oncology 5 (4): 532-543, 1987.

Ellison et al. "Arabinosyl Cytosine: A Useful Agent in the Treatment of Acute Leukemia in Adults", Blood—the Journal of Hematology 32 (4): 507-523, 1968.

(56) References Cited

OTHER PUBLICATIONS

Niitsu et al. "Induction of Differentiation of Acute Promyelocytic Leukemia Cells by a Cytidine Deaminase-resistant Analogue of 1-B-D-Arabinofuranosylcytosine, 1-(2-Deoxy-2-methylene~-B-D-erythro-pentofuranosyl)cytidine", Cancer Research 61: 178-185, 2001.
Quentmeier et al. "FLT3 Mutations in Acute Myeloid Leukemia Cell Lines", Leukemia 17: 120-124, 2003.
Weisberg et al. "Drug Resistance in Mutant FL T3-Positive AML", Oncogene 29: 5120-5134, 2010.
Advisory Action Before the Filing of an Appeal Brief dated May 3, 2017 From the US Patent and Trademark Office Re. U.S. Appl. No. 14/771,513. (8 pages).
Advisory Action Before the Filing of an Appeal Brief dated Aug. 5, 2014 From the US Patent and Trademark Office Re. U.S. Appl. No. 13/378,061.
Advisory Action Before the Filing of an Appeal Brief dated Nov. 16, 2012 From the US Patent and Trademark Office Re. U.S. Appl. No. 12/520,699.
Advisory Action Before the Filing of an Appeal Brief dated Nov. 22, 2019 From the US Patent and Trademark Office Re. U.S. Appl. No. 16/078,696. (21 pages).
Applicant-Initiated Interview Summary dated Nov. 4, 2019 From the US Patent and Trademark Office Re. U.S. Appl. No. 16/078,696. (3 Pages).
Applicant-Initiated Interview Summary dated Oct. 12, 2018 From the US Patent and Trademark Office Re. U.S. Appl. No. 14/771,513. (7 pages).
Applicant-Initiated Interview Summary dated Oct. 12, 2018 From the US Patent and Trademark Office Re. U.S. Appl. No. 16/049,898. (7 pages).
Communication Pursuant to Article 94(3) EPC dated Aug. 2, 2016 From the European Patent Office Re. Application No. 14717212.6.
Communication Pursuant to Article 94(3) EPC dated May 3, 2013 From the European Patent Office Re. Application No. 10176632.7.
Communication Pursuant to Article 94(3) EPC dated May 3, 2019 From the European Patent Office Re. Application No. 15169576.4. (6 Pages).
Communication Pursuant to Article 94(3) EPC dated Mar. 4, 2015 From the European Patent Office Re. Application No. 12702887.6.
Communication Pursuant to Article 94(3) EPC dated Oct. 4, 2010 From the European Patent Office Re. Application No. 03791288.8.
Communication Pursuant to Article 94(3) EPC dated Oct. 4, 2013 From the European Patent Office Re. Application No. 07849622.1.
Communication Pursuant to Article 94(3) EPC dated Oct. 4, 2013 From the European Patent Office Re. Application No. 07849623.9.
Communication Pursuant to Article 94(3) EPC dated Feb. 5, 2018 From the European Patent Office Re. Application No. 14802211.4. (6 Pages).
Communication Pursuant to Article 94(3) EPC dated Nov. 6, 2015 From the European Patent Office Re. Application No. 12702887.6.
Communication Pursuant to Article 94(3) EPC dated Apr. 9, 2008 From the European Patent Office Re. Application No. 03791288.8.
Communication Pursuant to Article 94(3) EPC dated Sep. 11, 2013 From the European Patent Office Re. Application No. 10176632.7.
Communication Pursuant to Article 94(3) EPC dated Oct. 12, 2016 From the European Patent Office Re. Application No. 13727657.2.
Communication Pursuant to Article 94(3) EPC dated Dec. 15, 2008 From the European Patent Office Re. Application No. 03791288.8.
Communication Pursuant to Article 94(3) EPC dated Sep. 15, 2009 From the European Patent Office Re. Application No. 03791288.8.
Communication Pursuant to Article 94(3) EPC dated Dec. 21, 2017 From the European Patent Office Re. Application No. 15169576.4. (11 Pages).
Communication Pursuant to Article 94(3) EPC dated Mar. 26, 2020 From the European Patent Office Re. Application No. 16745185.5. (3 Pages).
Communication Pursuant to Article 94(3) EPC, Invitation to Remedy Deficiencies in Subsequently Filed Documents (Rule 50(1) EPC / Rule 11.14 PCT) dated Jul. 10, 2018 From the European Patent Office Re. Application No. 15169576.4. (68 Pages).
Communication Pursuant to Article 96(2) EPC dated Feb. 6, 2006 From the European Patent Office Re. Application No. 10963414.6.
Communication Pursuant to Article 96(2) EPC dated Mar. 17, 2005 From the European Patent Office Re. Application No. 10963414.6.
Communication Pursuant to Article 96(2) EPC dated Jul. 18, 2006 From the European Patent Office Re. Application No. 10963414.6.
Communication Pursuant to Article 96(2) EPC dated Jul. 26, 2007 From the European Patent Office Re. Application No. 10963414.6.
Communication Relating to the Results of the Partial International Search dated Oct. 31, 2016 From the International Searching Authority Re. Application No. PCT/IL2016/050764. (12 Pages).
Communication Under Rule 164(2)(a) EPC dated Apr. 10, 2019 From the European Patent Office Re. Application No. 16745185.5. (4 Pages).
Completion Requirement Letter dated Oct. 24, 2013 From the Canadian Intellectual Property Office Re. Application No. 2,765,345.
European Search Report and the European Search Opinion dated Aug. 3, 2015 From the European Patent Office Re. Application No. 15166376.2.
European Search Report and the European Search Opinion dated Feb. 3, 2012 From the European Patent Office Re. Application No. 10176632.7.
European Search Report and the European Search Opinion dated Oct. 20, 2015 From the European Patent Office Re. Application No. 15169576.4.
European Search Report and the European Search Opinion dated Oct. 21, 2014 From the European Patent Office Re. Application No. 14153703.5.
Examination Report dated Oct. 1, 2019 From the Australian Government, IP Australia Re. Application No. 2019200329. (3 Pages).
Examination Report dated Dec. 2, 2019 From the Australian Government, IP Australia Re. Application No. 2014343214. (4 Pages).
Examination Report dated Apr. 4, 2019 From the Australian Government, IP Australia Re. Application No. 2017222495.(3 Pages).
Examination Report dated Oct. 11, 2018 From the Australian Government, IP Australia Re. Application No. 2014240733. (5 Pages).
Examination Report dated Aug. 13, 2014 From the Institute Mexicano de la Propiedad Industrial Re. Application No. MX/a/2011/013459 and Its Translation Into English.
Examination Report dated Sep. 14, 2018 From the Institute Mexicano de la Propiedad Industrial, IMPI, Direccion Divisional de Patentes Re. Application No. MX/a/2015/013525 and Its Translation Into English. (5 Pages).
Examination Report dated Apr. 19, 2018 From the Australian Government, IP Australia Re. Application No. 2014240733. (4 Pages).
Examination Report Under Sections 12 & 13 of the Patents Act, 1970 and the Patents Rules, 2003 dated Jan. 10, 2020 From the Government of India, Intellectual Property India, Patents, Designs, Trade Marks, Geographical Indications, the Patent Office Re. Application No. 2777/MUMNP/2015. (6 Pages).
Examination Report Under Sections 12 & 13 of the Patents Act, 1970 and the Patents Rules, 2003 dated Oct. 27, 2017 From the Government of India, Intellectual Property India, Patents, Designs, Trademarks, Geographical Indications Re. Application No. 75/MUMNP/2012. (8 Pages).
Examiner's Answer Dated Feb. 23, 2018 Before the Patent Trial and Appeal Board of the US Patent and Trademark Office Re. U.S. Appl. No. 14/771,513. (31 pages).
Final Official Action dated Apr. 1, 2020 from the US Patent and Trademark Office Re. U.S. Appl. No. 15/571,069. (32 pages).
Grounds of Reasons for Rejection dated Dec. 12, 2018 From the Korean Intellectual Property Office Re. Application No. 10-2018-7027178. (6 Pages).
Grounds of Reasons for Rejection dated Apr. 24, 2019 From the Korean Intellectual Property Office Re. Application No. 10-2018-7027178. (3 Pages).
Hearing Notice Dated Apr. 5, 2018 From the Government of India, Patent Office, Intellectual Property Building Re. Application No. 75/MUMNP/2012. (2 Pages).

(56) References Cited

OTHER PUBLICATIONS

Hearing Notice Dated Jun. 18, 2020 From the Government of India, Intellectual Property India, Patent Office, Intellectual Property Building Re. Application No. 2777/MUMNP/2015. (2 Pages).
International Preliminary Report on Patentability dated Nov. 6, 2014 From the International Bureau of WIPO Re. Application No. PCT/IL2013/050352.
International Preliminary Report on Patentability dated Sep. 7, 2018 From the International Bureau of WIPO Re. Application No. PCT/IL2017/050232. (7 Pages).
International Preliminary Report on Patentability dated Oct. 8, 2015 From the International Bureau of WIPO Re. Application No. PCT/IL2014/050303.
International Preliminary Report on Patentability dated May 12, 2016 From the International Bureau of WIPO Re. Application No. PCT/IL2014/050939.
International Preliminary Report on Patentability dated Jul. 18, 2013 From the International Bureau of WIPO Re. Application No. PCT/IL2012/050008.
International Preliminary Report on Patentability dated Apr. 19, 2002 From the International Preliminary Examining Authority Re. PCT/JP2001/007668.
International Preliminary Report on Patentability dated Aug. 19, 2004 From the International Preliminary Examining Authority Re. Application No. PCT/JP2003/010753.
International Preliminary Report on Patentability dated Jun. 24, 2009 From the International Bureau of WIPO Re. Application No. PCT/IL2007/001596.
International Preliminary Report on Patentability dated Jun. 24, 2009 From the International Bureau of WIPO Re. Application No. PCT/IL2007/001598.
International Preliminary Report on Patentability dated Jan. 25, 2018 From the International Bureau of WIPO Re. Application No. PCT/IL2016/050764. (18 Pages).
International Preliminary Report on Patentability dated Jan. 25, 2018 From the International Bureau of WIPO Re. Application No. PCT/IL2016/050765. (17 Pages).
International Preliminary Report on Patentability dated Dec. 29, 2011 From the International Bureau of WIPO Re. Application No. PCT/IL2010/000466.
International Preliminary Report on Patentability dated Nov. 30, 2017 From the International Bureau of WIPO Re. Application No. PCT/IL2016/050527. (9 Pages).
International Preliminary Report on Patentability dated Nov. 30, 2017 From the International Bureau of WIPO Re. Application No. PCT/IL2016/050529. (9 Pages).
International Search Report and the Written Opinion dated Sep. 2, 2013 From the International Searching Authority Re. Application No. PCT/IL2013/050352.
International Search Report and the Written Opinion dated Feb. 3, 2015 From the International Searching Authority Re. Application No. PCT/IL2014/050939.
International Search Report and the Written Opinion dated May 3, 2017 From the International Searching Authority Re. Application No. PCT/IL2016/050765. (25 Pages).
International Search Report and the Written Opinion dated Jun. 4, 2008 From the International Searching Authority Re. Application No. PCT/IL2007/001598.
International Search Report and the Written Opinion dated Dec. 5, 2008 From the International Searching Authority Re. Application No. PCT/IL2007/001596.
International Search Report and the Written Opinion dated Jan. 11, 2017 From the International Searching Authority Re. Application No. PCT/TL2016/050764. (27 Pages).
International Search Report and the Written Opinion dated Oct. 15, 2010 From the International Searching Authority Re. Application No. PCT/IL2010/000466.
International Search Report and the Written Opinion dated Aug. 16, 2016 From the International Searching Authority Re. Application No. PCT/IL2016/050529.
International Search Report and the Written Opinion dated Jun. 17, 2014 From the International Searching Authority Re. Application No. PCT/IL2014/050303.
International Search Report and the Written Opinion dated Aug. 21, 2016 From the International Searching Authority Re. Application No. PCT/IL2016/050527.
International Search Report and the Written Opinion dated Jun. 24, 2009 From the International Searching Authority Re. Application No. PCT/IL2007/001597.
International Search Report and the Written Opinion dated Jun. 30, 2017 From the International Searching Authority Re. Application No. PCT/IL2017/050232. (12 Pages).
International Search Report and the Written Opinion dated May 30, 2012 From the International Searching Authority Re. Application No. PCT/IL2012/050008.
International Search Report dated Nov. 4, 2003 From the International Searching Authority Re. Application No. PCT/JP2003/010753.
International Search Report dated Dec. 11, 2001 From the International Searching Authority Re. Application No. PCT/JP2001/007668.
Interview Summary dated May 3, 2005 From the US Patent and Trademark Office Re. U.S. Appl. No. 10/363,209.
Interview Summary dated Feb. 21, 2006 From the US Patent and Trademark Office Re. U.S. Appl. No. 10/363,209.
Invitation to Pay Additional Fees and Communication Relating to the Results of the Partial International Search dated Feb. 28, 2017 From the International Searching Authority Re. Application No. PCT/IL2016/050765. (13 Pages).
Notice of Decision to Grant Patent dated Aug. 26, 2019 From the Korean Intellectual Property Office Re. Application No. 10-2018-7027178. (3 Pages).
Notice of Panel Decision From Pre-Appeal Brief Review dated Jul. 14, 2017 From the US Patent and Trademark Office Re. U.S. Appl. No. 14/771,513. (2 Pages).
Notice of Preliminary Rejection dated Oct. 10, 2016 From the Korean Intellectual Property Office Re. Application No. 2012-7000921.
Notice of Reason for Rejection dated Aug. 6, 2019 From the Japan Patent Office Re. Application No. 20184-544337. (3 Pages).
Notice of Reason for Rejection dated Jul. 8, 2014 From the Japanese Patent Office Re. Application No. 2012-515626 and Its Translation Into English.
Notice of Reason for Rejection dated Jun. 11, 2019 From the Japan Patent Office Re. Application No. 20184-544337 and a Summary of the Notice of Reason for Rejection Into English. (5 Pages).
Notice of Reason for Rejection dated Nov. 11, 2014 From the Japanese Patent Office Re. Application No. 2012-515626 and Its Translation Into English.
Notice of Reason for Rejection dated Oct. 24, 2017 From the Japan Patent Office Re. Application No. 2016-503780. (3 Pages).
Notice of Reasons for Rejection dated Feb. 4, 2020 From the Japan Patent Office Re. Application No. 2019-059920 and Its Translation Into English. (8 Pages).
Notice of Reasons for Rejection dated Mar. 17, 2020 From the Japan Patent Office Re. Application No. 2017-563950 and Its Translation Into English. (7 Pages).
Notice of Reasons for Rejection dated Mar. 27, 2018 From the Japan Patent Office Re. Application No. 2016-524577 and Its Translation Into English. (11 Pages).
Notice of Reexamination dated Mar. 11, 2016 From the Patent Reexamination Board of State Intellectual Property Office of the People's Republic of China Re. Application No. 201080035931.5 and Its Translation Into English.
Notice of Refusal dated Jan. 15, 2019 From the Japan Patent Office Re. Application No. 2018-544337. (5 Pages).
Notice of the Reason for Rejection dated Feb. 17, 2019 From the Korean Intellectual Property Office Re. Application No. 2015-7030463 and Its Translation Into English. (5 Pages).
Notice of the Reason for Rejection dated Jun. 22, 2019 From the Korean Intellectual Property Office Re. Application No. 2015-7030463 and Its Summary in English. (8 Pages).

(56) References Cited

OTHER PUBLICATIONS

Notification of Office Action and Search Report dated Nov. 5, 2013 From the State Intellectual Property Office of the People's Republic of China Re. Application No. 201080035931.5 and Its Translation Into English.
Notification of Office Action and Search Report dated Mar. 6, 2013 From the State intellectual Property Office of the People's Republic of China Re. Application No. 201080035931.5 and Its Summary in English.
Notification of Office Action and Search Report dated Jul. 25, 2019 From the State Intellectual Property Office of the People's Republic of China Re. Application No. 201780026678.9. (6 Pages).
Notification of Office Action and Search Report dated Mar. 25, 2019 From the State Intellectual Property Office of the People's Republic of China Re. Application No. 201480071187.2 and Its Translation of Office Action Into English. (14 Pages).
Notification of Office Action and Search Report dated Jun. 27, 2016 From the State Intellectual Property Office of the People's Republic of China Re. Application No. 201480023972.0 and Its Translation of Office Action Into English.
Notification of Office Action dated Mar. 11, 2020 From the State Intellectual Property Office of the People's Republic of China Re. Application No. 201780026678.9 and Its Translation Into English. (6 Pages).
Notification of Office Action dated Dec. 15, 2016 From the State Intellectual Property Office of the People's Republic of China Re. Application No. 201480023972.0. (5 Pages).
Notification of Office Action dated Dec. 25, 2019 From the State Intellectual Property Office of the People's Republic of China Re. Application No. 201480071187.2. (4 Pages).
Notification of Office Action dated Jul. 28, 2017 From the State Intellectual Property Office of the People's Republic of China Re. Application No. 201480023972.0. (4 Pages).
Notification of the Decision of Rejection dated Mar. 31, 2014 From the State Intellectual Property Office of the People's Republic of China Re. Application No. 201080035931.5 and Its Translation Into English.
Office Action dated Apr. 3, 2014 From the Israel Patent Office Re. Application No. 218405 and Its Translation Into English.
Office Action dated May 4, 2010 From the Israel Patent Office Re. Application No. 199468.
Office Action dated May 4, 2010 From the Israel Patent Office Re. Application No. 199469.
Office Action dated Sep. 4, 2011 From the Israel Patent Office Re. Application No. 199468 and Its Translation Into English.
Office Action dated Feb. 7, 2019 From the Israel Patent Office Re. Application No. 244329 and Its Translation Into English. (4 Pages).
Office Action dated Sep. 8, 2015 From the Israel Patent Office Re. Application No. 218405.
Office Action dated Apr. 9, 2014 From the Israel Patent Office Re. Application No. 229151 and Its Translation Into English.
Office Action dated Aug. 12, 2015 From the Israel Patent Office Re. Application No. 199468.
Office Action dated Aug. 13, 2015 From the Israel Patent Office Re. Application No. 199468 and Its Translation Into English.
Office Action dated Aug. 13, 2015 From the Israel Patent Office Re. Application No. 218405 and Its Translation Into English.
Office Action dated Mar. 13, 2013 From the Israel Patent Office Re. Application No. 199468 and Its Translation Into English.
Office Action dated Feb. 15, 2016 From the Israel Patent Office Re. Application No. 240924 and Its Translation Into English.
Office Action dated May 15, 2014 From the Israel Patent Office Re. Application No. 199468 and Its Translation Into English.
Office Action dated May 20, 2013 From the Israel Patent Office Re. Application No. 216912 and Its Translation Into English.
Office Action dated Jun. 22, 2015 From the Israel Patent Office Re. Application No. 229151 and Its Translation Into English.
Office Action dated Feb. 23, 2017 From the Israel Patent Office Re. Application No. 240924 and Its Translation Into English. (4 Pages).
Office Action dated Mar. 27, 2019 From the Israel Patent Office Re. Application No. 261160 and Its Translation Into English. (5 Pages).
Office Action dated Jul. 28, 2013 From the Israel Patent Office Re. Application No. 199469 and Its Translation Into English.
Office Action dated Nov. 29, 2016 From the Israel Patent Office Re. Application No. 199468 and Its Translation Into English. (5 Pages).
Office Action dated Nov. 29, 2016 From the Israel Patent Office Re. Application No. 218405 and its Translation into English. (5 Pages).
Office Action dated Jul. 30, 2014 From the Israel Patent Office Re. Application No. 216912 and Its Translation Into English.
Office Action dated Jun. 30, 2016 From the Israel Patent Office Re. Application No. 229151 and Its Translation Into English.
Office Action dated Oct. 31, 2011 From the Israel Patent Office Re. Application No. 199469 and Its Translation Into English.
Official Action dated Jul. 1, 2010 From the US Patent and Trademark Office Re. U.S. Appl. No. 12/172,007.
Official Action dated Nov. 3, 2005 From the US Patent and Trademark Office Re. U.S. Appl. No. 10/363,209.
Official Action dated May 4, 2012 From the US Patent and Trademark Office Re. U.S. Appl. No. 12/520,699.
Official Action dated Oct. 4, 2018 From the US Patent and Trademark Office Re. U.S. Appl. No. 16/049,898. (31 pages).
Official Action dated Dec. 5, 2016 From the US Patent and Trademark Office Re. U.S. Appl. No. 14/771,513. (36 Pages).
Official Action dated Jul. 5, 2013 From the US Patent and Trademark Office Re. U.S. Appl. No. 12/520,811.
Official Action dated Mar. 5, 2012 From the US Patent and Trademark Office Re. U.S. Appl. No. 12/520,803.
Official Action dated Sep. 5, 2012 From the US Patent and Trademark Office Re. U.S. Appl. No. 12/520,699.
Official Action dated May 6, 2013 From the US Patent and Trademark Office Re. U.S. Appl. No. 13/360,751.
Official Action dated Aug. 7, 2019 From the US Patent and Trademark Office Re. U.S. Appl. No. 16/078,696. (30 pages).
Official Action dated Dec. 7, 2012 From the US Patent and Trademark Office Re. U.S. Appl. No. 12/520,699.
Official Action dated Sep. 8, 2017 From the US Patent and Trademark Office Re. U.S. Appl. No. 15/027,252. (194 pages).
Official Action dated Dec. 9, 2014 From the US Patent and Trademark Office Re. U.S. Appl. No. 13/378,061.
Official Action dated Dec. 9, 2019 From the US Patent and Trademark Office Re. U.S. Appl. No. 15/570,342. (121 pages).
Official Action dated Aug. 10, 2018 From the US Patent and Trademark Office Re. U.S. Appl. No. 14/771,513. (31 pages).
Official Action dated Aug. 10, 2018 From the US Patent and Trademark Office Re. U.S. Appl. No. 16/035,790. (215 pages).
Official Action dated Sep. 10, 2012 From the US Patent and Trademark Office Re. U.S. Appl. No. 12/583,746.
Official Action dated Jul. 11, 2007 From the US Patent and Trademark Office Re. U.S. Appl. No. 10/525,838.
Official Action dated Sep. 12, 2012 From the US Patent and Trademark Office Re. U.S. Appl. No. 12/520,803.
Official Action dated Jul. 14, 2016 From the US Patent and Trademark Office Re. U.S. Appl. No. 14/771,513.
Official Action dated May 14, 2014 From the US Patent and Trademark Office Re. U.S. Appl. No. 13/378,061.
Official Action dated May 14, 2019 From the US Patent and Trademark Office Re. U.S. Appl. No. 16/078,696. (60 Pages).
Official Action dated Jun. 15, 2005 From the US Patent and Trademark Office Re. U.S. Appl. No. 10/363,209.
Official Action dated Sep. 15, 2014 From the US Patent and Trademark Office Re. U.S. Appl. No. 13/889,442.
Official Action dated Dec. 17, 2013 From the US Patent and Trademark Office Re. U.S. Appl. No. 13/378,061.
Official Action dated Dec. 18, 2019 From the US Patent and Trademark Office Re. U.S. Appl. No. 15/571,505. (111 pages).
Official Action dated Jun. 18, 2014 From the US Patent and Trademark Office Re. U.S. Appl. No. 13/978,740.
Official Action dated May 18, 2012 From the US Patent and Trademark Office Re. U.S. Appl. No. 13/178,737.
Official Action dated Sep. 18, 2019 From the US Patent and Trademark Office Re. U.S. Appl. No. 15/571,069. (102 pages).

(56) References Cited

OTHER PUBLICATIONS

Official Action dated Jan. 19, 2018 From the US Patent and Trademark Office Re. U.S. Appl. No. 15/027,252. (64 pages).
Official Action dated Dec. 21, 2015 From the US Patent and Trademark Office Re. U.S. Appl. No. 14/395,842.
Official Action dated Feb. 21, 2019 From the US Patent and Trademark Office Re. U.S. Appl. No. 16/049,898. (97 pages).
Official Action dated Jan. 22, 2016 From the US Patent and Trademark Office Re. U.S. Appl. No. 13/378,061.
Official Action dated Dec. 23, 2019 From the US Patent and Trademark Office Re. U.S. Appl. No. 16/163,605. (121 pages).
Official Action dated Apr. 24, 2013 From the US Patent and Trademark Office Re. U.S. Appl. No. 13/360,751.
Official Action dated Jan. 24, 2011 From the US Patent and Trademark Office Re. U.S. Appl. No. 12/172,007.
Official Action dated Apr. 25, 2019 From the US Patent and Trademark Office Re. U.S. Appl. No. 16/049,898. (45 pages).
Official Action dated Apr. 25, 2019 From the US Patent and Trademark Office Re. U.S. Appl. No. 16/163,605. (102 pages).
Official Action dated Jun. 25, 2012 From the US Patent and Trademark Office Re. U.S. Appl. No. 12/520,811.
Official Action dated Feb. 27, 2015 From the US Patent and Trademark Office Re. U.S. Appl. No. 13/978,740.
Official Action dated Aug. 28, 2008 From the US Patent and Trademark Office Re. U.S. Appl. No. 11/497,225.
Official Action dated Dec. 28, 2011 From the US Patent and Trademark Office Re. U.S. Appl. No. 12/583,746.
Official Action dated Jan. 28, 2020 From the US Patent and Trademark Office Re. U.S. Appl. No. 14/771,513. (101 pages).
Official Action dated May 28, 2015 From the US Patent and Trademark Office Re. U.S. Appl. No. 13/378,061.
Official Action dated Jan. 29, 2013 From the US Patent and Trademark Office Re. U.S. Appl. No. 13/360,751.
Official Action dated Jan. 31, 2013 From the US Patent and Trademark Office Re. U.S. Appl. No. 12/520,811.
Official Action dated Jul. 6, 2020 from the US Patent and Trademark Office Re. U.S. Appl. No. 15/571,069. (10 pages).
Partial European Search Report dated Jun. 4, 2014 From the European Patent Office Re. Application No. 14153703.5.
Patent Examination Report dated Jan. 17, 2019 From the Australian Government, IP Australia Re. Application No. 2017222495.(2 Pages).
Requisition—Sequence Listing dated Jan. 5, 2011 From the Canadian Intellectual Property Office Re. Application No. 2,673,719.
Requisition—Sequence Listing dated May 9, 2013 From the Canadian Intellectual Property Office Re. Application No. 2,673,719.
Requisition by the Examiner dated Dec. 2, 2016 From the Canadian Intellectual Property Office Re. Application No. 2,673,484.
Requisition by the Examiner dated Jul. 4, 2013 From the Canadian Intellectual Property Office Re. Application No. 2,537,158.
Requisition by the Examiner dated Jul. 6, 2012 From the Canadian Intellectual Property Office Re. Application No. 2,421,183.
Requisition by the Examiner dated Jul. 8, 2013 From the Canadian Intellectual Property Office Re. Application No. 2,421,183.
Requisition by the Examiner dated Mar. 8, 2011 From the Canadian Intellectual Property Office Re. Application No. 2,421,183.
Requisition by the Examiner dated Apr. 15, 2015 From the Canadian Intellectual Property Office Re. Application No. 2,673,719.
Requisition by the Examiner dated Jun. 15, 2016 From the Canadian Intellectual Property Office Re. Application No. 2,673,719.
Requisition by the Examiner dated Oct. 17, 2011 From the Canadian Intellectual Property Office Re. Application No. 2,537,158.
Requisition by the Examiner dated Jun. 18, 2013 From the Canadian Intellectual Property Office Re. Application No. 2,673,484.
Requisition by the Examiner dated May 18, 2017 From the Canadian Intellectual Property Office Re. Application No. 2,673,719. (4 Pages).
Requisition by the Examiner dated May 19, 2011 From the Canadian Intellectual Property Office Re. Application No. 2,421,183.
Requisition by the Examiner dated Sep. 22, 2015 From the Canadian Intellectual Property Office Re. Application No. 2,673,484.
Requisition by the Examiner dated Nov. 23, 2018 From the Innovation, Science and Economic Development Canada, Canadian Intellectual Property Office Re. Application No. 3,014,530. (4 Pages).
Requisition by the Examiner dated Aug. 25, 2009 From the Canadian Intellectual Property Office Re. Application No. 2,421,183.
Requisition by the Examiner dated Jun. 25, 2015 From the Canadian Intellectual Property Office Re. Application No. 2,765,345.
Requisition by the Examiner dated Mar. 25, 2019 From the Innovation, Science and Economic Development Canada, Canadian Itnellectual Property Office Re. Application No. 2,906,314. (4 Pages).
Requisition by the Examiner dated May 25, 2010 From the Canadian Intellectual Property Office Re. Application No. 2,537,158.
Requisition by the Examiner dated May 26, 2014 From the Canadian Intellectual Property Office Re. Application No. 2,673,484.
Requisition by the Examiner dated Aug. 29, 2019 From the Innovation, Science and Economic Development Canada, Canadian Intellectual Property Office Re. Application No. 3,014,530. (6 Pages).
Requisition by the Examiner dated Jan. 31, 2019 From the Innovation, Science and Economic Development Canada, Canadian Intellectual Property Office Re. Application No. 3,014,530. (4 Pages).
Restriction Official Action dated Mar. 1, 2012 From the US Patent and Trademark Office Re. U.S. Appl. No. 12/520,699.
Restriction Official Action dated Oct. 3, 2013 From the US Patent and Trademark Office Re. U.S. Appl. No. 13/378,061.
Restriction Official Action dated Feb. 4, 2014 From the US Patent and Trademark Office Re. U.S. Appl. No. 13/978,740.
Restriction Official Action dated Sep. 4, 2019 From the US Patent and Trademark Office Re. U.S. Appl. No. 15/570,342. (7 pages).
Restriction Official Action dated Feb. 6, 2007 From the US Patent and Trademark Office Re. U.S. Appl. No. 10/525,838.
Restriction Official Action dated Feb. 6, 2019 From the US Patent and Trademark Office Re. U.S. Appl. No. 16/078,696. (8 pages).
Restriction Official Action dated Apr. 8, 2008 From the US Patent and Trademark Office Re. U.S. Appl. No. 11/497,225.
Restriction Official Action dated Jul. 9, 2014 From the US Patent and Trademark Office Re. U.S. Appl. No. 13/889,442.
Restriction Official Action dated Jun. 10, 2019 From the US Patent and Trademark Office Re. U.S. Appl. No. 15/571,069. (7 Pages).
Restriction Official Action dated Oct. 10, 2019 From the US Patent and Trademark Office Re. U.S. Appl. No. 15/571,505. (4 Pages).
Restriction Official Action dated Jun. 14, 2017 From the US Patent and Trademark Office Re. U.S. Appl. No. 15/027,252. (14 Pages).
Restriction Official Action dated Sep. 14, 2011 From the US Patent and Trademark Office Re. U.S. Appl. No. 12/583,746.
Restriction Official Action dated Feb. 16, 2012 From the US Patent and Trademark Office Re. U.S. Appl. No. 13/178,737.
Restriction Official Action dated Mar. 18, 2005 From the US Patent and Trademark Office Re. U.S. Appl. No. 10/363,209.
Restriction Official Action dated Mar. 22, 2016 From the US Patent and Trademark Office Re. U.S. Appl. No. 14/771,513.
Restriction Official Action dated Jan. 23, 2019 From the US Patent and Trademark Office Re. U.S. Appl. No. 16/163,605X. (11 pages).
Restriction Official Action dated Mar. 26, 2009 From the US Patent and Trademark Office Re. U.S. Appl. No. 12/172,007.
Restriction Official Action dated Dec. 28, 2011 From the US Patent and Trademark Office Re. U.S. Appl. No. 12/520,803.
Restriction Official Action dated Mar. 28, 2012 From the US Patent and Trademark Office Re. U.S. Appl. No. 12/520,811.
Restriction Official Action dated May 7, 2020 from the US Patent and Trademark Office Re. U.S. Appl. No. 15/570,389. (12 pages).
Summons to Attend Oral Proceedings Pursuant to Rule 115(1) EPC Dated Dec. 9, 2014 From the European Patent Office Re. Application No. 07849622.1.
Summons to Attend Oral Proceedings Pursuant to Rule 115(1) EPC Dated Feb. 12, 2015 From the European Patent Office Re. Application No. 07849622.1.
Supplementary European Search Report and the European Search Opinion dated Jan. 3, 2013 From the European Patent Office Re. Application No. 10789103.8.

(56) References Cited

OTHER PUBLICATIONS

Supplementary European Search Report and the European Search Opinion dated Apr. 11, 2011 From the European Patent Office Re. Application No. 07849622.1.
Supplementary European Search Report and the European Search Opinion dated Sep. 12, 2019 From the European Patent Office Re. Application No. 17755946.5. (8 Pages).
Supplementary European Search Report dated Nov. 19, 2004 From the European Patent Office Re. Application No. 01963414.6.
Supplementary Partial European Search Report dated Nov. 28, 2007 From the European Patent Office Re. Application No. 03791288.8.
Translation Dated Jan. 6, 2020 of Notification of Office Action dated Dec. 25, 2019 From the State Intellectual Property Office of the People's Republic of China Re. Application No. 201480071187.2. (3 Pages).
Translation Dated Jul. 9, 2019 of Notice of the Reason for Rejection dated Jun. 22, 2019 From the Korean Intellectual Property Office Re. Application No. 2015-7030463. (3 Pages).
Translation Dated Mar. 20, 2019 of Notice of Refusal dated Jan. 15, 2019 From the Japan Patent Office Re. Application No. 2018-544337. (7 Pages).
Translation Dated Sep. 24, 2019 of Notice of Reason for Rejection dated Aug. 6, 2019 From the Japan Patent Office Re. Application No. 20184-544337. (2 Pages).
Translation Dated Dec. 27, 2018 of Grounds of Reasons for Rejection dated Dec. 12, 2018 From the Korean Intellectual Property Office Re. Application No. 10-2018-7027178. (7 Pages).
Translation Dated Apr. 30, 2019 of Grounds of Reasons for Rejection dated Apr. 24, 2019 From the Korean intellectual Property Office Re. Application No. 10-2018-7027178. (2 Pages).
Translation of Notice of Preliminary Rejection dated Oct. 10, 2016 From the Korean Intellectual Property Office Re. Application No. 2012-7000921.
Translation of Notice of Reason for Rejection dated Oct. 24, 2017 From the Japan Patent Office Re. Application No. 2016-503780. (3 Pages).
Translation of Notification of Office Action dated Mar. 6, 2013 From the State Intellectual Property Office of the People's Republic of China Re. Application No. 201080035931.5.
Translation of Notification of Office Action dated Aug. 9, 2019 From OA of Jul. 25, 2019 From the State Intellectual Property Office of the People's Republic of China Re. Application No. 201780026678.9. (5 Pages).
Translation of Notification of Office Action dated Dec. 15, 2016 From the State Intellectual Property Office of the People's Republic of China Re. Application No. 201480023972.0. (4 Pages).
Translation of Notification of Office Action dated Jul. 28, 2017 From the State Intellectual Property Office of the People's Republic of China Re. Application No. 201480023972.0. (1 Page).
Translation of Office Action dated Feb. 1, 2013 From the Japanese Patent Office Re. Application No. 2011-060367.
Translation of Office Action dated Aug. 11, 2009 From the Japanese Patent Office Re. Application No. 2003-301176.
Translation of Office Action dated Oct. 19, 2010 From the Japanese Patent Office Re. Application No. 2003-301176.
Translation of Search Report dated Mar. 6, 2013 From the State Intellectual Property Office of the People's Republic of China Re. Application No. 201080035931.5.
AACR "97th Annual Meeting 2006: Publications", AACR, American Association of Cancer Research, Retreived From the Internet, 2006.
Abraham et al. "Enhanced Unique Pattern of Hematopoietic Cell Mobilization Induced by the CXCR4 Antagonist 4F-Benzoyl-TN14003", Stem Cells, XP002629045, 25(9): 2158-2166, May 24, 2007. p. 2159.
Abraham et al. "Sequential Administration of the High Affinity CXCR4 Antagonist BKT140 Promotes Megakaryopoiesis and Platelet Production", British Journal of Haematology, 163: 248-259, Published Online Aug. 1, 2013.
Abraham et al. "The CXCR4 Antagonist 4F-Benzoyl-TN14003 Stimulates the Recovery of the Bone Marrow After Transplantation", Leukemia, 23(8): 1378-1388, Aug. 2009.
Afdhal et al. "Review Article: Pharmacological Approaches for the Treatment of Thrombocytopenia in Patients With Chronic Liver Disease and Hepatitis C Infection", Alimentary Pharmacology & Therapeutics, 26(Suppl. 1): 29-39, Nov. 2007.
Alwan et al. "The Efficacy of Fludarabine, High Dose Cytosine Arabinoside with Granulocyte Colony Stimulating Factor (FLAG) Protocol as Salvage Therapy for Refractory/Relapsed Acute Leukemias in Adult Iraqi Patients", Indian Journal of Hematology and Blood Transfusion, 30(4): 231-235, Published Online Feb. 23, 2013.
American Cancer Society "Typical Treatment of Acute Myeloid Leukemia (Except APL)", retrieved from cancer.org, 8 Pages, Aug. 21, 2018.
Amin et al. "Having a Higher Blast Percentage in Circulation Than Bone Marrow: Clinical Implications in Myelodysplastic Syndrome and Acute Lymphoid and Myeloid Leukemias", Leukemia, 19(19): 1567-1572, Published Online Jul. 28, 2005.
Arakaki et al. "T134, a Small-Molecule CXCR4 Inhibitor, Has No Cross-Drug Resistance With AMD3100, a CXCR4 Antagonist With a Different Structure", Journal of Virology, XP002199036, 73(2): 1719-1723, Feb. 1999.
Arellano et al. "High-Dose Cytarabine Induction Is Well Tolerated and Active in Patients With de Novo Acute Myeloid Leukemia Older Than 60 Years", Cancer, 118(2):428-433, Jan. 15, 2012.
Auerbach et al. "Angiogenesis Assays: Problems, Pitfalls and Potential", Cancer and Metastasis Reviews, 19: 167-172, 2000.
Avniel et al. "Involvement of the CXCL12/CXCR4 Pathway in the Recovery of Skin Following Burns", Journal of Investigative Dermatology, 126(2): 468-476, 2006.
Balkwill "The Significance of Cancer Cell Expression of the Chemokine Receptor CXCR4", Seminars in Cancer Biology, 14: 171-179, 2004.
Basu et al. "Purification of Specific Cell Population by Fluorescence Activated Cell Sorting (FACS)", Journal of Visualized Experiments, 41: 1-4, Jul. 10, 2010.
Beider et al. "CXR4 Antagonist 4F-Benzoyl-TN 14003 Inhibits Leukemia and Multiple Myeloma Tumor Growth", Experimental Hematology, XP028154790, 39(3): 282-292, Published Online Dec. 5, 2010.
Bork "Powers and Pitfalls in Sequence Analysis: The 70% Hurdle", Genome Research, 10: 398-400, 2000.
Borthakur et al. "BL-8040, a Peptide CXCR4 Antagonist, Induces Leukemia Cell Death and Specific Leukemia Cell Mobilization in Relapsed/Refractory Acute Myeloid Leukemia Patients in an Ongoing Phase IIa Clinical Trial", Blood, 124(21): 950, Dec. 4, 2014.
Borthakur et al. "The Peptidic CXCR4 Antagonist, BL-8040, Significantly Reduces Bone Marrow Immature Leukemia Progenitors by Reducing Differentiation, Apoptosis and Mobilization: Results of the Dose Escalation Clinical Trial in Acute Myeloid Leukemia", Blood, XP009512306, 126(23): 2546, Dec. 3, 2015.
Borthakur et al. "The Selective Anito Leukemic Effect of BL-8040, a Peptidic CXCR4 Antagonist, Is Mediated by Induction of Leukemic Blast Mobilization, Differentiation and Apoptosis: Results of Correlative Studies From a Ph2a Trial in Acute Myeloid Leukemia", Blood, 128(22): 2754, Dec. 1, 2016.
Bossi et al. "ImmTAC-Redirected Tumour Cell Killing Induces and Potentiates Antigen Cross-Presentation by Dendritic Cells", Cancer Immunology, Immunotherapy, XP055335144, 63(5): 437-448, Published Online Feb. 15, 2014.
Bowie et al "Deciphering the Message in Protein Sequences: Tolerance to Amino Acid Substitutions", Science, 247(4948): 1306-1310, Mar. 16, 1990.
Braess et al. "Oral Cytarabine Odosfate in Acute Myeloid Leukemia and Non-Hodgkin's Lymphoma Hase 1/11 Studies and Pharmacokinetics" , Leukemia, 12(10):1618-1626, Oct. 1998.
Brenner "Errors in Genome Annotation", Trends in Genetics, TIG, 15(4): 132-133, Apr. 1999.
Broxmeyer et al. "Rapid Mobilization of Murine and Human Hematopoietic Stem and Progenitor Cells With AMD3100, a CXCR4 Antagonist", the Journal of Experimental Medicine, XP009076434, 201(8): 1307-1318, Apr. 18, 2005. p. 1309.

(56) References Cited

OTHER PUBLICATIONS

Buchner et al. "Acute Myeloid Leukemia (AML): Different Treatment Strategies Versus a Common Standard Arm-Combined Prospective Analysis by the German AML Intergroup", Journal of Clinical Oncology, 30(29): 3604-3610, Oct. 10, 2012.
Burger et al. "CXCR4 Chemokine Receptor Antagonists: Perspectives in SCLC", Expert Opinion on Investigational Drugs, XP002711650, 18(4): 481-490, Apr. 2009.
Burger et al. "Potential of CXCR4 Antagonists for the Treatment of Metastatic Lung Cancer", Expert Reviews of Anticancer Therapy, XP009152669, 1(4): 621-630, Apr. 1, 2011.
Burger et al. "Small Peptide Inhibitors of the CXCR4 Chemokine Receptor (CD184) Antagonize the Activation, Migration, and Antiapoptotic Responses of CXCL12 in Chronic Lymphocytic Leukemia B Cells", Blood, XP002629047, 106(5): 1824-1830, Sep. 1, 2005. p. 1824, 1825.
Burgess et al. "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue", The Journal of Cell Biology, 111: 2129-2138, Nov. 1990.
Carlisle et al. "CXCR4 Expression Heterogeneity in Neuroblastoma Cells Due to Ligand-Independent Regulation", Molecular Cancer, 8(126): 1-14, Dec. 22, 2009.
Chen et al. "CXCR4 Inhibition in Tumor Microenvironment Facilitates Anti-Programmed Death Receptor-1 Immunotherapy in Sorafenib-Treated Hepatocellular Carcinoma in Mice", Hepatology, 61: 1591-1602, May 2015.
Cheson et al. "Revised Recommendations of the International Working Group for Diagnosis, Standardization of Response Criteria, Treatment Outcomes, and Reporting Standards for Therapeutic Trials in Acute Myeloid Leukemia," Journal of Clinical Oncology, 21 (24): 4642-4649, 2003.
Cho et al. "Antileukemia Activity of the Novel Peptidic CXCR4 Antagonist LY2510924 as Monotherapy and in Combination with Chemotherapy", Blood, 126(2): 222-232, Published Online Jun. 1, 2015.
Coiffier et al. "Chop Chemotherapy Plus Rituximab Compared With Chop Alone in Elderly Patients With Diffuse Large-B-Cell Lymphoma", The New England Journal of Medicine, XP055117777, 346(4): 235-242, Jan. 24, 2002.
Cytarabine "Cytarabine (Conventional)", Retrieved from drugs.com, 25 Pages, Aug. 6, 2019.
Dar et al. "Chemokine Receptor CXCR4-Dependent Internalization and Resecretion of Functional Chemokine SDF-1 by Bone Marrow Endothelial and Stromal Cells", Nature Immunology, 6(10): 1038-1046, Oct. 2005.
Darash-Yahana et al. "Role of High Expression Levels of CXCR4 in Tumor Growth, Vascularization, and Metastatis", The FASEB Journal, 18: 1240-1242, 2004. p. 1242, Last Para.
Di Cesare et al. "In Vitro Characterization and Inhibition of the CXCR4/CXCL12 Chemokine Axis in Human Uveal Melanoma Cell Lines", Cancer Cell International, XP021036445, 7(17): 1-8, Nov. 14, 2007. Abstract, Last Para, Title, p. 5, Right col., Last Para.
Doerks et al. "Protein Annotation: Detective Work for Function Predicition", Trends in Genetics, 14(6): 248-250, Jun. 1998.
Esler et al. "Renal Sympathetic Denervation in Patients With Treatment-Resistant Hypertension (The Symplicity HTN-2 Trial): A Randomised Controlled Trial", The Lancet, 376: 1903-1909, Published Online Nov. 17, 2010.
Fahham et al. "In Vitro and In Vivo Therapeutic Efficacy of CXCR4 Antagonist BKT140 Against Human Non-Small Cell Lung Cancer", The Journal of Thoracic and Cardiovascular Surgery, XP055076134, 144(5): 1167-1175, Nov. 1, 2012.
Fathi et al. "FLT3 Inhibition as Therapy in Acute Myeloid Leukelnia: A Record of Trials and Tribulations", The Oncologist. 16(8): 1162-1174, Published Online Jul. 17, 2011.
Flomenberg et al. "The Use of AMD3100 Plus G-CSF for Autologous Hematopoietic Progenitor Cell Mobilization Is Superior to G-CSF Alone", Blood, 106(5): 1867-1874, 2005.
Fransen et al. "Suppression of Dualtropic Human Immunodeficiency Virus Type 1 by the CXCR4 Antagonist AMD3100 Is Associated With Efficiency of CXCR4 Use and Baseline Virus Composition", Antimicrobial Agents and Chemotherapy, 52(7): 2608-2615, Apr. 28, 2008.
Fujii et al. "Peptide-Lead CXCR4 Antagonists With High Anti-HIV Activity", Current Opinion in Investigational Drugs, 2(9): 1198-1202, 2001.
Garon et al. "Pembrolizumab for the Treatment of Non-Small-Cell Lung Cancer", The New England Journal of Medicine, XP55306209, 372(21): 2018-2028, May 21, 2015.
Gazitt et al. "Improved Mobilization of Peripheral Blood CD34+ Cells and Dendritic Cells by AMD3100 Plus Granulocyte-Colony-Stimulating Factor in Non-Hodgkin's Lymphoma Patients", Stem Cells and Development, 16(4): 657-666, Aug. 15, 2007. Figs.3, 4.
Ghobrial et al. "Molecular Mechanisms Involved in Homing and Migration of Plasma Cells in Response to CXCR4 Stimulation and Downstream Activation of the P13K Pathway", Database BIOSIS [Online], XP002629050, Retrieved From BIOSIS, Database Accession No. PREV200510270159, Nov. 16, 2004. Abstract.
Ghobrial et al. "Molecular Mechanisms Involved in Homing and Migration of Plasma Cells in Response to CXCR4", Blood, XP002629051, 104(11): 1-33, Apr. 12, 2005.
Gnecchi et al. "Bone Marrow-Derived Mesenchymal Stem Cells: Isolation, Expansion, Characterization, Viral Transduction, and Production of Conditioned Medium", Stem Cells in Regenerative Medicine: Methods and Protocols, 482(Chap.18): 281-294, Published Online Dec. 18, 2008.
Gotoh et al. "Increase of R5 HIV-1 Infection and CCR5 Expression in T Cells Treated With High Concentrations of CXCR4 Antagonists and SDF-1", Journal of Infection and Chemotherapy, 7(1): 28-36, 2001.
Gross et al. "Chemokines in Neuroectodermal Cancers: The Crucial Growth Signal From the Soil", Seminars in Cancer Biology, 19(2): 103-110, Apr. 2009.
Gura "Cancer Models: Systems for Identifying New Drugs Are Often Faulty", Science, 278(5340): 1041-1042, Nov. 7, 1997.
Hatse et al. "CXC-ChemokineReceptor 4 as a Potential New Therapeutic Target for Neuroblastoma and Breast Cancer", International Journal of Cancer, XP001156644, Supplement, 13: 349, Abstract # p. 669, Jul. 2002.
Hendrix et al. "Safety, Pharmacokinetics, and Antiviral Activity of AMD3100, a Selective CXCR4 Receptor Inhibitor, in HIV-1 Infection", Journal of Aquired Immune Deficiency Syndromes, JAIDS, 37(2): 1253-1261, Oct. 1, 2004.
Heredia et al. "Rapamycin Causes Down-Regulation of CCR5 and Accumulation of Anti-HIV Beta-Chemokines: An Approach to Suppress R5 Strains of HIV-1", Proc. Natl. Acad. Sci. USA, PNAS, 100(18): 10411-10416, Sep. 2, 2003.
Hesselgesser et al. "Neuronal Apoptosis Induced by HIV-1 Gp120 and the Chemokine SDF-1Alpha Is Mediated by the Chemokine Receptor CXCR4", Current Biology, 8: 595-598, Apr. 27, 1998.
Hiramatsu et al. "Synthesis of CXCR4 Antagonists, T140 Derivatives With Improved Biostability, and Their SAR Study", Peptide Science, XP009092185, 203: 213-216, 2002. Abstract, Fig.1.
HIV "Report of the Investigation for Development of HIV Medicaments (Year 2000)", p. 16-21, 2001. Japanese Only!
HIV "Strategic Generation of Anti-AIDS Agents Based on HIV Secondary Receptor Antagonists and Modification of the Agents for Pharmaceutical Use", Report of the Investigation for Development of HIV Medicaments (Year 2000), p. 16-21, 2001. English Translation.
Hunter et al. "Dosing Chemotherapy in Obese Patients: Actual Versus Assigned Body Surface Area (BSA)", Cancer Treatment Reviews 35(1): 69-78, 2009.
Jacobi et al. "Impact of CXCR4 Inhibition on FLT3-ITD—Positive Human AML Blasts", Experimental Hematology, XP026913582, 38(3): 180-190, Mar. 1, 2010.
Jain "Barriers to Drug Delivery in Solid Tumors. Many Tumors Resist Full Penetration by Anticancer Agents. Such Resistance May Help Explain Why Drugs That Eradicate Tumor Cells in Laboratory Dishes Often Fail to Eliminate Malignancies in the Body", Scientific American, p. 58-65, Jul. 1994.

(56) References Cited

OTHER PUBLICATIONS

Juarez et al. "Effects of Inhibitors of the Chemokine Receptor CXCR4 on Acute Lymphoblastic Leukemia Cells In Vitro", Leukemia, 17(7): 1294-1300, Jul. 2003.
Kasper et al. "Targeting MCL-1 Sensitizes FLT3-ITD-Positive Leukemias to Cytotoxic Therapies", Blood Cancer Journal,2: e60; 1-10, 2012.
Kaufman et al. "The Effect of Rituximab on Mobilization With AMD3100 Plus G-CSF in Patients With Relapsed or Refractory NHL or HD", Blood, ASH Annual Meeting Abstracts, 110(11/Pt. 1): 568A, # 1912, 49th Annual Meeting of the American-Society-of-Hematology, Atlanta, GA, USA, Dec. 8-11, 2007.
Kean et al. "Significant Mobilization of Both Conventional and Regulatory T Cells With AMD3100", Blood, 118(25): 6580-6590, Dec. 15, 2011.
Kim et al. "In Vitro Behavior of Hematopoietic Progenitor Cells Under the Influence of Chemoattractants: Stromal Cell-DErived Factor-1, Steel Factor, and the Bone Marrow Environment", Blood, 91(1): 100-110, 1998.
Kollet et al. "Human CD34+CXCR4—Sorted Cells Harbor Intracellular CXCR4, Which Can Be Functionally Expressed and Provide NOD/SCID Repopulation", Blood, 100(8): 2778-2786, 2002.
Koshiba et al. "Expression of Stromal Cell-Derived Factor 1 and CXCR4 Ligand Receptor System in Pancreatic Cancer: A Possible Role for Tumor Progression", Clinical Cancer Research, 6(9): 3530-3535, Sep. 2000.
Kucia et al. "Novel Direct Evidence That Adult Bone Marrow-Derived Very Small Embryonic Like (VSEL) Stem Cells Are Mobilized Into Peripheral Blood—Leukopheresis as a Potential Tool to Isolate Pluripotent Stem Cells for Therapeutic Purposes", Database BIOSIS [Online], Biosciences Information Service, XP002630526, Database Accession No. PREV200800216478, Nov. 2007. & Blood, 110(11/Pt.1): 364A, Nov. 2007 & 49th Annual Meeting of the American Society of Hematology, Atlanta, GA, USA, Dec. 8-11, 2007. Abstract.
Kucia et al. "Trafficking of Normal Stem Cells and Metastasis of Cancer Stem Cells Involve Similar Mechanisms: Pivotal Role of the SDF-1—CXCR4 Axis", Stem Cells, 23(7): 879-894, Aug. 2005.
Kumar et al. "Mobilization of Bone Marrow Mesenchymal Stem Cells In Vivo Augments Bone Healing in a Mouse Model of Segmental Bone Defect", Bone, 50(4): 1012-1018, Apr. 2012.
Lack et al. "A Pharmacokinetic-Pharmacodynamic Model for the Mobilization of CD34+ Hematopoietic Progenitor Cells by AMD3100", Clinical Pharmacology and Therapeutics, 77(5): 427-436, 2005.
Lanzkron et al. "Hematopietic Stem Cell Tracking Tn Vivo: A Comparison of Short-Term and Long-Term Repopulation Cells", Blood, 93(6): 1916-1921, Mar. 15, 1999.
Lapidot et al. "How Do Stem Cells Find Their Way Home?", Blood, 106(6): 1901-1910, 2005.
Lapidot et al. "The Essential Roles of the Chemokine SDF-1 and Its Receptor CXCR4 in Human Stem Cell Homing and Repopulation of Transplanted Immune-Deficient NOD/SCID and NOD/SClD/B2m<Null> Mice", Leukemia, 16(10): 1992-2003, 2002.
Leone et al. "A2aR Antagonists: Next Generation Checkpoint Blockade for Cancer Immunotherapy", Computational and Structural Biotechnology Journal, 13: 265-272, 2015.
Levesque et al. "Disruption of the CXCR4/CXCL12 Chemotactic Interaction During Hematopoietic Stem Cell Mobilization Induced by GCSF or Cyclophosphamide", Journal of Clinical Investigation, XP002630527, 111(2): 187-196, Jan. 2003. p. 190.
Levis et al. "FL T3: ITDoes Matter in Leukemia", Leukemia 17: 1738-1752, 2003.
Li et al. "Improving Chemotherapeutic Efficiency in Acute Myeloid Leukemia Treatments by Chemically Synthesized Peptide Interfering with CXCR4/CXCL12 Axis", Scientific Reports, 5: 16228, pp. 1-11, Nov. 5, 2015.
Liles et al. "Mobilization of Hematopoietic Progenitor Cells in Healthy Volunteers by AMD3100, a CXCR4 Antagonist", Blood, XP003001859, 102(8): 2728-2730, Oct. 15, 2003. p. 2729.

Lowenberg et al. "Cytarabine Dose for Acute Myeloid Leukemia", the New England Journal of Medicine, 364(11): 1027-1036, Mar. 17, 2011.
Mandawat et al. "Pan-Histone Deacetylase Inhibitor Panobinostat Depletes CXCR4 Levels and Signaling and Exerts Synergistic Antimyeloid Activity in Combination With CXCR4 Antagonists", Blood, XP002725236, 116(24): 5306-5315, Dec. 9, 2010. p. 5311, col. 4; p. 5312 col. 1.
Martin et al. "Chemokines Acting via CXCR2 and CXCR4 Control the Release of Neutrophils From the Bone Marrow and Their Return Following Senescence", Immunity, 19(4): 583-593, Oct. 2003.
Martin et al. "Tumor Angiogenesis Is Associated With Plasma Levels of Stromal-Derived Factor-1 [Alpha] in Patients With Multiple Myeloma", Clinical Cancer Research, XP055204518, 12(23): 6973-6977, Dec. 1, 2006. p. 6973.
Matthys et al. "AMD3100, a Potent and Specific Antagonist of the Stromal Cell-Derived Factor-1 Chemokine Receptor CXCR4, Inhibits Autoimmune Joint Inflammation in IFN-Gamma Receptor-Deficient Mice", the Journal of Immunology, 167(8): 4686-4692, 2001.
Menu et al. "The Involvement of Stromal Derived Factor 1 Alpha in Homing and Progression of Multiple Myeloma in the 5TMM Model", Haematologica/the Hematology Journal, XP002629046, 91(5): 605-612, May 1, 2006. p. 606.
Merck "Clinical Aspects of Cancer", The Merck Manual, 5 pages, Jun. 26, 2007.
Merck "Introduction: Overview of Cancer", The Merck Manual, 1 page, Jun. 26, 2007.
Merck "Rheumatoid Arthritis (RA)", The Merck Manual, 18th Ed., 9 pages, 2005.
Mijovic et al. "Harvesting, Processing and Inventory Management of Peripheral Blood Stem Cells", Asian Journal of Transfusion Science 1(1): pp. 1-10, 2007.
Mikayama et al. "Molecular Cloning and Functional Expression of a cDNA Encoding Glycosylation-Inhibiting Factor", Proc. Nat. Acad. Sci. USA, PNAS, 90: 10056-10060, Nov. 1993.
Mori et al. "Cytarabine Dose for Acute Myeloid Leukemia", The New England Journal of Medicine, 364(22): 2166-2169, Jun. 2, 2011.
Mori et al. "Involvement of Stromal Cell-Derived Factor 1 and CXCR4 Receptor System in Pancreatic Cancer", Gastroenterology, XP009021758, 122(4/Suppl.1): A490, Abstract # T1608, Apr. 2002.
Mueller et al. "Involvement of Chemokine Receptors in Breast Cancer Metastasis", Nature, 410: 50-56, Mar. 2001.
Munk Pedersen et al. "The Chimeric Anti-CD20 Antibody Rituximab Induces Apoptosis in B-Cell Chronic Lymphocytic Leukemia Cells Through a P38 Mitogen Activated Protein-Kinase-Dependent Mechanism", Blood, 99(4): 1314-1319, Feb. 15, 2002.
Nagasawa et al. "Molecular Cloning and Structure of a Pre-B-Cell Growth-Stimulating Factor", Proc. Natl. Acad. sci. USA. 91: 2305-2309, Mar. 1994.
Nakashima et al. "Anti-Human Immunodeficiency Virus Activity of a Novel Synthetic Peptide, T22 ([Tyr-5,12, Lys-7]Polyphemusin II): A Possible Inhibitor of Virus-Cell Fusion", Antimicrobial Agents and Chemotherapy, 36(6): 1249-1255, Jun. 1992.
Neidl "Failure Modes in the Discovery Process", Cancer Drug Design and Discovery, Chap. 18.2.2: 427-431, 2008.
Nervi et al. "Chemosensitization of Acute Myeloid Leukemia (AML) Following Mobilization by the CXCR4 Antagonist AMD3100", Blood, 113(24): 6206-6214, Published Online Dec. 2, 2008.
Ngo et al. "Computational Complexity, Protein Structure Prediction, and the Levinthal Paradox", the Protein Folding Problem and Tertiary Structure Prediction, Chap. 14: 433-440, 492-495, 1994.
Omagari et al. "Development of Specific CXCR4 Inhibitors Based on an Anti-HIV Peptide, T140, and Their Structure-Activity Relationships Study", Peptide Science, 2000(37): 129-132, 2001.
Paietta "Assessing Minimal Residual Disease (MRD) in Leukemia: A Changing Definition and Concept?", Bone Marrow Transplantation, 29:459-465, 2002.
Pardee et al. "Flt3-ITD Alters Chemotherapy Response in Vitro and in Vivo in a p53-Dependent Manner", Experimental Hematology, 39:473-485, 2011.

(56) References Cited

OTHER PUBLICATIONS

Pardoll "The Blockade of Immune Checkpoints in Cancer Immunotherapy", Nature Reviews Cancer,12(4): 252-264, Apr. 2012.
Peled et al. "Dependence of Human Stem Cell Engraftment and Repopulation of NOD/SCID Mice on CXCR4", Science, 283(5403): 845-848, 1999.
Peled et al. "Role of CXCR4 in the Pathogenesis of Acute Myeloid Leukemia", Theranostics, XP055164251, 3(1): 34-39, Jan. 13, 2013. Abstract.
Peled et al. "The High-Affinity CXCR4 Antagonist BKT140 Is Safe and Induces a Robust Mobilization of Human CD34+ Cells in Patients With Multiple Myeloma", Clinical Cancer Research, 20(2): 469-479, Published Online Nov. 18, 2013.
Pereg et al. "BL-8040, a CXCR4 Antagonist, Synergizes With the FLT3 Inhibitor AC220 Inducing Apoptosis and Reducing Minimal Residual Disease to Prolong Survival of AML Diseased Mice", Society of Hematologic Oncology, SOHO Annual Meeting Proceedings, XP055164272, 2(1): 203, Sep. 17, 2014. Abstract.
Phillips et al. "Epidermal Growth Factor and Hypoxia-Induced Expression of CXC Chemokine Receptor 4 on Non-Small Cell Lung Cancer Cells Is Regulated by the Phosphatidylinositol 3-Kinase/PTEN/AKT/Mammalian Target of Rapamycin Signaling Pathway and Activation of Hypoxia Inducible Factor-1 Alpha", The Journal of Biological Chemistry, 280(23): 22473-22481, 2005.
Phillips et al. "The Stromal Derived Factor-1/CXCL12-CXC Chemokine Receptor 4 Biological Axis in Non-Small Cell Lung Cancer Metastasis", 167: 1676-1686, 2003.
Pitchford et al. "Differential Mobilization of Subsets of Progenitor Cells From the Bone Marrow", Cell Stem Cell, 4: 62-72, Jan. 9, 2009.
Pottgen et al. "Intensified High-Dose Chemoradiotherapy With Induction Chemotherapy in Patients With Locally Advanced Non-Small-Cell Lung Cancer—Safety and Toxicity Results Within a Prospective Trial", International Journal of Radiation Oncology Biology Physics, 76(3): 809-815, Mar. 1, 2010.
Pratz et al. "Incorporating FL T3 Inhibitors Into Acute Myeloid Leukemia Treatment Regimens", Leukemia & Lymphoma, 49(5): 852-863, May 2008.
Princen et al. "HIV Chemokine Receptor Inhibitors as Novel Anti-HIV Drugs", Cytokine & Growth Factor Reviews, 16(6): 659-677, 2005.
Qin et al. "Effect of Cytarabine and Decitabine in Combination in Human Leukemic Cell Lines", Clinical Cancer Research, XP002725241, 13(14): 4225-4232, Jul. 15, 2007. Abstract, Fig. 3a, 4.
Ratajczak et al. "Stem Cell Plasticity Revisited: CXCR4-Positive Cells Expressing mRNA for Early Muscle, Liver and Neural Cells 'Hide Out' in the Bone Marrow", Leukemia, XP002604057, 18(1): 29-40, Jan. 1, 2004. p. 29.
Ratajczak et al. "T140 Enhances G-CSF-Induced Mobilization of Hematopoietic Stem Cells", Experimental Hematology, XP009146619, 31(7/Suppl.1): 154, Abstract #280, Jul. 2003. & 32nd Annual Meeting of the International Society for Experimental Hematology, Paris, France, Jul. 5-8, 2003. p. 154.
Ringe et al. "Towards In Situ Tissue Repair: Human Mesenchymal Stem Cells Express Chemokine Receptors CXCR1, CXCR2 and CCR2, and Migrate Upon Stimulation With CXCL8 But Not CCL2", Journal of Cellular Biochemistry, 101(1): 135-146, May 1, 2007.
Robak et al. "Current and Emerging Therapies for Acute Myeloid Leukemia", Clinical Therapeutics, 31(Pt.2): 2349-2370, Jan. 2009.
Rossi et al. "The Biology of Chemokines and Their Receptors", Annual Reviews of Immunology, 18: 217-242, 2000.
Rubin et al. "A Small-Molecule Antagonist of CXCR4 Inhibits Intracranial Growth of Primary Brain Tumors", Proc. Natl. Acad. Sci. USA, PNAS, 100(23): 13513-13518, Nov. 11, 2003.
Rubinow et al. "A Mathematical Model of the Chemotherapeutic Treatment of Acute Myeloblastic Leukemia", Biophysical Journal, XP009515513, 16(11): 1257-1271, Nov. 1976.
Russell et al. "CXCR4 Expression in Neuroblastoma Primary Tumors Is Associated With Clinical Presentation of Bone and Bone Marrow Metastases", Journal of Pediatric Surgery, 39(10): 1506-1511, Oct. 2004.
Sehn et al. "Treatment of Aggressive Non-Hodgkin's Lymphoma: A North American Perspective", Oncology, XP009177924, 19(4/Suppl. 1): 26-34, Apr. 2005.
Shim et al. "Chemokine Receptor CXCR4 as a Therapeutic Target for Neuroectodermal Tumors", Seminars in Cancer Biology, 19: 123-134, 2009.
Sison et al. "The Bone Marrow Microenvironment and Leukemia: Bbiology and Therapeutic Targeting", Expert Review of Hematology, 4(3): 271-283, Jun. 2011.
Sitkovsky et al. "Hypoxia-Adenosinergic Immunosuppression: Tumor Protection by T Regulatory Cells and Cancerous Tissue Hypoxia", Clinical Cancer Research, 14(19): 5947-5952, Oct. 1, 2008.
Skolnick et al. "From Genes to Protein Structure and Function: Novel Applications of Computational Approaches in the Genomic Era", Trends in Biotechnology, TIBTECH, 18(1): 34-39, Jan. 2000.
Sporn et al. "Chemoprevention of Cancer", Carcinogenesis, 21(3): 525-530, 2000.
Stewart et al. "World Cancer Report", International Agency for Research on Cancer, IARC Press, 5 Pages, Lyon, 2003.
Stone et al. "A Randomized Phase III Study of Induction (Daunorubicin/Cytarabine) and Consolidation (High-Dose Cytarabine) Chemotherapy Combined with Midostaurin or Placebo in Treatment-naive Patients with FLT3 Mutated AML", Journal of Clinical Oncology, 29(15): 4 P., Supplemental, 2011.
Su et al. "Differential Expression of CXCR4 Is Associated With the Metastatic Potential of Human Non-Small Cell Lung Cancer Cells", Clinical Cancer Research, XP055076137, 11(23): 8273-8280, Dec. 1, 2005.
Tamamura "Development of Selective Antagonists Against an HIV Second Receptor", Yakugaku Zasshi, 121(11): 781-792, 2001. Abstract in English.
Tamamura et al. "A Future Perspective on the Development of Chemokine Receptor CXCR4 Antagonists", Database EMBASE [Online], XP002675634, Database Accession No. EMB-2008509452, Oct. 2008. & Expert Opinion on Drug Discovery, 3(10): 1155-1166, Oct. 2008.
Tamamura et al. "A Low-Molecular-Weight Inhibitor Against the Chemokine Receptor CXCR4: A Strong Anti-HIV Paptide T140", Biochemical and Biophysical Research Communications, 253(3): 877-882, 1998.
Tamamura et al. "Certification of the Critical Importance of L-3-(2-Naphtyl)Alanine at Position 3 of a Specific CXCR4 Inhibitor, T140, Leads to an Exploratory Performance of Its Downsizing Study", Bioorganic & Medicinal Chemistry, 10: 1417-1426, 2002.
Tamamura et al. "Development of Specific CXCR4 Inhibitors Possessing High Selectivity Indexes as Well as Complete Stability in Serum Based on an Anti-HIV Peptide T140", Bioorganic & Medicinal Chemistry Letters, XP002265743, 11(14): 1897-1902, Jul. 23, 2001. Abstract, Fig.1, p. 1901, r-h col. Last Sentence Before 'Acknowledgements'.
Tamamura et al. "Downsizing of an HIV-Cell Fusion Inhibitor, T22 ([Tyr5,12, Lys7]-Polyphemusin II), With the Maintenance of Anti-HIV Activity and Solution Structure", Bioorganic & Medicinal Chemistry, 6: 473-479, 1998.
Tamamura et al. "Effective Lowly Cytotoxic Analogs of an HIV-Cell Fusion Inhibitor, T22 ([Tyr5,12, Lys7]-Polyphemusin II)", Bioorganic & Medicinal Chemistry, 6(2): 231-238, 1998.
Tamamura et al. "Efficient Analogs of an Anti-HIV Peptide, T22 ([Tyr5,12, Lys7]-Polyphemusin II), Having Low Cytotoxicity", Peptide Science—Present and Future, Proceedings of the 1st International Peptide Symposium, XP002973954, 1997: 427-429, Jan. 1, 1999. Abstract, Fig.2.
Tamamura et al. "Enhancement of the T140-Based Pharmacophores Leads to the Development of More Potent and Bio-Stable CXCR4 Antagonists", Organic Biomolecular Chemistry, 1: 3663-3669, 2003.
Tamamura et al. "HIV-Cell Fusion Inhibitors Targeted to the HIV Second Receptor: T22 and Its Downsized Analogs With High Activity", Peptide Science, 1998(35): 49-52, 1999.

(56) References Cited

OTHER PUBLICATIONS

Tamamura et al. "Pharmacophore Identification of a Specific CXCR4 Inhibitor, T140, Leads to Development of Effective Anti-HIV Agents With Very High Selectivity Indexes", Bioorganic & Medicinal Chemistry Letters, 10(23): 2633-2637, 2000.
Tamamura et al. "T140 Analogs as CXCR4 Antagonists Identified as Anti-Metastatic Agents in the Treatment of Breast Cancer", FEBS Letters, XP004448372, 550(1-3): 79-83, Aug. 28, 2003. Abstract.
Tamamura et al. "The Therapeutic Potential of CXCR4 Antagonists in the Treatment of HIV Infection, Cancer Metastasis and Rheumatoid Arthritis", Expert Opinion of Therapeutic Targets, 9(6): 1267-1282, 2005.
Tavor et al. "The CXCR4 Antagonist BL-8040 Efficiently Induces Apoptosis and Inhibits the Survival of AML Cells", Blood, 55th Annual Meeting of the American Society of Hematology, 122(21): # 3939, 5 P., Oct. 21, 2013.
Topalian et al. "Safety, Activity, and Immune Correlates of Anti-PD-1 Antibody in Cancer", The New England Journal of Medicine, 366(26): 2443-2454, Jun. 28, 2012.
Tsutsumi et al. "Therapeutic Potential of the Chemokine Receptor CXCR4 Antagonists as Multifunctional Agents", Peptide Science, XP002629052, 88(2): 279-289, Dec. 13, 2006. p. 280.
Ulvatne et al. "Short Antibacterial Peptides and Erythromycin Act Synergically Against *Escherichia coli*", Journal of Antimicrobial Chemotherapy. 48: 203-208, 2001.
Uy et al. "A Phase 1/2 Study of Chemosensitization With the CXCR4 Antagonist Plerixafor in Relapsed or Refractory Acute Myeloid Leukemia", Blood, XP002725214, 119(17): 3917-3924, Apr. 26, 2012.
Voermans et al. "Migratory Behavior of Leukemic Cells From Acute Myeloid Leukemia Patients", Leukemia, 16(4): 650-657, Apr. 2002.
Wang et al. "A Single Amino Acid Determines Lysophospholipid Specificity of the S1P1 (EDG1) and LPA1 (EDG2) Phospholipid Growth Factor Receptors",The Journal of Biological Chemistry, 276(52): 49213-49220, Dec. 28, 2001.
Weekes et al. "Stromal Derived Factorl Alpha Mediates Resistance to mTOR Inhibition by the Preservation of Hypoxia Inducible Factor-1 Alpha (HIF-1 Alpha) Expression", Proceedings of the Annual Meeting of the American Association for Cancer Research, AACR, 47: 553, Abstract #2341, 2006.
Weissman "Translating Stem and Progenitor Cell Biology to the Clinic: Barriers and Opportunities", Science, 287(5457): 1442-1446, Feb. 25, 2000.
Wells "Additivity of Mutational Effects in Proteins", Biochemistry, 29(37): 8509-8517, Sep. 18, 1990.
Whisstock et al. "Prediction of Protein Function from Protein Sequence and Structure", Quarterly Reviews of Biophysics 36(3): 307-340, 2003.
Wiernek et al. "Does High-Dose Cytarabine Cause Cumulative Toxicity in Patients Undergoing Consolidation Therapy for Acute Myeloid Leukemia?", 88(6): 533-534, Mar. 22, 2013.
Woo et al. "Immune Inhibitory Molecules LAG-3 and PD-1 Synergistically Regulate T Cell Function to Promote Tumoral Immune Escape", Cancer Research, XP055151722, 72(4): 917-927, Feb. 15, 2012.
Wynn et al. "A Small Proportion of Mesenchymal Stem Cells Strongly Expresses Functionally Active CXCR4 Receptor Capable of Promoting Migration to Bone Marrow", Blood, 104(9): 2643-2645, Prepublished Online Jul. 13, 2004.
Zagozdzon et al. "Csk Homologous Kinase Inhibits CXCL12-CXCR4 Signaling in Neuroblastoma", International Journal of Oncology, 32(3): 619-623, Mar. 2008.
Zannettino et al. "Elevated Serum Levels of Stromal-Derived Factor-1 Alpha Are Associated With Increased Osteoclast Activity and Osteolytic Bone Disease in Multiple Myeloma Patients", Cancer Research, 65(5): 1700-1709, Mar. 1, 2005. Abstract, p. 1705, p. 1707, Last Para—p. 1708, First Para.

Zeng et al. "Inhibition of CXCR4 With the Novel RCP168 Peptide Overcomes Stroma-Mediated Chemoresistance in Chronic and Acute Leukemias", Molecular Cancer Therapeutics, XP008139367, 5(12): 3113-3121, Dec. 2006.
Zeng et al. "Targeting the Leukemia Microenvironment by CXCR4 Inhibition Overcomes Resistance to Kinase Inhibitors and Chemotherapy in AML", Blood, XP002716127, 113(24): 6215-6224, Jun. 11, 2009. Abstract.
Zhang et al. "CXCR4 Inhibitors Selectively Eliminate CXCR4-Expressing Human Acute Myeloid Leukemia Cells in NOG Mouse Model", Cell Death and Disease, 3(10): e396-1-e396-11, Published Online Oct. 4, 2012.
Zhang et al. "Primitive Neuroectodermal Tumors of Adrenal Gland", Japanese Journal of Clinical Oncology, 40(8): 800-804, 2010.
Zhou et al. "CXCR4 Is A Major Chemokine Receptor on Glioma Cells and Mediates Their Survival", the Journal of Biological Chemistry, 277(51): 49481-49487, Dec. 29, 2002.
Zuluaga et al. "Neutropenia Induced in Outbred Mice by a Simplified Low-Dose Cyclophosphamide Regimen: Characterization and Applicability to Diverse Experimental Models of Infectious Diseases", BMC Infectious Diseases, 6(55): 1-10, Mar. 17, 2006.
Patent Examination Report dated Aug. 31, 2021 From the Australian Government, IP Australia Re. Application No. 2020203840. (5 Pages).
Official Action dated Apr. 2, 2021 from the US Patent and Trademark Office Re. U.S. Appl. No. 15/570,389. (31 pages).
Wise et al. "Modulation of Stromal Cell-Derived Factor-1/CXC Chemokine Receptor 4 Axis Enhances rhBMP-2-Induced Ectopic Bone Formation"; Tissue Engineering: Part A, 18(7-8): 860-869, Jan. 2, 2012.
Interview Summary dated Jan. 4, 2021 from the US Patent and Trademark Office Re. U.S. Appl. No. 16/078,696. (2 pages).
European Search Report and the European Search Opinion dated Apr. 11, 2022 From the European Patent Office Re. Application No. 21194845.0. (13 Pages).
Official Action dated Jun. 13, 2022 from US Patent and Trademark Office Re. U.S. Appl. No. 16/866,588. (68 pages).
Notice of Reason(s) for Rejection dated Dec. 21, 2021 From the Japan Patent Office Re. Application No. 2020-216934 and Its Translation Into English. (8 Pages).
Official Action dated Dec. 4, 2020 From the US Patent and Trademark Office Re. U.S. Appl. No. 15/571,069. (24 Pages).
Requisition by the Examiner dated Nov. 27, 2020 From the Innovation, Science and Economic Development Canada, Canadian Intellectual Property Office Re. Application No. 2,928,315. (7 Pages).
Official Action dated Aug. 2, 2022 from US Patent and Trademark Office Re. U.S. Appl. No. 16/866,595. (106 pages).
Official Action dated Sep. 1, 2020 from the US Patent and Trademark Office Re. U.S. Appl. No. 16/078,696. (44 pages).
Decision of Rejection dated Apr. 5, 2022 From the State Intellectual Property Office of the People's Republic of China Re. Application No. 2020-147572 and Its Translation Into English. (7 Pages).
Partial European Search Report and the European Provisional Opinion dated Oct. 16, 2020 From the European Patent Office Re. Application No. 20176901.5.
Camacho "CTLA-4 Blockade With Ipilimumab: Biology, Safety, Efficacy, and Future Considerations", Cancer Medicine, XP055736670, 4(5): 661-672, May 25, 2015.
European Search Report and the European Search Opinion dated Feb. 1, 2021 From the European Patent Office Re. Application No. 20176901.5. (13 Pages).
Office Action dated Nov. 17, 2021 From the Israel Patent Office Re. Application No. 274572 and Its Translation Into English. (7 Pages).
Examination Report dated Apr. 13, 2021 From the Servico Publico Federal, Ministerio da Economia, Institute Nacional da Propriedade Industrial do Brasil Re Application No. BR/P11009663.9 and Its Summary Into English. (7 Pages).
Official Action dated Jul. 20, 2020 from the US Patent and Trademark Office Re. U.S. Appl. No. 15/570,389. (165 pages).
Fricker et al. "Characterization of the Molecular Pharmacology of AMD3100: a Specific Antagonist of the G-Protein Coupled Chemokine Receptor, CXCR4", Biochemical Pharmacology 72: 588-596, 2006.

(56) References Cited

OTHER PUBLICATIONS

Fu et al. "A New Source of Mesenchymal Stem Cells for Articular Cartilage Repair", The American Journal of Sports Medicine 42 (3): 592-601, 2013.
Jarocha et al. "Adventage of Mesenchymal Stem Cells (MSC) Expansion Directly from Purified Bone Marrow CD105+ and CD271+ Cells", Folia Histochemica et Cytobiologica, 46 (3): 307-314, 2008.
Examination Report dated Sep. 9, 2021 From the Servico Publico Federal, Ministerio da Economia, Instituto Nacional da Propriedade Industrial do Brasil Re Application No. BR112015024558 7 and Its English Summary. (6 Pages).
Requisition by the Examiner dated Sep. 27, 2021 From the Innovation, Science and Economic Development Canada, Canadian Intellectual Property Office Re. Application No. 2,928,315. (3 Pages).
Final Official Action dated Jul. 29, 2021 from the US Patent and Trademark Office Re. U.S. Appl. No. 15/570,389. (23 pages).
Ground(s) of Reason of Rejection dated Dec. 23, 2021 From the Korean Intellectual Property Office Re. Application No. 2021-7021378 and Its Translation Into English. (5 Pages).
Partial European Search Report and the Provisional Opinion dated Jan. 3, 2022 From the European Patent Office Re. Application No. 21194845.0. (17 Pages).
Mahoney et al. "Combination Cancer Immunotherapy and New Immunomodulatory Targets", Nature Reviews Drug Discovery, 14(8): 561-584, XP055240362, Jul. 31, 2015.
Notification of Office Action and Search Report dated Aug. 26, 2021 From the State Intellectual Property Office of the People's Republic of China Re. Application No. 202010413682.4 and Its Translation of Office Action Into English. (13 Pages).
Official Action dated Aug. 8, 2022 from US Patent and Trademark Office Re. U.S. Appl. No. 16/866,597. (104 pages).
Search Report and Opinion dated Aug. 7, 2020 From the Servico Publico Federal, Ministerio da Economia, Instituto Nacional da Propriedade Industrial Re. Application No. PI 1009663-9 and Its Translation of Opinion Into English. (6 Pages).
Advisory Action dated Mar. 8, 2021 From the US Patent and Trademark Office Re. U.S. Appl. No. 14/771,513. (3 Pages).
Official Action dated May 28, 2021 From the US Patent and Trademark Office Re. U.S. Appl. No. 15/571,069. (18 Pages).
Final Official Action dated Jan. 18, 2022 from US Patent and Trademark Office Re. U.S. Appl. No. 15/571,069. (22 pages).
Examination Report dated Apr. 12, 2022 From the Instituto Mexicano de la Propiedad Industrial, Direccion Divisional de Patentes Re. Application No. MX/a?2018/010125 and Its Summary in English. (7 Pages).
Notice of Reason(s) for Rejection dated Aug. 17, 2021 From the Japan Patent Office Re. Application No. 2020-147572 and Its Translation Into English. (7 Pages).
Official Action dated Jul. 8, 2022 from US Patent and Trademark Office Re. U.S. Appl. No. 16/866,593. (137 pages).
Official Action dated Sep. 15, 2022 From the US Patent and Trademark Office Re. U.S. Appl. No. 17/006,954. (290 Pages).
Dimitrov "Therapeutic Proteins", Methods in Molecular Biology book series (MIMB,vol. 899): 1-26, Jan. 29, 2020.
Lines et al. "VISTA Is an Immune Checkpoint Molecule for Human T Cells", Microenvironment and Immunology, Cancer Research 74 (7): 1924-1932, Apr. 1, 2014.

Mao et al. "B7—H1 and B7—H3 are Independent Predictors of Poor Prognosis in Patients with Non-small Cell Lung Cancer", Oncotarget 6(5): 3452-3461, Feb. 2015.
Wang et al. "B7—H4, a Promising Target for Immunotherapy", Cellular Immunology 347:104008 , Jan. 2020.
Zhou et al. "B7—H3/CD276: An Emerging Cancer Immunotherapy", NCBI Frontiers in Immunology 12: 701006, 1-13, Jul. 19, 2021.
Examination Report dated Aug. 25, 2022 From the Instituto Mexicano de la Propiedad Industrial, Direccion Divisional de Patentes Re. Application No. MX/a/2020/004969 and Its Summary in English. (16 Pages).
Notification of Office Action dated Jul. 29, 2022 From the State Intellectual Property Office of the People's Republic of China Re. Application No. 202010413682.4 and Its Translation Into English. (10 Pages).
Notice of Allowance dated Nov. 2, 2022 from the US Patent and Trademark Office Re. U.S. Appl. No. 16/866,592. (29 pages).
Notice of Allowance dated Nov. 9, 2022 from the US Patent and Trademark Office Re. U.S. Appl. No. 16/866,593. (29 pages).
Official Action dated Nov. 1, 2022 from the US Patent and Trademark Office Re. U.S. Appl. No. 16/866,606. (125 pages).
Examination Report Under Sections 12 & 13 of the Patents Act, 1970 and the Patents Rules, 2003 dated 003 Nov. 2022 from the Indian Patent Office Re. Application No. 202028020205. (7 pages).
Grounds of Reason of Rejection dated Oct. 27, 2022 From the Korean Intellectual Property Office Re. Application No. 10-2021-7021378 and its Translation into English. (8 Pages).
Official Action dated Nov. 14, 2022 from the US Patent and Trademark Office Re. U.S. Appl. No. 16/866,609. (362 pages).
Notice of Allowance dated Oct. 24, 2022 from the US Patent and Trademark Office Re. U.S. Appl. No. 16/866,588. (98 pages).
Official Action dated Oct. 24, 2022 from the US Patent and Trademark Office Re. U.S. Appl. No. 16/866,602. (126 pages).
Requisition by the Examiner dated Aug. 26, 2022 From the Innovation, Science and Economic Development Canada, Canadian Intellectual Property Office Re. Application No. 2,986,705. (12 Pages).
Official Action dated Dec. 30, 2022 from the US Patent and Trademark Office Re. U.S. Appl. No. 16/866,640. (138 pages).
Final Official Action dated dated Dec. 2, 2022 from the US Patent and Trademark Office Re. U.S. Appl. No. 16/866,597. (31 pages).
Final Official Action dated dated Dec. 2, 2022 from the US Patent and Trademark Office Re. U.S. Appl. No. 16/866,598. (31 pages).
Official Action dated Oct. 5, 2022 from US Patent and Trademark Office Re. U.S. Appl. No. 16/866,599. (195 pages).
Notice of Allowance dated Dec. 9, 2022 from the US Patent and Trademark Office Re. U.S. Appl. No. 16/866,595. (18 pages).
Official Action dated Dec. 12, 2022 from the US Patent and Trademark Office Re. U.S. Appl. No. 16/866,627. (33 pages).
Official Action dated Nov. 30, 2022 from the US Patent and Trademark Office Re. U.S. Appl. No. 16/866,615. (130 pages).
Examination Report dated Jul. 8, 2022 From the Instituto Mexicano de la Propiedad Industrial, Direccion Divisional de Patentes Re. Application No. MX/a/2018/010125 and Its Translation Into English. (10 Pages).
Official Action dated Sep. 7, 2022 from US Patent and Trademark Office Re. U.S. Appl. No. 16/866,603. (112 pages).
Official Action dated Sep. 7, 2022 from US Patent and Trademark Office Re. U.S. Appl. No. 16/866,605. (112 pages).
Official Action dated Aug. 18, 2022 From the US Patent and Trademark Office Re. U.S. Appl. No. 16/866,598. (106 Pages).

SEQUENCE LISTING

```
<160> NUMBER OF SEQ ID NOS: 72

<210> SEQ ID NO 1
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: 4-fluorobenzoyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 1

Xaa Arg Xaa Cys Tyr Xaa Lys Xaa Pro Tyr Arg Xaa Cys Arg
1               5                   10

<210> SEQ ID NO 2
<211> LENGTH: 14
```

```
<212> TYPE: PRT
<213> ORGANISM: Artificial
<220> FEATURE:
<223> OTHER INFORMATION: SYNTHETIC PEPTIDE
<220> FEATURE:
<221> NAME/KEY: MOD_RES
<222> LOCATION: (1)..(1)
<223> OTHER INFORMATION: N' ACETYLATION
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 2

Arg Arg Xaa Cys Tyr Xaa Lys Xaa Pro Tyr Arg Xaa Cys Arg
1               5                   10

<210> SEQ ID NO 3
<211> LENGTH: 14
<212> TYPE: PRT
<213> ORGANISM: Artificial
<220> FEATURE:
<223> OTHER INFORMATION: SYNTHETIC PEPTIDE
<220> FEATURE:
<221> NAME/KEY: MOD_RES
<222> LOCATION: (1)..(1)
<223> OTHER INFORMATION: N' ACETYLATION
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline

<400> SEQUENCE: 3

Arg Arg Xaa Cys Tyr Arg Lys Xaa Pro Tyr Arg Xaa Cys Arg
1               5                   10

<210> SEQ ID NO 4
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
```

```
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline

<400> SEQUENCE: 4

Arg Arg Xaa Cys Tyr Xaa Lys Xaa Pro Tyr Arg Xaa Cys Arg
1               5                   10

<210> SEQ ID NO 5
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (11)..(12)
<223> OTHER INFORMATION: citrulline

<400> SEQUENCE: 5

Arg Arg Xaa Cys Tyr Xaa Lys Xaa Pro Tyr Xaa Xaa Cys Arg
1               5                   10

<210> SEQ ID NO 6
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' acetylated citrulline
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 6

Xaa Arg Xaa Cys Tyr Xaa Lys Xaa Pro Tyr Arg Xaa Cys Arg
1               5                   10
```

```
<210> SEQ ID NO 7
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' acetylated citrulline
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline

<400> SEQUENCE: 7

Xaa Arg Xaa Cys Tyr Arg Lys Xaa Pro Tyr Arg Xaa Cys Arg
1               5                   10

<210> SEQ ID NO 8
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (11)..(12)
<223> OTHER INFORMATION: citrulline

<400> SEQUENCE: 8

Arg Arg Xaa Cys Tyr Arg Lys Xaa Pro Tyr Xaa Xaa Cys Arg
1               5                   10

<210> SEQ ID NO 9
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED citrulline
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
```

```
<222> LOCATION: (11)..(12)
<223> OTHER INFORMATION: citrulline

<400> SEQUENCE: 9

Xaa Arg Xaa Cys Tyr Arg Lys Xaa Pro Tyr Xaa Xaa Cys Arg
1               5                   10

<210> SEQ ID NO 10
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 10

Arg Arg Xaa Cys Tyr Xaa Lys Xaa Pro Tyr Arg Xaa Cys Arg
1               5                   10

<210> SEQ ID NO 11
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (11)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 11
```

Arg Arg Xaa Cys Tyr Xaa Lys Xaa Pro Tyr Xaa Xaa Cys Arg
1               5                   10

<210> SEQ ID NO 12
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED citrulline
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: AMIDATED

<400> SEQUENCE: 12

Xaa Arg Xaa Cys Tyr Xaa Lys Xaa Pro Tyr Arg Xaa Cys Arg
1               5                   10

<210> SEQ ID NO 13
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED citrulline
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 13

Xaa Arg Xaa Cys Tyr Arg Lys Xaa Pro Tyr Arg Xaa Cys Arg
1               5                   10

<210> SEQ ID NO 14
<211> LENGTH: 14
<212> TYPE: PRT
<213> ORGANISM: Artificial
<220> FEATURE:

```
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (11)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 14

Arg Arg Xaa Cys Tyr Arg Lys Xaa Pro Tyr Xaa Xaa Cys Arg
1               5                   10

<210> SEQ ID NO 15
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED citrulline
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (11)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 15

Xaa Arg Xaa Cys Tyr Arg Lys Xaa Pro Tyr Xaa Xaa Cys Arg
1               5                   10

<210> SEQ ID NO 16
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: D-glutamic acid
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
```

```
<220> FEATURE:
<221> NAME/KEY: MOD_RES
<222> LOCATION: (12)..(12)
<223> OTHER INFORMATION: citrulline

<400> SEQUENCE: 16

Xaa Arg Xaa Cys Tyr Arg Lys Xaa Pro Tyr Arg Xaa Cys Arg
1               5                   10

<210> SEQ ID NO 17
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 17

Arg Glu Xaa Cys Tyr Arg Lys Xaa Pro Tyr Arg Xaa Cys Arg
1               5                   10

<210> SEQ ID NO 18
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 18

Arg Arg Xaa Cys Tyr Glu Lys Xaa Pro Tyr Arg Xaa Cys Arg
1               5                   10

<210> SEQ ID NO 19
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline
```

<400> SEQUENCE: 19

Arg Arg Xaa Cys Tyr Arg Glu Xaa Pro Tyr Arg Xaa Cys Arg
1               5                   10

<210> SEQ ID NO 20
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline

<400> SEQUENCE: 20

Arg Arg Xaa Cys Tyr Arg Lys Xaa Pro Tyr Arg Xaa Cys Arg
1               5                   10

<210> SEQ ID NO 21
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 21

Arg Arg Xaa Cys Tyr Arg Lys Xaa Pro Tyr Glu Xaa Cys Arg
1               5                   10

<210> SEQ ID NO 22
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 22

Arg Arg Xaa Cys Tyr Arg Lys Xaa Pro Tyr Arg Xaa Cys Glu

-continued

```
1               5                   10

<210> SEQ ID NO 23
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' amidated

<400> SEQUENCE: 23

Arg Arg Xaa Cys Tyr Xaa Lys Xaa Pro Tyr Arg Xaa Cys Arg
1               5                   10

<210> SEQ ID NO 24
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: D-glutamic acid
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 24

Arg Arg Xaa Cys Tyr Xaa Lys Xaa Pro Tyr Arg Xaa Cys Arg
1               5                   10

<210> SEQ ID NO 25
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
```

<220> FEATURE:
<221> NAME/KEY: MOD_RES
<222> LOCATION: (6)..(6)
<223> OTHER INFORMATION: D-glutamic acid
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 25

Arg Arg Xaa Cys Tyr Xaa Lys Xaa Pro Tyr Arg Xaa Cys Arg
1               5                   10

<210> SEQ ID NO 26
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: D-glutamic acid
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 26

Xaa Arg Xaa Cys Tyr Xaa Lys Xaa Pro Tyr Arg Xaa Cys Arg
1               5                   10

<210> SEQ ID NO 27
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:

```
<221> NAME/KEY: MOD_RES
<222> LOCATION: (10)..(10)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 27

Arg Arg Xaa Cys Tyr Xaa Lys Xaa Pro Xaa Arg Xaa Cys Arg
1               5                   10

<210> SEQ ID NO 28
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: D-glutamic acid
<220> FEATURE:
<221> NAME/KEY: MOD_RES
<222> LOCATION: (14)..(14)
<223> OTHER INFORMATION: c' amidated

<400> SEQUENCE: 28

Arg Arg Xaa Cys Tyr Xaa Lys Xaa Pro Tyr Arg Xaa Cys Arg
1               5                   10

<210> SEQ ID NO 29
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED D-glutamic acid
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
```

<222> LOCATION: (14)..(14)
<223> OTHER INFORMATION: c' amidated

<400> SEQUENCE: 29

Xaa Arg Xaa Cys Tyr Xaa Lys Xaa Pro Tyr Arg Xaa Cys Arg
1               5                   10

<210> SEQ ID NO 30
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (10)..(10)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 30

Arg Arg Xaa Cys Tyr Xaa Lys Xaa Pro Xaa Arg Xaa Cys Arg
1               5                   10

<210> SEQ ID NO 31
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: D-glutamic acid
<220> FEATURE:
<221> NAME/KEY: MOD_RES
<222> LOCATION: (14)..(14)

<223> OTHER INFORMATION: c' amidated

<400> SEQUENCE: 31

Arg Arg Xaa Cys Tyr Xaa Lys Xaa Pro Tyr Arg Xaa Cys Arg
1               5                   10

<210> SEQ ID NO 32
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 32

Arg Arg Xaa Cys Tyr Xaa Lys Xaa Pro Tyr Arg Xaa Cys Arg
1               5                   10

<210> SEQ ID NO 33
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Guanyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 33

Xaa Arg Xaa Cys Tyr Xaa Lys Xaa Pro Tyr Arg Xaa Cys Arg

<210> SEQ ID NO 34
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Tetramethylguanyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 34

Xaa Arg Xaa Cys Tyr Xaa Lys Xaa Pro Tyr Arg Xaa Cys Arg
1               5                   10

<210> SEQ ID NO 35
<211> LENGTH: 13
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Tetramethylguanyl-arginine
<220> FEATURE:
<221> NAME/KEY: MOD_RES
<222> LOCATION: (2)..(2)
<223> OTHER INFORMATION: 3-((2-naphthyl) alanine
<220> FEATURE:
<221> NAME/KEY: MOD_RES
<222> LOCATION: (5)..(5)
<223> OTHER INFORMATION: citrulline
<220> FEATURE:
<221> NAME/KEY: MOD_RES
<222> LOCATION: (7)..(7)
<223> OTHER INFORMATION: D-glutamic acid
<220> FEATURE:
<221> NAME/KEY: MOD_RES
<222> LOCATION: (11)..(11)
<223> OTHER INFORMATION: citrulline
<220> FEATURE:
<221> NAME/KEY: MOD_RES
<222> LOCATION: (13)..(13)
<223> OTHER INFORMATION: c' amidated

<400> SEQUENCE: 35

Xaa Xaa Cys Tyr Xaa Lys Xaa Pro Tyr Arg Xaa Cys Arg
1               5                   10

<210> SEQ ID NO 36
<211> LENGTH: 14

```
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: 4-fluorobenzoyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: amidated

<400> SEQUENCE: 36

Xaa Arg Xaa Cys Tyr Xaa Lys Xaa Pro Tyr Arg Xaa Cys Arg
1               5                   10

<210> SEQ ID NO 37
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: 2-fluorobenzoyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 37

Xaa Arg Xaa Cys Tyr Xaa Lys Xaa Pro Tyr Arg Xaa Cys Arg
1               5                   10

<210> SEQ ID NO 38
<211> LENGTH: 13
<212> TYPE: PRT
<213> ORGANISM: Artificial
<220> FEATURE:
<223> OTHER INFORMATION: synthetic peptide
<220> FEATURE:
```

```
<221> NAME/KEY: MOD_RES
<222> LOCATION: (1)..(1)
<223> OTHER INFORMATION: 5-aminopentanoyl-arginine
<220> FEATURE:
<221> NAME/KEY: MOD_RES
<222> LOCATION: (2)..(2)
<223> OTHER INFORMATION: 3-((2-naphthyl) alanine
<220> FEATURE:
<221> NAME/KEY: MOD_RES
<222> LOCATION: (5)..(5)
<223> OTHER INFORMATION: citrulline
<220> FEATURE:
<221> NAME/KEY: MOD_RES
<222> LOCATION: (7)..(7)
<223> OTHER INFORMATION: D-glutamic acid
<220> FEATURE:
<221> NAME/KEY: MOD_RES
<222> LOCATION: (11)..(11)
<223> OTHER INFORMATION: citrulline
<220> FEATURE:
<221> NAME/KEY: MOD_RES
<222> LOCATION: (13)..(13)
<223> OTHER INFORMATION: c' amidated

<400> SEQUENCE: 38

Xaa Xaa Cys Tyr Xaa Lys Xaa Pro Tyr Arg Xaa Cys Arg
1               5                   10

<210> SEQ ID NO 39
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: 2-desamino-arginyl
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 39

Xaa Arg Xaa Cys Tyr Xaa Lys Xaa Pro Tyr Arg Xaa Cys Arg
1               5                   10

<210> SEQ ID NO 40
<211> LENGTH: 13
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Guanyl-arginine
<220> FEATURE:
<221> NAME/KEY: MOD_RES
```

```
<222> LOCATION: (2)..(2)
<223> OTHER INFORMATION: 3-((2-naphthyl) alanine
<220> FEATURE:
<221> NAME/KEY: MOD_RES
<222> LOCATION: (5)..(5)
<223> OTHER INFORMATION: citrulline
<220> FEATURE:
<221> NAME/KEY: MOD_RES
<222> LOCATION: (7)..(7)
<223> OTHER INFORMATION: D-glutamic acid
<220> FEATURE:
<221> NAME/KEY: MOD_RES
<222> LOCATION: (11)..(11)
<223> OTHER INFORMATION: citrulline
<220> FEATURE:
<221> NAME/KEY: MOD_RES
<222> LOCATION: (13)..(13)
<223> OTHER INFORMATION: c' amidated

<400> SEQUENCE: 40

Xaa Xaa Cys Tyr Xaa Lys Xaa Pro Tyr Arg Xaa Cys Arg
1               5                   10

<210> SEQ ID NO 41
<211> LENGTH: 13
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Succinyl-arginine
<220> FEATURE:
<221> NAME/KEY: MOD_RES
<222> LOCATION: (2)..(2)
<223> OTHER INFORMATION: 3-((2-naphthyl) alanine
<220> FEATURE:
<221> NAME/KEY: MOD_RES
<222> LOCATION: (5)..(5)
<223> OTHER INFORMATION: citrulline
<220> FEATURE:
<221> NAME/KEY: MOD_RES
<222> LOCATION: (7)..(7)
<223> OTHER INFORMATION: D-glutamic acid
<220> FEATURE:
<221> NAME/KEY: MOD_RES
<222> LOCATION: (11)..(11)
<223> OTHER INFORMATION: citrulline
<220> FEATURE:
<221> NAME/KEY: MOD_RES
<222> LOCATION: (13)..(13)
<223> OTHER INFORMATION: c' amidated

<400> SEQUENCE: 41

Xaa Xaa Cys Tyr Xaa Lys Xaa Pro Tyr Arg Xaa Cys Arg
1               5                   10

<210> SEQ ID NO 42
<211> LENGTH: 13
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Glutaryl-arginine
<220> FEATURE:
<221> NAME/KEY: MOD_RES
<222> LOCATION: (2)..(2)
<223> OTHER INFORMATION: 3-((2-naphthyl) alanine
<220> FEATURE:
<221> NAME/KEY: MOD_RES
<222> LOCATION: (5)..(5)
```

```
<223> OTHER INFORMATION: citrulline
<220> FEATURE:
<221> NAME/KEY: MOD_RES
<222> LOCATION: (7)..(7)
<223> OTHER INFORMATION: D-glutamic acid
<220> FEATURE:
<221> NAME/KEY: MOD_RES
<222> LOCATION: (11)..(11)
<223> OTHER INFORMATION: citrulline
<220> FEATURE:
<221> NAME/KEY: MOD_RES
<222> LOCATION: (13)..(13)
<223> OTHER INFORMATION: c' amidated

<400> SEQUENCE: 42

Xaa Xaa Cys Tyr Xaa Lys Xaa Pro Tyr Arg Xaa Cys Arg
1               5                   10

<210> SEQ ID NO 43
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: desaminoTMG-APA (formula IV in the
      specification)
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 43

Xaa Arg Xaa Cys Tyr Xaa Lys Xaa Pro Tyr Arg Xaa Cys Arg
1               5                   10

<210> SEQ ID NO 44
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: R-CH2 - formula (V) in the specification
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
```

```
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 44

Xaa Arg Xaa Cys Tyr Xaa Lys Xaa Pro Tyr Arg Xaa Cys Arg
1               5                   10

<210> SEQ ID NO 45
<211> LENGTH: 13
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: 3-((2-naphthyl) alanine
<220> FEATURE:
<221> NAME/KEY: MOD_RES
<222> LOCATION: (5)..(5)
<223> OTHER INFORMATION: citrulline
<220> FEATURE:
<221> NAME/KEY: MOD_RES
<222> LOCATION: (7)..(7)
<223> OTHER INFORMATION: D-glutamic acid
<220> FEATURE:
<221> NAME/KEY: MOD_RES
<222> LOCATION: (11)..(11)
<223> OTHER INFORMATION: citrulline
<220> FEATURE:
<221> NAME/KEY: MOD_RES
<222> LOCATION: (13)..(13)
<223> OTHER INFORMATION: c' amidated

<400> SEQUENCE: 45

Arg Xaa Cys Tyr Xaa Lys Xaa Pro Tyr Arg Xaa Cys Arg
1               5                   10

<210> SEQ ID NO 46
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: tetramethylguanyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED
```

<400> SEQUENCE: 46

Xaa Arg Xaa Cys Tyr Xaa Lys Xaa Pro Tyr Arg Xaa Cys Arg
1               5                   10

<210> SEQ ID NO 47
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: 6-aminohexanoyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 47

Xaa Arg Xaa Cys Tyr Xaa Lys Xaa Pro Tyr Arg Xaa Cys Arg
1               5                   10

<210> SEQ ID NO 48
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: 6-aminohexanoyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 48

Xaa Arg Xaa Cys Tyr Arg Lys Xaa Pro Tyr Arg Xaa Cys Arg
1               5                   10

<210> SEQ ID NO 49
<211> LENGTH: 14
<212> TYPE: PRT
<213> ORGANISM: Artificial
<220> FEATURE:
<223> OTHER INFORMATION: synthetic peptide -continued

```
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' amidated

<400> SEQUENCE: 49

Arg Arg Xaa Cys Tyr Xaa Arg Xaa Pro Tyr Arg Xaa Cys Arg
1               5                   10

<210> SEQ ID NO 50
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' amidated

<400> SEQUENCE: 50

Arg Arg Xaa Cys Tyr Xaa Arg Xaa Pro Tyr Arg Xaa Cys Arg
1               5                   10

<210> SEQ ID NO 51
<211> LENGTH: 14
<212> TYPE: PRT
<213> ORGANISM: Artificial
<220> FEATURE:
<223> OTHER INFORMATION: SYNTHETIC PEPTIDE
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
```

```
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 51

Arg Arg Xaa Cys Tyr Xaa Lys Xaa Pro Tyr Arg Xaa Cys Arg
 1               5                  10

<210> SEQ ID NO 52
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 52

Arg Arg Xaa Cys Tyr Arg Lys Xaa Pro Tyr Arg Xaa Cys Arg
 1               5                  10

<210> SEQ ID NO 53
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: 4-fluorobenzoyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
```

```
<222> LOCATION: (12)..(12)
<223> OTHER INFORMATION: citrulline
<220> FEATURE:
<221> NAME/KEY: MISC_FEATURE
<222> LOCATION: (14)..(14)
<223> OTHER INFORMATION: derivatization by a NH-methyl group

<400> SEQUENCE: 53

Xaa Arg Xaa Cys Tyr Xaa Lys Xaa Pro Tyr Arg Xaa Cys Arg
1               5                   10

<210> SEQ ID NO 54
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: 4-fluorobenzoyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MISC_FEATURE
<222> LOCATION: (14)..(14)
<223> OTHER INFORMATION: derivatization by a NH-ethyl group

<400> SEQUENCE: 54

Xaa Arg Xaa Cys Tyr Xaa Lys Xaa Pro Tyr Arg Xaa Cys Arg
1               5                   10

<210> SEQ ID NO 55
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: 4-fluorobenzoyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MISC_FEATURE
<222> LOCATION: (14)..(14)
```

<223> OTHER INFORMATION: derivatization by NH-isopropyl

<400> SEQUENCE: 55

Xaa Arg Xaa Cys Tyr Xaa Lys Xaa Pro Tyr Arg Xaa Cys Arg
1               5                   10

<210> SEQ ID NO 56
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: 4-fluorobenzoyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MISC_FEATURE
<222> LOCATION: (14)..(14)
<223> OTHER INFORMATION: derivatization with a tyramine residue

<400> SEQUENCE: 56

Xaa Arg Xaa Cys Tyr Xaa Lys Xaa Pro Tyr Arg Xaa Cys Arg
1               5                   10

<210> SEQ ID NO 57
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 57

Ala Arg Xaa Cys Tyr Arg Lys Xaa Pro Tyr Arg Xaa Cys Arg
1               5                   10

<210> SEQ ID NO 58
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (3)..(3)

-continued

```
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 58

Arg Arg Xaa Cys Tyr Ala Lys Xaa Pro Tyr Arg Xaa Cys Arg
1               5                   10

<210> SEQ ID NO 59
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 59

Arg Arg Xaa Cys Tyr Arg Ala Xaa Pro Tyr Arg Xaa Cys Arg
1               5                   10

<210> SEQ ID NO 60
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-alanine
<220> FEATURE:
<221> NAME/KEY: MOD_RES
<222> LOCATION: (12)..(12)
<223> OTHER INFORMATION: citrulline

<400> SEQUENCE: 60

Arg Arg Xaa Cys Tyr Arg Lys Xaa Pro Tyr Arg Xaa Cys Arg
1               5                   10

<210> SEQ ID NO 61
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
```

```
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 61

Arg Arg Xaa Cys Tyr Arg Lys Xaa Ala Tyr Arg Xaa Cys Arg
1               5                   10

<210> SEQ ID NO 62
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 62

Arg Arg Xaa Cys Tyr Arg Lys Xaa Pro Ala Arg Xaa Cys Arg
1               5                   10

<210> SEQ ID NO 63
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 63

Arg Arg Xaa Cys Tyr Arg Lys Xaa Pro Tyr Ala Xaa Cys Arg
1               5                   10

<210> SEQ ID NO 64
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: citrulline
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
```

-continued

```
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 64

Xaa Arg Xaa Cys Tyr Arg Lys Xaa Pro Tyr Arg Xaa Cys Arg
1               5                   10

<210> SEQ ID NO 65
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 65

Arg Arg Xaa Cys Tyr Xaa Lys Xaa Pro Tyr Arg Xaa Cys Arg
1               5                   10

<210> SEQ ID NO 66
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 66

Arg Arg Xaa Cys Tyr Xaa Lys Xaa Pro Tyr Arg Xaa Cys Arg
1               5                   10

<210> SEQ ID NO 67
<211> LENGTH: 14
<212> TYPE: PRT
<213> ORGANISM: Artificial
<220> FEATURE:
```

```
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (7)..(7)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 67

Arg Arg Xaa Cys Tyr Arg Xaa Xaa Pro Tyr Arg Xaa Cys Arg
1               5                   10

<210> SEQ ID NO 68
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 68

Arg Arg Xaa Cys Tyr Xaa Lys Xaa Pro Tyr Arg Xaa Cys Arg
1               5                   10

<210> SEQ ID NO 69
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 69

Arg Arg Xaa Cys Tyr Arg Lys Xaa Pro Tyr Arg Xaa Cys Arg
```

<210> SEQ ID NO 70
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline

<400> SEQUENCE: 70

Arg Arg Xaa Cys Tyr Xaa Lys Xaa Pro Tyr Arg Xaa Cys Arg
1               5                   10

<210> SEQ ID NO 71
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline

<400> SEQUENCE: 71

Arg Arg Xaa Cys Tyr Arg Lys Xaa Pro Tyr Arg Xaa Cys Arg
1               5                   10

<210> SEQ ID NO 72
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: citrulline
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline

```
-continued

<220> FEATURE:
<221> NAME/KEY: MOD_RES
<222> LOCATION: (14)..(14)
<223> OTHER INFORMATION: C' Amidated

<400> SEQUENCE: 72

Xaa Arg Xaa Cys Tyr Arg Lys Xaa Pro Tyr Arg Xaa Cys Arg
1               5                   10
```

COMPOSITIONS AND METHODS FOR TREATING CANCER

RELATED APPLICATIONS

This application is a continuation of U.S. patent application Ser. No. 15/571,505 filed on Nov. 3, 2017, which is a National Phase of PCT Patent Application No. PCT/IL2016/050764 having International Filing Date of Jul. 14, 2016, which claims the benefit of priority under 35 USC § 119(e) of U.S. Provisional Patent Application Nos. 62/291,039 filed on Feb. 4, 2016, 62/259,182 filed on Nov. 24, 2015, 62/291,006 filed on Feb. 4, 2016 and 62/193,201 filed on Jul. 16, 2015. The contents of the above applications are all incorporated by reference as if fully set forth herein in their entirety.

SEQUENCE LISTING STATEMENT

The ASCII file, entitled 82476SequenceListing.txt, created on Apr. 15, 2020, comprising 39,896 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to methods of treating cancer and, more particularly, but not exclusively, to the use of a CXCR4 antagonistic peptide and an immune-check point regulator in the treatment of cancer.

Cancer is the second leading cause of death in the U.S.A. The estimates for 2014 are that approximately 585,000 people will die of cancer and 1.6 million new cases will be diagnosed (American Cancer Society, Cancer Facts & Figures 2014).

For early stage cancers, surgical removal is a very effective treatment.

However, for more advanced cases and non-solid hematological malignancies, standard, non-specific cancer treatments such as chemotherapy and radiotherapy are typically used. These treatments affect many healthy cells and result in elevated toxicity and effective in only a minor percentage of treated individuals. Moreover, even individuals that initially respond to therapy are at risk for relapses, and often develop resistance.

Significant progress in understanding the underlying principles of tumor biology as well as the basic mechanisms of the immune response to cancer have led to the development of new immunotherapies aimed at employing the adaptive immune system to eradicate cancer with enhanced efficacy and reduced toxicity. Until recently, cancer immunotherapy had focused on approaches that enhance anti-tumor immune responses by adoptive-transfer of activated effector cells, immunization against relevant antigens, or providing non-specific immune-stimulatory agents such as cytokines. In the past decade, however, intensive efforts to develop specific immune checkpoint pathway inhibitors and co-stimulatory pathway activators have begun to provide new immunotherapeutics for treating cancer. Thus, for example, ipilimumab (YERVOY®), an antibody that binds to and inhibits the immune regulatory protein CTLA-4 and pembrolizumab (KEYTRUDA®), an antibody that binds to and inhibits the immune regulatory protein PD1, have been approved by the United States Food and Drug Administration for the treatment of melanoma. Other anti-PD-1 antibodies (such as Nivolumab) have also shown efficacy in other solid tumors such as non-small-cell lung cancer, and renal-cell cancer [Topalian et al. N Engl J Med. (2012) 366(26):2443-54].

4F-benzoyl-TN14003 (also known as BKT140, hereinafter BL-8040), is a 14-residue bio stable synthetic peptide developed as a specific CXCR4 antagonist. It has been shown that BL-8040 binds the CXCR4 receptor with high affinity and long receptor occupancy. Studies in mice demonstrated that a single BL-8040 injection mobilized long term repopulating stem cells sufficient for transplantation. [Abraham M et al., Stem Cells (2007); 25:2158-66] Results from a study in multiple myeloma patients showed that combined treatment of BL-8040 and G-CSF enabled the collection of high number of CD34+ hematopoietic stem/progenitor cells (HSPC) in a single aphaeresis procedure [Peled A et al. Clin Cancer Res; (2013) 20(2); 469-79].

In addition, BL-8040 was found to be toxic against several tumors such as myeloid leukemia, hematopoietic tumors and non-small cell lung cancer (International Patent Application No. IL2014/050939 and International Patent Application Publication Nos. WO2013/160895 and WO2008/075370.

Additional background art includes:
International Patent Application Publication No. WO2014/155376;
International Patent Application Publication No. WO2012/095849;
International Patent Application Publication No. WO2002/20561;
International Patent Application Publication No. WO2004/020462;
International Patent Application Publication No. WO2008/075369;
International Patent Application Publication No. WO2008/075371;
International Patent Application Publication No. WO2010/146578;
International Patent Application Publication No. WO2003/146584;
International Patent Application Publication No. WO2003/072599;
International Patent Application Publication No. WO2015/019284;
U.S. Patent Application Publication No. 2012/0082687; and
Chen et al. HEPATOLOGY (2015) 61: 1591-1602.

SUMMARY OF THE INVENTION

According to an aspect of some embodiments of the present invention there is provided a method of treating cancer in a subject in need thereof, the method comprising:

(a) administering to the subject a therapeutically effective amount of a peptide having an amino acid sequence as set forth in SEQ ID NO: 1 or an analog or derivative thereof; and (b) administering to the subject a therapeutically effective amount of a PD1 antagonist, thereby treating the cancer in the subject.

According to an aspect of some embodiments of the present invention there is provided a method of treating cancer in a subject in need thereof, the method comprising:

(a) administering to the subject a therapeutically effective amount of a peptide having an amino acid sequence as set forth in SEQ ID NO: 1 or an analog or derivative thereof; and (b) administering to the subject a therapeutically effective amount of a PD-L1 antagonist, thereby treating the cancer in the subject.

According to an aspect of some embodiments of the present invention there is provided a method of treating cancer in a subject in need thereof, the method comprising:

(a) administering to the subject a therapeutically effective amount of a peptide having an amino acid sequence as set forth in SEQ ID NO: 1 or an analog or derivative thereof; and (b) administering to the subject a therapeutically effective amount of a CTLA-4 antagonist, thereby treating the cancer in the subject.

According to an aspect of some embodiments of the present invention there is provided a method of treating cancer in a subject in need thereof, the method comprising:

(a) administering to the subject a therapeutically effective amount of a peptide having an amino acid sequence as set forth in SEQ ID NO: 1 or an analog or derivative thereof; and (b) administering to the subject a therapeutically effective amount of a LAG-3 antagonist, thereby treating the cancer in the subject.

According to an aspect of some embodiments of the present invention there is provided a method of treating cancer in a subject in need thereof, the method comprising:

(a) administering to the subject a therapeutically effective amount of a peptide having an amino acid sequence as set forth in SEQ ID NO: 1 or an analog or derivative thereof; and (b) administering to the subject a therapeutically effective amount of a TIM-3 antagonist, thereby treating the cancer in the subject.

According to an aspect of some embodiments of the present invention there is provided a method of treating cancer in a subject in need thereof, the method comprising:

(a) administering to the subject a therapeutically effective amount of a peptide having an amino acid sequence as set forth in SEQ ID NO: 1 or an analog or derivative thereof; and (b) administering to the subject a therapeutically effective amount of a KIR antagonist, thereby treating the cancer in the subject.

According to an aspect of some embodiments of the present invention there is provided a method of treating cancer in a subject in need thereof, the method comprising:

(a) administering to the subject a therapeutically effective amount of a peptide having an amino acid sequence as set forth in SEQ ID NO: 1 or an analog or derivative thereof; and (b) administering to the subject a therapeutically effective amount of a IDO antagonist, thereby treating the cancer in the subject.

According to an aspect of some embodiments of the present invention there is provided a method of treating cancer in a subject in need thereof, the method comprising:

(a) administering to the subject a therapeutically effective amount of a peptide having an amino acid sequence as set forth in SEQ ID NO: 1 or an analog or derivative thereof; and (b) administering to the subject a therapeutically effective amount of a OX40 agonist, thereby treating the cancer in the subject.

According to an aspect of some embodiments of the present invention there is provided a method of treating cancer in a subject in need thereof, the method comprising:

(a) administering to the subject a therapeutically effective amount of a peptide having an amino acid sequence as set forth in SEQ ID NO: 1 or an analog or derivative thereof; and (b) administering to the subject a therapeutically effective amount of a CD137 agonist, thereby treating the cancer in the subject.

According to an aspect of some embodiments of the present invention there is provided a method of treating cancer in a subject in need thereof, the method comprising:

(a) administering to the subject a therapeutically effective amount of a peptide having an amino acid sequence as set forth in SEQ ID NO: 1 or an analog or derivative thereof; and (b) administering to the subject a therapeutically effective amount of a CD27 agonist, thereby treating the cancer in the subject.

According to an aspect of some embodiments of the present invention there is provided a method of treating cancer in a subject in need thereof, the method comprising:

(a) administering to the subject a therapeutically effective amount of a peptide having an amino acid sequence as set forth in SEQ ID NO: 1 or an analog or derivative thereof; and (b) administering to the subject a therapeutically effective amount of a CD40 agonist, thereby treating the cancer in the subject.

According to an aspect of some embodiments of the present invention there is provided a method of treating cancer in a subject in need thereof, the method comprising:

(a) administering to the subject a therapeutically effective amount of a peptide having an amino acid sequence as set forth in SEQ ID NO: 1 or an analog or derivative thereof; and (b) administering to the subject a therapeutically effective amount of a GITR agonist, thereby treating the cancer in the subject.

According to an aspect of some embodiments of the present invention there is provided a method of treating cancer in a subject in need thereof, the method comprising:

(a) administering to the subject a therapeutically effective amount of a peptide having an amino acid sequence as set forth in SEQ ID NO: 1 or an analog or derivative thereof; and (b) administering to the subject a therapeutically effective amount of a CD28 agonist, thereby treating the cancer in the subject.

According to an aspect of some embodiments of the present invention there is provided a method of treating cancer in a subject in need thereof, the method comprising:

(a) administering to the subject a therapeutically effective amount of a peptide having an amino acid sequence as set forth in SEQ ID NO: 1 or an analog or derivative thereof; and (b) administering to the subject a therapeutically effective amount of a ICOS agonist, thereby treating the cancer in the subject.

According to some embodiments of the invention, the (a) is effected prior to (b).

According to some embodiments of the invention, the (a) is effected following (b).

According to some embodiments of the invention, the (a) is effected concomitantly with (b).

According to some embodiments of the invention, (a) is effected multiple times.

According to some embodiments of the invention, (b) is effected multiple times.

According to some embodiments of the invention, the (a) and the (b) are effected sequentially.

According to some embodiments of the invention, the (a) is effected at a dose of 0.5-1 mg/kg.

According to some embodiments of the invention, the (a) is administered subcutaneously.

According to an aspect of some embodiments of the present invention there is provided an article of manufacture identified for use in treating cancer, comprising a packaging material packaging a peptide having an amino acid sequence as set forth in SEQ ID NO: 1 or an analog or derivative thereof and a PD1 antagonist.

According to an aspect of some embodiments of the present invention there is provided an article of manufacture identified for use in treating cancer, comprising a packaging material packaging a peptide having an amino acid sequence as set forth in SEQ ID NO: 1 or an analog or derivative thereof and a PD-L1 antagonist.

According to an aspect of some embodiments of the present invention there is provided an article of manufacture identified for use in treating cancer, comprising a packaging material packaging a peptide having an amino acid sequence as set forth in SEQ ID NO: 1 or an analog or derivative thereof; and a CTLA-4 antagonist.

According to an aspect of some embodiments of the present invention there is provided an article of manufacture identified for use in treating cancer, comprising a packaging material packaging a peptide having an amino acid sequence as set forth in SEQ ID NO: 1 or an analog or derivative thereof and a LAG-3 antagonist.

According to an aspect of some embodiments of the present invention there is provided an article of manufacture identified for use in treating cancer, comprising a packaging material packaging a peptide having an amino acid sequence as set forth in SEQ ID NO: 1 or an analog or derivative thereof and a TIM-3 antagonist.

According to an aspect of some embodiments of the present invention there is provided an article of manufacture identified for use in treating cancer, comprising a packaging material packaging a peptide having an amino acid sequence as set forth in SEQ ID NO: 1 or an analog or derivative thereof and a KIR antagonist.

According to an aspect of some embodiments of the present invention there is provided an article of manufacture identified for use in treating cancer, comprising a packaging material packaging a peptide having an amino acid sequence as set forth in SEQ ID NO: 1 or an analog or derivative thereof and a IDO antagonist.

According to an aspect of some embodiments of the present invention there is provided an article of manufacture identified for use in treating cancer, comprising a packaging material packaging a peptide having an amino acid sequence as set forth in SEQ ID NO: 1 or an analog or derivative thereof and a OX40 agonist.

According to an aspect of some embodiments of the present invention there is provided an article of manufacture identified for use in treating cancer, comprising a packaging material packaging a peptide having an amino acid sequence as set forth in SEQ ID NO: 1 or an analog or derivative thereof and a CD137 agonist.

According to an aspect of some embodiments of the present invention there is provided an article of manufacture identified for use in treating cancer, comprising a packaging material packaging a peptide having an amino acid sequence as set forth in SEQ ID NO: 1 or an analog or derivative thereof and a CD27 agonist.

According to an aspect of some embodiments of the present invention there is provided an article of manufacture identified for use in treating cancer, comprising a packaging material packaging a peptide having an amino acid sequence as set forth in SEQ ID NO: 1 or an analog or derivative thereof and a CD40 agonist.

According to an aspect of some embodiments of the present invention there is provided an article of manufacture identified for use in treating cancer, comprising a packaging material packaging a peptide having an amino acid sequence as set forth in SEQ ID NO: 1 or an analog or derivative thereof and a GITR agonist.

According to an aspect of some embodiments of the present invention there is provided an article of manufacture identified for use in treating cancer, comprising a packaging material packaging a peptide having an amino acid sequence as set forth in SEQ ID NO: 1 or an analog or derivative thereof and a CD28 agonist.

According to an aspect of some embodiments of the present invention there is provided an article of manufacture identified for use in treating cancer, comprising a packaging material packaging a peptide having an amino acid sequence as set forth in SEQ ID NO: 1 or an analog or derivative thereof and a ICOS agonist.

According to some embodiments of the invention, the peptide and the antagonist are in separate formulations.

According to some embodiments of the invention, the peptide and the antagonist are in a co-formulation.

According to some embodiments of the invention, the peptide and the agonist are in separate formulations.

According to some embodiments of the invention, the peptide and the agonist are in a co-formulation.

According to an aspect of some embodiments of the present invention there is provided a pharmaceutical composition comprising as active ingredients a peptide having an amino acid sequence as set forth in SEQ ID NO: 1 or an analog or derivative thereof and a PD1 antagonist; and a pharmaceutically acceptable carrier or diluent.

According to an aspect of some embodiments of the present invention there is provided a pharmaceutical composition comprising as active ingredients a peptide having an amino acid sequence as set forth in SEQ ID NO: 1 or an analog or derivative thereof and a PD-L1 antagonist; and a pharmaceutically acceptable carrier or diluent.

According to an aspect of some embodiments of the present invention there is provided a pharmaceutical composition comprising as active ingredients a peptide having an amino acid sequence as set forth in SEQ ID NO: 1 or an analog or derivative thereof; and a CTLA-4 antagonist; and a pharmaceutically acceptable carrier or diluent.

According to an aspect of some embodiments of the present invention there is provided a pharmaceutical composition comprising as active ingredients a peptide having an amino acid sequence as set forth in SEQ ID NO: 1 or an analog or derivative thereof and a LAG-3 antagonist; and a pharmaceutically acceptable carrier or diluent.

According to an aspect of some embodiments of the present invention there is provided a pharmaceutical composition comprising as active ingredients a peptide having an amino acid sequence as set forth in SEQ ID NO: 1 or an analog or derivative thereof and a TIM-3 antagonist; and a pharmaceutically acceptable carrier or diluent.

According to an aspect of some embodiments of the present invention there is provided a pharmaceutical composition comprising as active ingredients a peptide having an amino acid sequence as set forth in SEQ ID NO: 1 or an analog or derivative thereof and a KIR antagonist; and a pharmaceutically acceptable carrier or diluent.

According to an aspect of some embodiments of the present invention there is provided a pharmaceutical composition comprising as active ingredients a peptide having an amino acid sequence as set forth in SEQ ID NO: 1 or an analog or derivative thereof and a IDO antagonist; and a pharmaceutically acceptable carrier or diluent.

According to an aspect of some embodiments of the present invention there is provided a pharmaceutical composition comprising as active ingredients a peptide having an amino acid sequence as set forth in SEQ ID NO: 1 or an analog or derivative thereof and a OX40 agonist; and a pharmaceutically acceptable carrier or diluent.

According to an aspect of some embodiments of the present invention there is provided a pharmaceutical composition comprising as active ingredients a peptide having an amino acid sequence as set forth in SEQ ID NO: 1 or an analog or derivative thereof and a CD137 agonist; and a pharmaceutically acceptable carrier or diluent.

According to an aspect of some embodiments of the present invention there is provided a pharmaceutical composition comprising as active ingredients a peptide having an amino acid sequence as set forth in SEQ ID NO: 1 or an analog or derivative thereof and a CD27 agonist; and a pharmaceutically acceptable carrier or diluent.

According to an aspect of some embodiments of the present invention there is provided a pharmaceutical composition comprising as active ingredients a peptide having an amino acid sequence as set forth in SEQ ID NO: 1 or an analog or derivative thereof and a CD40 agonist; and a pharmaceutically acceptable carrier or diluent.

According to an aspect of some embodiments of the present invention there is provided a pharmaceutical composition comprising as active ingredients a peptide having an amino acid sequence as set forth in SEQ ID NO: 1 or an analog or derivative thereof and a GITR agonist; and a pharmaceutically acceptable carrier or diluent.

According to an aspect of some embodiments of the present invention there is provided a pharmaceutical composition comprising as active ingredients a peptide having an amino acid sequence as set forth in SEQ ID NO: 1 or an analog or derivative thereof and a CD28 agonist; and a pharmaceutically acceptable carrier or diluent.

According to an aspect of some embodiments of the present invention there is provided a pharmaceutical composition comprising as active ingredients a peptide having an amino acid sequence as set forth in SEQ ID NO: 1 or an analog or derivative thereof and a ICOS agonist; and a pharmaceutically acceptable carrier or diluent.

According to some embodiments of the invention, the antagonist is an antibody.

According to some embodiments, the method of treating cancer further comprises administering a vaccine and optionally wherein the vaccine is an HPV vaccine.

According to some embodiments of the invention, the antagonist is a small molecule.

According to some embodiments of the invention, the antagonist is a peptide.

According to some embodiments of the invention, the agonist is an antibody.

According to some embodiments of the invention, the agonist is a small molecule.

According to some embodiments of the invention, the agonist is a peptide.

According to some embodiments of the invention, the analog or derivative has an amino acid sequence as set forth in formula (I) or a salt thereof:

1 2 3 4 5 6 7 8 9 10 11 12 13 14

$$A_1\text{-}A_2\text{-}A_3\text{-}Cys\text{-}Tyr\text{-}A_4\text{-}A_5\text{-}A_6\text{-}A_7\text{-}A_8\text{-}A_9\text{-}A_{10}\text{-}Cys\text{-}A_{11} \qquad (I)$$

wherein:

$A_1$ is an arginine, lysine, ornithine, citrulline, alanine or glutamic acid residue or a N-α-substituted derivative of these amino acids, or $A_1$ is absent;

$A_2$ represents an arginine or glutamic acid residue if $A_1$ is present, or $A_2$ represents an arginine or glutamic acid residue or a N-α-substituted derivative of these amino acids if $A_1$ is absent;

$A_3$ represents an aromatic amino acid residue;

$A_4$, $A_5$ and $A_9$ each independently represents an arginine, lysine, ornithine, citrulline, alanine or glutamic acid residue;

$A_6$ represents a proline, glycine, ornithine, lysine, alanine, citrulline, arginine or glutamic acid residue;

$A_7$ represents a proline, glycine, ornithine, lysine, alanine, citrulline or arginine residue;

$A_8$ represents a tyrosine, phenylalanine, alanine, naphthylalanine, citrulline or glutamic acid residue;

$A_{10}$ represents a citrulline, glutamic acid, arginine or lysine residue;

$A_{11}$ represents an arginine, glutamic acid, lysine or citrulline residue wherein the C-terminal carboxyl may be derivatized;

and the cysteine residue of the 4-position or the 13-position can form a disulfide bond, and the amino acids can be of either L or D form.

According to some embodiments of the invention, the peptide is selected from the group consisting of SEQ ID NOs: 1-72.

According to some embodiments of the invention, the peptide is as set forth in SEQ ID NO: 1.

According to some embodiments of the invention, the cancer is a solid tumor cancer.

According to some embodiments of the invention, the solid tumor is selected from the group consisting of lung cancer, glioma, colon cancer, ovarian cancer, renal cancer, melanoma cancer, hepatocellular cancer, gastric or stomach cancer, glioblastoma, cervical cancer, bladder cancer, breast cancer, colorectal cancer, prostate cancer, thyroid cancer, head and neck and pancreatic cancer.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

DESCRIPTION OF SPECIFIC EMBODIMENTS OF THE INVENTION

The present invention, in some embodiments thereof, relates to methods of treating cancer and, more particularly, but not exclusively, to the use of a CXCR4 antagonistic peptide and an immune-check point regulator in the treatment of cancer.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Treatment of most types of cancer involves cytotoxic treatments such as chemotherapy and radiotherapy that may at least in part affect many healthy cells and thus result in elevated toxicity. In addition, these treatments are effective in only a small percentage of cancer affected patients. Immunotherapy strategies for cancer therapy, aiming at harnessing the immune system to fight cancer, include cytokines, monoclonal antibodies against tumor cells or immune regulatory molecules, cancer vaccines as well as cell-based therapies such as adoptive transfer of ex-vivo activated T cells and natural killer (NK) cells.

4F-benzoyl-TN14003 (SEQ ID NO: 1, also known as BKT140, hereinafter BL-8040) is a CXCR4 peptide antagonist. It has been shown that BL-8040 induces mobilization of CD34+ hematopoietic stem/progenitor cells (HSPC) that can be further used for transplantation. In addition, BL-8040 was found to be toxic against several tumors such as myeloid leukemia, hematopoietic tumors and non-small cell lung cancer.

While reducing the present invention to practice, the present inventors have found that in-vivo administration of BL-8040 induces rapid mobilization of a variety of immune cells including immature stem/progenitor cells as well as fully differentiated T cells and NK cells. The present findings therefore can be harnessed to the use of BL-8040 to induce the mobilization and dissemination of ImDCs and T effector and memory cells into tumor sites and thus can augment the anti-tumor effect of immunotherapeutics.

Consequently, the present teachings and the protocols presented in Example 1, suggest the use of a peptide having an amino acid sequence as set forth in SEQ ID NO: 1 or an analog or derivative thereof in combination with several combinations of immune-check point regulators for the treatment of cancer.

The terms "treating" or "treatment" refers to inhibiting, preventing or arresting the development of a pathology (e.g. cancer) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein the phrase "subject in need thereof" refers to a mammalian male or female subject (e.g., human being) who is diagnosed with cancer. In a specific embodiment, this term encompasses individuals who are at risk to develop cancer. Veterinary uses are also contemplated. The subject may be of any gender or at any age including neonatal, infant, juvenile, adolescent, adult and elderly adult.

The terms "cancer" and "cancerous" refer to or describe the physiological condition in mammals that is typically characterized by unregulated cell growth.

Cancers which can be treated by the method of this aspect of some embodiments of the invention can be any solid or non-solid cancer and/or cancer metastasis.

According to a specific embodiment, the cancer is a solid tumor. According another specific embodiment, the cancer is a non-solid tumor.

Examples of cancer include but are not limited to, carcinoma, lymphoma, blastoma, sarcoma, and leukemia. More particular examples of such cancers include squamous cell cancer, lung cancer (including small-cell lung cancer, non-small-cell lung cancer, adenocarcinoma of the lung, and squamous carcinoma of the lung), melanoma cancer, cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high-grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; acute myeloblastic leukemia; Multiple Myeloma; and post-transplant lymphoproliferative disorder (PTLD), as well as abnormal vascular proliferation associated with phakomatoses, edema (such as that associated with brain tumors), and Meigs' syndrome. Preferably, the cancer is selected from the group consisting of breast cancer, colorectal cancer, rectal cancer, non-small cell lung cancer, non-Hodgkins lymphoma (NHL), acute lymphoblastic leukemia (ALL); chronic myeloblastic leukemia (CML); acute myeloblastic leukemia (AML); renal cell cancer, prostate cancer, liver cancer, pancreatic cancer, soft-tissue sarcoma, Kaposi's sarcoma, carcinoid carcinoma, head and neck cancer, melanoma, ovarian cancer, mesothelioma, and multiple myeloma. The cancerous conditions amenable for treatment of the invention include metastatic cancers.

According to specific embodiments the cancer is selected from the group consisting of lung cancer, glioma, colon cancer, ovarian cancer, renal cancer, melanoma cancer, hepatocellular cancer, gastric or stomach cancer, glioblastoma, cervical cancer, bladder cancer, breast cancer, colorectal cancer, prostate cancer, thyroid cancer, head and neck and pancreatic cancer.

According to specific embodiments, the cancer is selected from the group consisting of lung cancer, glioma, colon cancer and pancreatic cancer.

According to other specific embodiments, the cancer is selected from the group consisting of multiple myeloma and leukemia.

As used herein, the term "peptide" encompasses native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body or more capable of penetrating into cells.

According to a specific embodiment, the peptide is no more than 100 amino acids in length. According to a specific embodiment, the peptide is 5-100 amino acids in length. According to a specific embodiment, the peptide is 5-50 amino acids in length. According to a specific embodiment, the peptide is 5-20 amino acids in length. According to a specific embodiment, the peptide is 5-15 amino acids in length. According to a specific embodiment, the peptide is 10-20 amino acids in length. According to a specific embodiment, the peptide is 10-15 amino acids in length.

As used herein the term "peptide having an amino acid sequence as set forth in SEQ ID NO: 1 or an analog or derivative thereof" refers to 4F-benzoyl-TN14003 (SEQ ID NO: 1, also known as BKT140, hereinafter BL-8040) peptide and functional analogs or derivatives thereof. The peptides of the present invention are structurally and functionally related to the peptides disclosed in patent applications WO2002/020561 and WO2004/020462, also known as "T-140 analogs", as detailed hereinbelow. The peptide of the present invention is a CXCR4-antagnoistic peptide i.e. it reduces CXCR-4 activation by at least 10% as compared to same in the absence of the peptide antagonist. According to a specific embodiment the peptide antagonist is a competitive inhibitor. According to a specific embodiment the peptide antagonist is a non-competitive inhibitor.

According to specific embodiments, a functional CXCR4 antagonistic peptide, as used herein, is capable of inducing mobilization and dissemination of ImDCs, NK cells, B cells, monocytes/macrophages and T effector and memory cells into a tumor of a subject upon administration.

According to other specific embodiments, a functional CXCR4 antagonistic peptide, as used herein, is capable of enhancing an immune-response to a tumor.

In various particular embodiments, the peptide analog or derivative has an amino acid sequence as set forth in the following formula (I) or a salt thereof:

1 2 3 4 5 6 7 8 9 10 11 12 13 14

$A_1$-$A_2$-$A_3$-Cys-Tyr-$A_4$-$A_5$-$A_6$-$A_7$-$A_8$-$A_9$-$A_{10}$-Cys-$A_{11}$    (I)

wherein:

$A_1$ is an arginine, lysine, ornithine, citrulline, alanine or glutamic acid residue or a N-α-substituted derivative of these amino acids, or $A_1$ is absent;

$A_2$ represents an arginine or glutamic acid residue if $A_1$ is present, or $A_2$ represents an arginine or glutamic acid residue or a N-α-substituted derivative of these amino acids if $A_1$ is absent;

$A_3$ represents an aromatic amino acid residue;

$A_4$, $A_5$ and $A_9$ each independently represents an arginine, lysine, omithine, citrulline, alanine or glutamic acid residue;

$A_6$ represents a proline, glycine, omithine, lysine, alanine, citrulline, arginine or glutamic acid residue;

$A_7$ represents a proline, glycine, ornithine, lysine, alanine, citrulline or arginine residue;

$A_8$ represents a tyrosine, phenylalanine, alanine, naphthylalanine, citrulline or glutamic acid residue;

$A_{10}$ represents a citrulline, glutamic acid, arginine or lysine residue;

$A_{11}$ represents an arginine, glutamic acid, lysine or citrulline residue wherein the C-terminal carboxyl may be derivatized;

and the cysteine residue of the 4-position or the 13-position can form a disulfide bond, and the amino acids can be of either L or D form.

Exemplary peptides according to formula (I) are peptides having an amino acid sequence as set forth in any one of SEQ ID NOs: 1-72, as presented in Table 1 hereinbelow.

TABLE 1

| T-140 and currently preferred T-140 analogs | | |
|---|---|---|
| Analog | SEQ ID NO: | Amino acid sequence |
| 4F-benzoyl-TN14003 | 1 | 4F-benzoyl-Arg-Arg-Nal-Cys-Tyr-Cit-Lys-DLys-Pro-Tyr-Arg-Cit-Cys-Arg-NH$_2$ |
| AcTC14003 | 2 | Ac-Arg-Arg-Nal-Cys-Tyr-Cit-Lys-DLys-Pro-Tyr-Arg-Cit-Cys-Arg-OH |
| AcTC14005 | 3 | Ac-Arg-Arg-Nal-Cys-Tyr-Arg-Lys-DCit-Pro-Tyr-Arg-Cit-Cys-Arg-OH |
| AcTC14011 | 4 | Ac-Arg-Arg-Nal-Cys-Tyr-Cit-Lys-DCit-Pro-Tyr-Arg-Cit-Cys-Arg-OH |
| AcTC14013 | 5 | Ac-Arg-Arg-Nal-Cys-Tyr-Cit-Lys-DLys-Pro-Tyr-Cit-Cit-Cys-Arg-OH |
| AcTC14015 | 6 | Ac-Cit-Arg-Nal-Cys-Tyr-Cit-Lys-DLys-Pro-Tyr-Arg-Cit-Cys-Arg-OH |
| AcTC14017 | 7 | Ac-Cit-Arg-Nal-Cys-Tyr-Arg-Lys-DCit-Pro-Tyr-Arg-Cit-Cys-Arg-OH |
| AcTC14019 | 8 | Ac-Arg-Arg-Nal-Cys-Tyr-Arg-Lys-DCit-Pro-Tyr-Cit-Cit-Cys-Arg-OH |
| AcTC14021 | 9 | Ac-Cit-Arg-Nal-Cys-Tyr-Arg-Lys-DLys-Pro-Tyr-Cit-Cit-Cys-Arg-OH |
| AcTC14012 | 10 | Ac-Arg-Arg-Nal-Cys-Tyr-Cit-Lys-DCit-Pro-Tyr-Arg-Cit-Cys-Arg-NH$_2$ |
| AcTC14014 | 11 | Ac-Arg-Arg-Nal-Cys-Tyr-Cit-Lys-DLys-Pro-Tyr-Cit-Cit-Cys-Arg-NH$_2$ |
| AcTC14016 | 12 | Ac-Cit-Arg-Nal-Cys-Tyr-Cit-Lys-DLys-Pro-Tyr-Arg-Cit-Cys-Arg-NH$_2$ |
| AcTC14018 | 13 | Ac-Cit-Arg-Nal-Cys-Tyr-Arg-Lys-DCit-Pro-Tyr-Arg-Cit-Cys-Arg-NH$_2$ |
| AcTC14020 | 14 | Ac-Arg-Arg-Nal-Cys-Tyr-Arg-Lys-DCit-Pro-Tyr-Cit-Cit-Cys-Arg-NH$_2$ |
| AcTC14022 | 15 | Ac-Cit-Arg-Nal-Cys-Tyr-Arg-Lys-DLys-Pro-Tyr-Cit-Cit-Cys-Arg-NH$_2$ |
| TE14001 | 16 | H-DGlu-Arg-Nal-Cys-Tyr-Arg-Lys-DLys-Pro-Tyr-Arg-Cit-Cys-Arg-OH |
| TE14002 | 17 | H-Arg-Glu-Nal-Cys-Tyr-Arg-Lys-DLys-Pro-Tyr-Arg-Cit-Cys-Arg-OH |
| TE14003 | 18 | H-Arg-Arg-Nal-Cys-Tyr-Glu-Lys-DLys-Pro-Tyr-Arg-Cit-Cys-Arg-OH |
| TE14004 | 19 | H-Arg-Arg-Nal-Cys-Tyr-Arg-Glu-DLys-Pro-Tyr-Arg-Cit-Cys-Arg-OH |

TABLE 1-continued

T-140 and currently preferred T-140 analogs

| Analog | SEQ ID NO: | Amino acid sequence |
|---|---|---|
| TE14005 | 20 | H-Arg-Arg-Nal-Cys-Tyr-Arg-Lys-DGlu-Pro-Tyr-Arg-Cit-Cys-Arg-OH |
| TE14006 | 21 | H-Arg-Arg-Nal-Cys-Tyr-Arg-Lys-DLys-Pro-Tyr-Glu-Cit-Cys-Arg-OH |
| TE14007 | 22 | H-Arg-Arg-Nal-Cys-Tyr-Arg-Lys-DLys-Pro-Tyr-Arg-Cit-Cys-Glu-OH |
| TE14011 | 23 | H-Arg-Arg-Nal-Cys-Tyr-Cit-Lys-DGlu-Pro-Tyr-Arg-Cit-Cys-Arg-NH$_2$ |
| TE14012 | 24 | H-Arg-Arg-Nal-Cys-Tyr-DGlu-Lys-DCit-Pro-Tyr-Arg-Cit-Cys-Arg-NH$_2$ |
| TE14013 | 25 | H-Arg-Arg-Nal-Cys-Tyr-DGlu-Lys-DGlu-Pro-Tyr-Arg-Cit-Cys-Arg-NH$_2$ |
| TE14014 | 26 | H-DGlu-Arg-Nal-Cys-Tyr-Cit-Lys-DGlu-Pro-Tyr-Arg-Cit-Cys-Arg-NH$_2$ |
| TE14015 | 27 | H-Arg-Arg-Nal-Cys-Tyr-Cit-Lys-DGlu-Pro-DGlu-Arg-Cit-Cys-Arg-NH$_2$ |
| TE14016 | 28 | H-Arg-Arg-Nal-Cys-Tyr-Cit-Lys-DGlu-Pro-Tyr-Arg-DGlu-Cys-Arg-NH$_2$ |
| AcTE14014 | 29 | Ac-DGlu-Arg-Nal-Cys-Tyr-Cit-Lys-DGlu-Pro-Tyr-Arg-Cit-Cys-Arg-NH$_2$ |
| AcTE14015 | 30 | Ac-Arg-Arg-Nal-Cys-Tyr-Cit-Lys-DGlu-Pro-DGlu-Arg-Cit-Cys-Arg-NH$_2$ |
| AcTE14016 | 31 | Ac-Arg-Arg-Nal-Cys-Tyr-Cit-Lys-DGlu-Pro-Tyr-Arg-DGlu-Cys-Arg-NH$_2$ |
| TF1: AcTE14011 | 32 | Ac-Arg-Arg-Nal-Cys-Tyr-Cit-Lys-DGlu-Pro-Tyr-Arg-Cit-Cys-Arg-NH$_2$ |
| TF2: guanyl-TE14011 | 33 | guanyl-Arg-Arg-Nal-Cys-Tyr-Cit-Lys-DGlu-Pro-Tyr-Arg-Cit-Cys-Arg-NH$_2$ |
| TF3: TMguanyl-TE14011 | 34 | TMguanyl-Arg-Arg-Nal-Cys-Tyr-Cit-Lys-DGlu-Pro-Tyr-Arg-Cit-Cys-Arg-NH$_2$ |
| TF4: TMguanyl-TE14011 (2-14) | 35 | TMguanyl-Arg-Nal-Cys-Tyr-Cit-Lys-DGlu-Pro-Tyr-Arg-Cit-Cys-Arg-NH$_2$ |
| TF5: 4F-benzoyl-TE14011 | 36 | 4F-benzoyl-Arg-Arg-Nal-Cys-Tyr-Cit-Lys-DGlu-Pro-Tyr-Arg-Cit-Cys-Arg-NH$_2$ |
| TF6: 2F-benzoyl-TE14011 | 37 | 2F-benzoyl-Arg-Arg-Nal-Cys-Tyr-Cit-Lys-DGlu-Pro-Tyr-Arg-Cit-Cys-Arg-NH$_2$ |
| TF7: APA-TE14011 (2-14) | 38 | APA-Arg-Nal-Cys-Tyr-Cit-Lys-DGlu-Pro-Tyr-Arg-Cit-Cys-Arg-NH$_2$ |
| TF8: desamino-R-TE14011 (2-14) | 39 | desamino-R-Arg-Nal-Cys-Tyr-Cit-Lys-DGlu-Pro-Tyr-Arg-Cit-Cys-Arg-NH$_2$ |
| TF9: guanyl-TE14011 (2-14) | 40 | Guanyl-Arg-Nal-Cys-Tyr-Cit-Lys-DGlu-Pro-Tyr-Arg-Cit-Cys-Arg-NH$_2$ |
| TF10: succinyl-TE14011 (2-14) | 41 | succinyl-Arg-Nal-Cys-Tyr-Cit-Lys-DGlu-Pro-Tyr-Arg-Cit-Cys-Arg-NH$_2$ |
| TF11: glutaryl-TE14011 (2-14) | 42 | glutaryl-Arg-Nal-Cys-Tyr-Cit-Lys-DGlu-Pro-Tyr-Arg-Cit-Cys-Arg-NH$_2$ |
| TF12: deaminoTMG-APA-TE14011 (2-14) | 43 | deaminoTMG-APA-Arg-Nal-Cys-Tyr-Cit-Lys-DGlu-Pro-Tyr-Arg-Cit-Cys-Arg-NH$_2$ |
| TF15: H-Arg-CH2NH-RTE14011 (2-14) | 44 | R-CH2-Arg-Nal-Cys-Tyr-Cit-Lys-DGlu-Pro-Tyr-Arg-Cit-Cys-Arg-NH$_2$ |
| TF17: TE14011 (2-14) | 45 | H-Arg-Nal-Cys-Tyr-Cit-Lys-DGlu-Pro-Tyr-Arg-Cit-Cys-Arg-NH$_2$ |

TABLE 1-continued

T-140 and currently preferred T-140 analogs

| Analog | SEQ ID NO: | Amino acid sequence |
|---|---|---|
| TF18: TMguanyl-TC14012 | 46 | TMguanyl-Arg-Arg-Nal-Cys-Tyr-Cit-Lys-DCit-Pro-Tyr-Arg-Cit-Cys-Arg-NH$_2$ |
| TF19: ACA-TC14012 | 47 | ACA-Arg-Arg-Nal-Cys-Tyr-Cit-Lys-DCit-Pro-Tyr-Arg-Cit-Cys-Arg-NH$_2$ |
| TF20: ACA-T140 | 48 | ACA-Arg-Arg-Nal-Cys-Tyr-Arg-Lys-DLys-Pro-Tyr-Arg-Cit-Cys-Arg-OH |
| TZ14011 | 49 | H-Arg-Arg-Nal-Cys-Tyr-Cit-Arg-DLys-Pro-Tyr-Arg-Cit-Cys-Arg-NH$_2$ |
| AcTZ14011 | 50 | Ac-Arg-Arg-Nal-Cys-Tyr-Cit-Arg-DLys-Pro-Tyr-Arg-Cit-Cys-Arg-NH$_2$ |
| AcTN14003 | 51 | Ac-Arg-Arg-Nal-Cys-Tyr-Cit-Lys-DLys-Pro-Tyr-Arg-Cit-Cys-Arg-NH$_2$ |
| AcTN14005 | 52 | Ac-Arg-Arg-Nal-Cys-Tyr-Arg-Lys-DCit-Pro-Tyr-Arg-Cit-Cys-Arg-NH$_2$ |
| 4F-benzoyl-TN14011-Me | 53 | 4F-benzoyl-Arg-Arg-Nal-Cys-Tyr-Cit-Lys-DGlu-Pro-Tyr-Arg-Cit-Cys-Arg-NHMe |
| 4F-benzoyl-TN14011-Et | 54 | 4F-benzoyl-Arg-Arg-Nal-Cys-Tyr-Cit-Lys-DGlu-Pro-Tyr-Arg-Cit-Cys-Arg-NHEt |
| 4F-benzoyl-TN14011-iPr | 55 | 4F-benzoyl-Arg-Arg-Nal-Cys-Tyr-Cit-Lys-DGlu-Pro-Tyr-Arg-Cit-Cys-Arg-NHiPr |
| 4F-benzoyl-TN14011-tyramine | 56 | 4F-benzoyl-Arg-Arg-Nal-Cys-Tyr-Cit-Lys-DGlu-Pro-Tyr-Arg-Cit-Cys-Arg-tyramine |
| TA14001 | 57 | H-Ala-Arg-Nal-Cys-Tyr-Arg-Lys-DLys-Pro-Tyr-Arg-Cit-Cys-Arg-OH |
| TA14005 | 58 | H-Arg-Arg-Nal-Cys-Tyr-Ala-Lys-DLys-Pro-Tyr-Arg-Cit-Cys-Arg-OH |
| TA14006 | 59 | H-Arg-Arg-Nal-Cys-Tyr-Arg-Ala-DLys-Pro-Tyr-Arg-Cit-Cys-Arg-OH |
| TA14007 | 60 | H-Arg-Arg-Nal-Cys-Tyr-Arg-Lys-DAla-Pro-Tyr-Arg-Cit-Cys-Arg-OH |
| TA14008 | 61 | H-Arg-Arg-Nal-Cys-Tyr-Arg-Lys-DLys-Ala-Tyr-Arg-Cit-Cys-Arg-OH |
| TA14009 | 62 | H-Arg-Arg-Nal-Cys-Tyr-Arg-Lys-DLys-Pro-Ala-Arg-Cit-Cys-Arg-OH |
| TA14010 | 63 | H-Arg-Arg-Nal-Cys-Tyr-Arg-Lys-DLys-Pro-Tyr-Ala-Cit-Cys-Arg-OH |
| TC14001 | 64 | H-Cit-Arg-Nal-Cys-Tyr-Arg-Lys-DLys-Pro-Tyr-Arg-Cit-Cys-Arg-OH |
| TC14003 | 65 | H-Arg-Arg-Nal-Cys-Tyr-Cit-Lys-DLys-Pro-Tyr-Arg-Cit-Cys-Arg-OH |
| TN14003 | 66 | H-Arg-Arg-Nal-Cys-Tyr-Cit-Lys-DLys-Pro-Tyr-Arg-Cit-Cys-Arg-NH$_2$ |
| TC14004 | 67 | H-Arg-Arg-Nal-Cys-Tyr-Arg-Cit-DLys-Pro-Tyr-Arg-Cit-Cys-Arg-OH |
| TC14012 | 68 | H-Arg-Arg-Nal-Cys-Tyr-Cit-Lys-DCit-Pro-Tyr-Arg-Cit-Cys-Arg-NH$_2$ |
| T-140 | 69 | H-Arg-Arg-Nal-Cys-Tyr-Arg-Lys-DLys-Pro-Tyr-Arg-Cit-Cys-Arg-OH |
| TC14011 | 70 | H-Arg-Arg-Nal-Cys-Tyr-Cit-Lys-DCit-Pro-Tyr-Arg-Cit-Cys-Arg-OH |
| TC14005 | 71 | H-Arg-Arg-Nal-Cys-Tyr-Arg-Lys-DCit-Pro-Tyr-Arg-Cit-Cys-Arg-OH |
| TC14018 | 72 | H-Cit-Arg-Nal-Cys-Tyr-Arg-Lys-DCit-Pro-Tyr-Arg-Cit-Cys-Arg-NH$_2$ |

According to a specific embodiment, in each one of SEQ ID NOs: 1-72, two cysteine residues are coupled in a disulfide bond.

In another embodiment, the analog or derivative has an amino acid sequence as set forth in SEQ ID NO: 65 (H-Arg-Arg-Nal-Cys-Tyr-Cit-Lys-DLys-Pro-Tyr-Arg-Cit-Cys-Arg-OH; TC14003).

In another embodiment, the peptide used in the compositions and methods of the invention consists essentially of an amino acid sequence as set forth in SEQ ID NO: 1. In another embodiment, the peptide used in the compositions and methods of the invention comprises an amino acid sequence as set forth in SEQ ID NO: 1. In another embodiment, the peptide is at least 60%, at least 70% or at least 80% homologous to SEQ ID NO: 1. In another embodiment, the peptide is at least 90% homologous to SEQ ID NO: 1. In another embodiment, the peptide is at least about 95% homologous to SEQ ID NO: 1. Each possibility represents a separate embodiment of the present invention.

In various other embodiments, the peptide is selected from SEQ ID NOs: 1-72, wherein each possibility represents a separate embodiment of the present invention.

In another embodiment, the peptide has an amino acid sequence as set forth in any one of SEQ ID NOs: 1-4, 10, 46, 47, 51-56, 65, 66, 68, 70 and 71. In another embodiment, the peptide has an amino acid sequence as set forth in any one of SEQ ID NOs: 4, 10, 46, 47, 68 and 70. In another embodiment, the peptide has an amino acid sequence as set forth in any one of SEQ ID NOs: 1, 2, 51, 65 and 66. In another embodiment, the peptide has an amino acid sequence as set forth in any one of SEQ ID NOs: 53-56.

In an embodiment, the peptide has an amino acid sequence as set forth in SEQ ID NO: 1. According to a specific embodiment, the peptide is as set forth in SEQ ID NO: 1. In another embodiment, the peptide has an amino acid sequence as set forth in SEQ ID NO: 2. In another embodiment, the peptide has an amino acid sequence as set forth in SEQ ID NO: 51. In another embodiment, the peptide has an amino acid sequence as set forth in SEQ ID NO: 66.

According to a specific embodiment the peptide is as set forth in SEQ ID NO: 1 and any embodiment described herein should be read as if specifically reading over this peptide.

The peptides of some embodiments of the invention may be synthesized by any techniques that are known to those skilled in the art of peptide synthesis. For solid phase peptide synthesis, a summary of the many techniques may be found in J. M. Stewart and J. D. Young, Solid Phase Peptide Synthesis, W. H. Freeman Co. (San Francisco), 1963 and J. Meienhofer, Hormonal Proteins and Peptides, vol. 2, p. 46, Academic Press (New York), 1973. For classical solution synthesis see G. Schroder and K. Lupke, The Peptides, vol. 1, Academic Press (New York), 1965.

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then be attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final peptide compound. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide and so forth. Further description of peptide synthesis is disclosed in U.S. Pat. No. 6,472,505.

Large scale peptide synthesis is described by Andersson Biopolymers 2000; 55(3):227-50.

According to specific embodiments, the CXCR4 antagonistic peptide is administered to the subject in combination with one or more white blood cell mobilizing agents. For example, the peptide may be administered in sequential or concomitant combination with one or more other growth factors or cytokines that affect mobilization such as, but not limited to, G-CSF, GM-CSF and SCF.

As used herein the term "immune-check point regulator" refers to a molecule that modulates the activity of one or more immune-check point proteins in an agonistic or antagonistic manner resulting in recruitment of an immune cell to elicit an immune activity against a cancer cell.

According to specific embodiments, the immune-check point regulator modulates the activity of a specific immune-check point protein with no cross reactivity with other immune-check point proteins.

According to other specific embodiments, the immune-check point regulator modulates the activity of at least 2, at least 3, at least 4 immune-check point proteins.

According to specific embodiments the immune-check point regulator binds directly the immune-check point protein.

According to other specific embodiments, the immune-check point regulator indirectly binds the immune-check point protein through an intermediary molecule.

As used herein the term "activation" refers to the process of stimulating an immune cell (e.g. T cell, NK cell, B cell) that results in cellular proliferation, maturation, cytokine production and/or induction of regulatory or effector functions.

As used herein the term "immune-check point protein" refers to an antigen independent protein that modulates an immune cell response (i.e. activation or function). Immune-check point proteins can be either co-stimulatory proteins [i.e. positively regulating an immune cell activation or function by transmitting a co-stimulatory secondary signal resulting in activation of an immune cell] or inhibitory proteins (i.e. negatively regulating an immune cell activation or function by transmitting an inhibitory signal resulting in suppressing activity of an immune cell).

According to specific embodiments, the immune-check point protein regulates activation or function of a T cell. Numerous checkpoint proteins are known in the art and include, but not limited to, PD1, PDL-1, CTLA-4, CD80, LAG-3, TIM-3, KIR, IDO, OX40, OX40L, CD137 (4-1BB), 4-1BBL, CD27, CD70, CD40, CD40L, GITR, CD28, CD86, and ICOS (CD278), ICOSL.

Methods of determining signaling of a stimulatory or inhibitory signal are well known in the art and include, but are not limited to, binding assay using e.g. BiaCore, HPLC or flow cytometry, enzymatic activity assays such as kinase activity assays, and expression of molecules involved in the signaling cascade using e.g. PCR, Western blot, immunoprecipitation and immunohistochemistry. Additionally or alternatively, determining transmission of a signal (co-stimulatory or inhibitory) can be effected by evaluating immune cell activation or function. Methods of evaluating immune cell activation or function are well known in the art and include, but are not limited to, proliferation assays such as BRDU and thymidine incorporation, cytotoxicity assays such as chromium release, cytokine secretion assays such as intracellular cytokine staining ELISPOT and ELISA, expression of activation markers such as CD25, CD69 and CD69 using flow cytometry.

According to specific embodiments, determining the signaling activity is effected in-vitro or ex-vivo e.g. in a mixed lymphocyte reaction (MLR).

For the same culture conditions the signaling activity or the immune cell activation or function are generally expressed in comparison to the signaling, activation or function in a cell of the same species but not contacted with the immune-check point regulator or contacted with a vehicle control, also referred to as control.

Depending on the immune-check point protein (i.e. co-stimulatory or inhibitory) the immune-check point regulator can be an agonist or antagonist.

According to specific embodiment the immune-check point regulator is an antagonist.

As used herein the term "antagonist" refers to a molecule that prevents and/or inhibits the biological function and/or expression of an immune-check point protein.

According to specific embodiments, the antagonist prevents and/or inhibits the suppressive effect of an immune-check point protein on an immune cell (e.g. T cells).

According to specific embodiments, the antagonist prevents and/or inhibits signaling to an immune cell (e.g. T cell) by an immune-check point protein.

The molecule may be a reversible or an irreversible antagonist.

According to specific embodiments, the antagonist completely prevents the biological function (e.g. signal transduction) of the immune-check point protein.

According to other specific embodiments, the antagonist inhibits the biological function (e.g. signal transduction) of the immune-check point protein e.g., as detected by e.g. kinase activity, proliferation assay, cytotoxicity assay or cytokine secretion assay. The reduction may be by at least a 10%, at least 20%, at least 30%, at least 40%, at least 50%, at least 60%, at least 70%, at least 80%, at least 90%, at least 95% or at least 99% as compared to same in the absence of the antagonist.

Preventing and/or inhibiting the biological function of an immune-check point protein can be effected at the protein level (e.g., antibodies, small molecules, inhibitory peptides, enzymes that cleave the polypeptide, aptamers and the like) but may also be effected at the genomic (e.g. homologous recombination and site specific endonucleases) and/or the transcript level using a variety of molecules which interfere with transcription and/or translation (e.g., RNA silencing agents) of an inhibitory immune-check point protein.

Non limiting examples of agents that can function as antagonists are described in details hereinbelow.

Suppressing Biological Function at the Polypeptide Level

According to specific embodiments, the antagonistic agent is an antibody.

According to specific embodiments the antagonistic antibody is capable of specifically binding an inhibitory immune-check point protein. According to specific embodiments, the antagonistic antibody specifically binds at least one epitope of an inhibitory immune-check point protein.

As used herein, the term "epitope" refers to any antigenic determinant on an antigen to which the paratope of an antibody binds. Epitopic determinants usually consist of chemically active surface groupings of molecules such as amino acids or carbohydrate side chains and usually have specific three dimensional structural characteristics, as well as specific charge characteristics.

The term "antibody" as used in this invention includes intact molecules as well as functional fragments thereof, such as Fab, F(ab')2, Fv, scFv, dsFv, or single domain molecules such as VH and VL that are capable of binding to an epitope of an antigen.

The antibody may be mono-specific (capable of recognizing one epitope or protein), bi-specific (capable of binding two epitopes or proteins) or multi-specific (capable of recognizing multiple epitopes or proteins).

Suitable antibody fragments for practicing some embodiments of the invention include a complementarity-determining region (CDR) of an immunoglobulin light chain (referred to herein as "light chain"), a complementarity-determining region of an immunoglobulin heavy chain (referred to herein as "heavy chain"), a variable region of a light chain, a variable region of a heavy chain, a light chain, a heavy chain, an Fd fragment, and antibody fragments comprising essentially whole variable regions of both light and heavy chains such as an Fv, a single chain Fv Fv (scFv), a disulfide-stabilized Fv (dsFv), an Fab, an Fab', and an F(ab')2.

As used herein, the terms "complementarity-determining region" or "CDR" are used interchangeably to refer to the antigen binding regions found within the variable region of the heavy and light chain polypeptides. Generally, antibodies comprise three CDRs in each of the VH (CDR HI or HI; CDR H2 or H2; and CDR H3 or H3) and three in each of the VL (CDR LI or LI; CDR L2 or L2; and CDR L3 or L3).

The identity of the amino acid residues in a particular antibody that make up a variable region or a CDR can be determined using methods well known in the art and include methods such as sequence variability as defined by Kabat et al. (See, e.g., Kabat et al., 1992, Sequences of Proteins of Immunological Interest, 5th ed., Public Health Service, NIH, Washington D.C.), location of the structural loop regions as defined by Chothia et al. (see, e.g., Chothia et al., Nature 342:877-883, 1989.), a compromise between Kabat and Chothia using Oxford Molecular's AbM antibody modeling software (now Accelrys®, see, Martin et al., 1989, Proc. Natl Acad Sci USA. 86:9268; and world wide web site www(dot)bioinf-org(dot)uk/abs), available complex crystal structures as defined by the contact definition (see MacCallum et al., J. Mol. Biol. 262:732-745, 1996), the "conformational definition" (see, e.g., Makabe et al., Journal of Biological Chemistry, 283:1156-1166, 2008) and IMGT [Lefranc M P, et al. (2003) IMGT unique numbering for immunoglobulin and T cell receptor variable domains and Ig superfamily V-like domains. Dev Comp Immunol 27: 55-77].

As used herein, the "variable regions" and "CDRs" may refer to variable regions and CDRs defined by any approach known in the art, including combinations of approaches.

Functional antibody fragments comprising whole or essentially whole variable regions of both light and heavy chains are defined as follows:

(i) Fv, defined as a genetically engineered fragment consisting of the variable region of the light chain (VL) and the variable region of the heavy chain (VH) expressed as two chains;

(ii) single chain Fv ("scFv"), a genetically engineered single chain molecule including the variable region of the light chain and the variable region of the heavy chain, linked by a suitable polypeptide linker as a genetically fused single chain molecule;

(iii) disulfide-stabilized Fv ("dsFv"), a genetically engineered antibody including the variable region of the light chain and the variable region of the heavy chain, linked by a genetically engineered disulfide bond;

(iv) Fab, a fragment of an antibody molecule containing a monovalent antigen-binding portion of an antibody molecule which can be obtained by treating whole antibody with the enzyme papain to yield the intact light chain and the Fd fragment of the heavy chain which consists of the variable and CH1 domains thereof;

(v) Fab', a fragment of an antibody molecule containing a monovalent antigen-binding portion of an antibody molecule which can be obtained by treating whole antibody with the enzyme pepsin, followed by reduction (two Fab' fragments are obtained per antibody molecule);

(vi) F(ab')2, a fragment of an antibody molecule containing a monovalent antigen-binding portion of an antibody molecule which can be obtained by treating whole antibody with the enzyme pepsin (i.e., a dimer of Fab' fragments held together by two disulfide bonds); and (vii) Single domain antibodies or nanobodies are composed of a single VH or VL domains which exhibit sufficient affinity to the antigen.

The antibody may be monoclonal or polyclonal.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to some embodiments of the invention can be prepared by proteolytic hydrolysis of the antibody or by expression in $E.$ $coli$ or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as $E.$ $coli$. The recombinant host cells synthesize a single polypeptide chain with a linker peptide bridging the two V domains. Methods for producing sFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

It will be appreciated that for human therapy or diagnostics, humanized antibodies are preferably used. Humanized forms of non-human (e.g., murine) antibodies are chimeric molecules of immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art.

Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat.

Nos. 5,545,807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

Once antibodies are obtained, they may be tested for activity, for example via ELISA.

Another agent which can be used as antagonist with some embodiments of the invention is an aptamer. As used herein, the term "aptamer" refers to double stranded or single stranded RNA molecule that binds to specific molecular target, such as a protein. Various methods are known in the art which can be used to design protein specific aptamers. The skilled artisan can employ SELEX (Systematic Evolution of Ligands by Exponential Enrichment) for efficient selection as described in Stoltenburg R, Reinemann C, and Strehlitz B (Biomolecular engineering (2007) 24(4):381-403).

Another agent capable of being an antagonist would be any molecule which interferes with the immune-check point protein function (e.g. catalytic or interaction) by binding to and/or cleaving the immune-check point protein. Such molecules can be, but are not limited to, small molecules, inhibitory peptides, enzymes that cleave the immune-check point protein, adnectins, affibodies, avimers, anticalins, tetranectins, DARPins, and engineered Kunitz-type inhibitors wherein each possibility is a separate embodiment of the invention.

According to a specific embodiment, the antagonist is a small molecule.

According to a specific embodiment, the antagonist is a peptide molecule.

It will be appreciated that a non-functional analogue of at least a catalytic or binding portion of an inhibitory peptide can be also used as an antagonist.

Suppressing Biological Function at the Nucleic Acid Level

Down-regulation at the nucleic acid level is typically effected using a nucleic acid agent, having a nucleic acid backbone, DNA, RNA, mimetics thereof or a combination of same. The nucleic acid agent may be encoded from a DNA molecule or provided to the cell per se.

Thus, the antagonist of some embodiments of the invention can be an RNA silencing agent. As used herein, the phrase "RNA silencing" refers to a group of regulatory mechanisms [e.g. RNA interference (RNAi), transcriptional gene silencing (TGS), post-transcriptional gene silencing (PTGS), quelling, co-suppression, and translational repression] mediated by RNA molecules which result in the inhibition or "silencing" of the expression of a corresponding protein-coding gene. RNA silencing has been observed in many types of organisms, including plants, animals, and fungi.

As used herein, the term "RNA silencing agent" refers to an RNA which is capable of specifically inhibiting or "silencing" the expression of a target gene. In certain embodiments, the RNA silencing agent is capable of preventing complete processing (e.g., the full translation and/or expression) of an mRNA molecule through a post-transcriptional silencing mechanism. RNA silencing agents include non-coding RNA molecules, for example RNA duplexes comprising paired strands, as well as precursor RNAs from which such small non-coding RNAs can be generated. Exemplary RNA silencing agents include dsRNAs such as siRNAs, miRNAs and shRNAs.

In one embodiment, the RNA silencing agent is capable of inducing RNA interference.

In another embodiment, the RNA silencing agent is capable of mediating translational repression.

According to an embodiment of the invention, the RNA silencing agent is specific to the target RNA (i.e. an immune-check point e.g. PD-1, PDL-1, CTLA-4, LAG-3, TIM-3, KIR and IDO) and does not cross inhibit or silence other targets or a splice variant which exhibits 99% or less global homology to the target gene, e.g., less than 98%, 97%, 96%, 95%, 94%, 93%, 92%, 91%, 90%, 89%, 88%, 87%, 86%, 85%, 84%, 83%, 82%, 81% global homology to the target gene; as determined by PCR, Western blot, Immunohistochemistry and/or flow cytometry.

RNA interference refers to the process of sequence-specific post-transcriptional gene silencing in animals mediated by short interfering RNAs (siRNAs).

Following is a detailed description on RNA silencing agents that can be used according to specific embodiments of the present invention.

DsRNA, siRNA and shRNA—The presence of long dsRNAs in cells stimulates the activity of a ribonuclease III enzyme referred to as dicer. Dicer is involved in the processing of the dsRNA into short pieces of dsRNA known as short interfering RNAs (siRNAs). Short interfering RNAs derived from dicer activity are typically about 21 to about 23 nucleotides in length and comprise about 19 base pair duplexes.

The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex.

Accordingly, some embodiments of the invention contemplate use of dsRNA to downregulate protein expression from mRNA.

According to one embodiment dsRNA longer than 30 bp are used. Various studies demonstrate that long dsRNAs can be used to silence gene expression without inducing the stress response or causing significant off-target effects—see for example [Strat et al., Nucleic Acids Research, 2006, Vol. 34, No. 13 3803-3810; Bhargava A et al. Brain Res. Protoc. 2004; 13:115-125; Diallo M., et al., Oligonucleotides. 2003; 13:381-392; Paddison P. J., et al., Proc. Natl Acad. Sci. USA. 2002; 99:1443-1448; Tran N., et al., FEBS Lett. 2004; 573:127-134].

According to some embodiments of the invention, dsRNA is provided in cells where the interferon pathway is not activated, see for example Billy et al., PNAS 2001, Vol 98, pages 14428-14433. and Diallo et al., Oligonucleotides, Oct. 1, 2003, 13(5): 381-392. doi:10.1089/154545703322617069.

According to an embodiment of the invention, the long dsRNA are specifically designed not to induce the interferon and PKR pathways for down-regulating gene expression. For example, Shinagwa and Ishii [*Genes & Dev.* 17 (11): 1340-1345, 2003] have developed a vector, named pDECAP, to express long double-strand RNA from an RNA polymerase II (Pol II) promoter. Because the transcripts from pDECAP lack both the 5'-cap structure and the 3'-poly (A) tail that facilitate ds-RNA export to the cytoplasm, long ds-RNA from pDECAP does not induce the interferon response.

Another method of evading the interferon and PKR pathways in mammalian systems is by introduction of small inhibitory RNAs (siRNAs) either via transfection or endogenous expression.

The term "siRNA" refers to small inhibitory RNA duplexes (generally between 18-30 base pairs) that induce the RNA interference (RNAi) pathway.

Typically, siRNAs are chemically synthesized as 21mers with a central 19 bp duplex region and symmetric 2-base 3'-overhangs on the termini, although it has been recently described that chemically synthesized RNA duplexes of 25-30 base length can have as much as a 100-fold increase in potency compared with 21mers at the same location. The observed increased potency obtained using longer RNAs in triggering RNAi is suggested to result from providing Dicer with a substrate (27mer) instead of a product (21mer) and that this improves the rate or efficiency of entry of the siRNA duplex into RISC.

It has been found that position of the 3'-overhang influences potency of an siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

The strands of a double-stranded interfering RNA (e.g., an siRNA) may be connected to form a hairpin or stem-loop structure (e.g., an shRNA). Thus, as mentioned, the RNA silencing agent of some embodiments of the invention may also be a short hairpin RNA (shRNA).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11.

Some of the nucleotides in the loop can be involved in base-pair interactions with other nucleotides in the loop. Examples of oligonucleotide sequences that can be used to form the loop include 5'-CAAGAGA-3' and 5'-UUACAA-3' (International Patent Application Nos. WO2013126963 and WO2014107763). It will be recognized by one of skill in the art that the resulting single chain oligonucleotide forms a stem-loop or hairpin structure comprising a double-stranded region capable of interacting with the RNAi machinery.

Synthesis of RNA silencing agents suitable for use with some embodiments of the invention can be effected as follows. First, the inhibitory-check point mRNA sequence is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tuschl ChemBiochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (www(dot)ambion(dot)com/techlib/tn/91/912(dot)html).

Second, potential target sites are compared to an appropriate genomic database (e.g., human, mouse, rat etc.) using any sequence alignment software, such as the BLAST software available from the NCBI server (www(dot)ncbi (dot)nlm(dot)nih(dot)gov/BLAST/). Putative target sites which exhibit significant homology to other coding sequences are filtered out.

Qualifying target sequences are selected as template for siRNA synthesis.

Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

For example, suitable siRNAs directed against PDL-1 can be obtained from Thermo Fisher Scientific (St Leon-Rot, Germany) and Invitrogen (Carlsbad, Calif., USA); siRNAs directed against PDL-2 can be obtained from Invitrogen (Carlsbad, Calif., USA); siRNA directed against IDO can be as described in Zheng et al. The journal of Immunology (2006) 177(8): 5639-5646.

It will be appreciated that, and as mentioned hereinabove, the RNA silencing agent of some embodiments of the invention need not be limited to those molecules containing only RNA, but further encompasses chemically-modified nucleotides and non-nucleotides.

According to another embodiment the RNA silencing agent may be a miRNA.

The term "microRNA", "miRNA", and "miR" are synonymous and refer to a collection of non-coding single-stranded RNA molecules of about 19-28 nucleotides in length, which regulate gene expression. miRNAs are found in a wide range of organisms (viruses.fwdarw.humans) and have been shown to play a role in development, homeostasis, and disease etiology.

Below is a brief description of the mechanism of miRNA activity.

Genes coding for miRNAs are transcribed leading to production of an miRNA precursor known as the pri-miRNA. The pri-miRNA may form a hairpin with a stem and loop.

The hairpin structure of the pri-miRNA is recognized by Drosha, which is an RNase III endonuclease. Drosha typically recognizes terminal loops in the pri-miRNA and cleaves the pri-miRNA with a staggered cut typical of RNase III endonucleases yielding a pre-miRNA stem loop with a 5' phosphate and ~2 nucleotide 3' overhang. The pre-miRNA is then actively transported from the nucleus to the cytoplasm by Ran-GTP and the export receptor Exportin-5.

The double-stranded stem or the 5' phosphate and 3' overhang at the base of the stem loop of the pre-miRNA is then recognized by Dicer, which is also an RNase III endonuclease. Dicer then cleaves off the terminal loop two helical turns away from the base of the stem loop leaving an additional 5' phosphate and ~2 nucleotide 3' overhang. The resulting siRNA-like duplex, which may comprise mismatches, comprises the mature miRNA and a similar-sized fragment known as the miRNA*. miRNA* sequences may be found in libraries of cloned miRNAs but typically at lower frequency than the miRNAs.

Although initially present as a double-stranded species with miRNA*, the miRNA eventually becomes incorporated as a single-stranded RNA into a ribonucleoprotein complex known as the RNA-induced silencing complex (RISC) while the miRNA* is removed and degraded.

The RISC identifies target nucleic acids based on high levels of complementarity between the miRNA and the mRNA, especially by nucleotides 2-7 of the miRNA.

A number of studies have looked at the base-pairing requirement between miRNA and its mRNA target for achieving efficient inhibition of translation (reviewed by Bartel 2004, Cell 116-281). In mammalian cells, the first 8 nucleotides of the miRNA may be important (Doench & Sharp 2004 GenesDev 2004-504). However, other parts of the microRNA may also participate in mRNA binding. Moreover, sufficient base pairing at the 3' can compensate for insufficient pairing at the 5' (Brennecke et al., 2005 PLoS 3-e85). Computation studies, analyzing miRNA binding on whole genomes have suggested a specific role for bases 2-7 at the 5' of the miRNA in target binding but the role of the first nucleotide, found usually to be "A" was also recognized (Lewis et at 2005 Cell 120-15). Similarly, nucleotides 1-7 or 2-8 were used to identify and validate targets by Krek et al. (2005, Nat Genet 37-495).

The target sites in the mRNA may be in the 5' UTR, the 3' UTR or in the coding region.

miRNAs may direct the RISC to downregulate gene expression by either of two mechanisms: mRNA cleavage or translational repression. The miRNA may specify cleavage of the mRNA if the mRNA has a certain degree of complementarity to the miRNA. When a miRNA guides cleavage, the cut is typically between the nucleotides pairing to residues 10 and 11 of the miRNA. Alternatively, the miRNA may repress translation if the miRNA does not have the requisite degree of complementarity to the miRNA.

It will be appreciated from the description provided herein above that contacting cells with a miRNA may be effected by transfecting/loading the cells with e.g. the mature double stranded miRNA, the pre-miRNA or the pri-miRNA.

The pre-miRNA sequence may comprise from 45-90, 60-80 or 60-70 nucleotides.

The pri-miRNA sequence may comprise from 45-30,000, 50-25,000, 100-20,000, 1,000-1,500 or 80-100 nucleotides.

Antisense—Antisense is a single stranded RNA designed to prevent or inhibit expression of a gene by specifically hybridizing to its mRNA. Downregulation of an immune-check point can be effected using an antisense polynucleotide capable of specifically hybridizing with an mRNA transcript encoding the immune-check point protein.

Design of antisense molecules which can be used to efficiently downregulate an immune-check point must be effected while considering two aspects important to the antisense approach. The first aspect is delivery of the oligonucleotide into the cytoplasm of the appropriate cells, while the second aspect is design of an oligonucleotide which specifically binds the designated mRNA within cells in a way which inhibits translation thereof.

The prior art teaches of a number of delivery strategies which can be used to efficiently deliver oligonucleotides into a wide variety of cell types [see, for example, Jääskeläinen et al. Cell Mol Biol Lett. (2002) 7(2):236-7; Gait, Cell Mol Life Sci. (2003) 60(5):844-53; Martino et al. J Biomed Biotechnol. (2009) 2009:410260; Grijalvo et al. Expert Opin Ther Pat. (2014) 24(7):801-19; Falzarano et al., Nucleic Acid Ther. (2014) 24(1):87-100; Shilakari et al. Biomed Res Int. (2014) 2014: 526391; Prakash et al. Nucleic Acids Res. (2014) 42(13):8796-807 and Asseline et al. J Gene Med. (2014) 16(7-8):157-65].

In addition, algorithms for identifying those sequences with the highest predicted binding affinity for their target mRNA based on a thermodynamic cycle that accounts for the energetics of structural alterations in both the target mRNA and the oligonucleotide are also available [see, for example, Walton et al. Biotechnol Bioeng 65: 1-9 (1999)]. Such algorithms have been successfully used to implement an antisense approach in cells.

In addition, several approaches for designing and predicting efficiency of specific oligonucleotides using an in vitro system were also published [Matveeva et al., Nature Biotechnology 16: 1374-1375 (1998)].

Thus, the generation of highly accurate antisense design algorithms and a wide variety of oligonucleotide delivery systems, enable an ordinarily skilled artisan to design and implement antisense approaches suitable for downregulating expression of known sequences without having to resort to undue trial and error experimentation.

Nucleic acid agents can also operate at the DNA level as summarized infra.

Suppressing the biological function of an immune-check point can also be achieved by inactivating the gene (e.g., PD-1, PDL-1, CTLA-4, LAG-3, TIM-3, KIR and IDO) via introducing targeted mutations involving loss-of function alterations (e.g. point mutations, deletions and insertions) in the gene structure.

As used herein, the phrase "loss-of-function alterations" refers to any mutation in the DNA sequence of a gene which results in downregulation of the expression level and/or activity of the expressed product, i.e., the mRNA transcript and/or the translated protein. Non-limiting examples of such loss-of-function alterations include a missense mutation, i.e., a mutation which changes an amino acid residue in the protein with another amino acid residue and thereby abolishes the enzymatic activity of the protein; a nonsense mutation, i.e., a mutation which introduces a stop codon in a protein, e.g., an early stop codon which results in a shorter protein devoid of the enzymatic activity; a frame-shift mutation, i.e., a mutation, usually, deletion or insertion of nucleic acid(s) which changes the reading frame of the protein, and may result in an early termination by introducing a stop codon into a reading frame (e.g., a truncated protein, devoid of the enzymatic activity), or in a longer amino acid sequence (e.g., a readthrough protein) which affects the secondary or tertiary structure of the protein and results in a non-functional protein, devoid of the enzymatic activity of the non-mutated polypeptide; a readthrough mutation due to a frame-shift mutation or a modified stop codon mutation (i.e., when the stop codon is mutated into an amino acid codon), with an abolished enzymatic activity; a promoter mutation, i.e., a mutation in a promoter sequence, usually 5' to the transcription start site of a gene, which results in down-regulation of a specific gene product; a regulatory mutation, i.e., a mutation in a region upstream or downstream, or within a gene, which affects the expression of the gene product; a deletion mutation, i.e., a mutation which deletes coding nucleic acids in a gene sequence and which may result in a frame-shift mutation or an in-frame mutation (within the coding sequence, deletion of one or more amino acid codons); an insertion mutation, i.e., a mutation which inserts coding or non-coding nucleic acids into a gene sequence, and which may result in a frame-shift mutation or an in-frame insertion of one or more amino acid codons; an inversion, i.e., a mutation which results in an inverted coding or non-coding sequence; a splice mutation i.e., a mutation which results in abnormal splicing or poor splicing; and a duplication mutation, i.e., a mutation which results in a duplicated coding or non-coding sequence, which can be in-frame or can cause a frame-shift.

According to specific embodiments loss-of-function alteration of a gene may comprise at least one allele of the gene.

The term "allele" as used herein, refers to any of one or more alternative forms of a gene locus, all of which alleles relate to a trait or characteristic. In a diploid cell or organism, the two alleles of a given gene occupy corresponding loci on a pair of homologous chromosomes.

According to other specific embodiments loss-of-function alteration of a gene comprises both alleles of the gene.

Methods of introducing nucleic acid alterations to a gene of interest are well known in the art [see for example Menke D. Genesis (2013) 51:-618; Capecchi, Science (1989) 244: 1288-1292; Santiago et al. Proc Natl Acad Sci USA (2008) 105:5809-5814; International Patent Application Nos. WO2014085593, WO2009071334 and WO2011146121; U.S. Pat. Nos. 8,771,945, 8,586,526, 6,774,279 and U.S. Patent Application Publication Nos. 20030232410, 20050026157, US20060014264; the contents of which are incorporated by reference in their entireties] and include targeted homologous recombination (e.g. "Hit and run", "double-replacement"), site specific recombinases (e.g. the Cre recombinase and the Flp recombinase), PB transposases (e.g. Sleeping Beauty, piggyBac, To12 or Frog Prince), genome editing by engineered nucleases (e.g. meganucleases, Zinc finger nucleases (ZFNs), transcription-activator like effector nucleases (TALENs) and CRISPR/Cas system) and genome editing using recombinant adeno-associated virus (rAAV) platform. Agents for introducing nucleic acid alterations to a gene of interest can be designed publically available sources or obtained commercially from Transposagen, Addgene and Sangamo Biosciences.

Methods for qualifying efficacy and detecting sequence alteration are well known in the art and include, but not limited to, DNA sequencing, electrophoresis, an enzyme-based mismatch detection assay and a hybridization assay such as PCR, RT-PCR, RNase protection, in-situ hybridization, primer extension, Southern blot, Northern Blot and dot blot analysis.

Sequence alterations in a specific gene can also be determined at the protein level using e.g. chromatography, electrophoretic methods, immunodetection assays such as ELISA and western blot analysis and immunohistochemistry.

As mentioned, depending on the immune-check point protein (i.e. co-stimulatory or inhibitory) the immune-check point regulator can be an agonist or antagonist. Thus, according to specific embodiments, the immune-check point regulator is an agonist.

As used herein the term "agonist" refers to a molecule that induces and/or increases the biological function and/or expression of an immune-check point protein.

According to specific embodiments, the agonist induces and/or increases the co-stimulatory effect of an immune-check point protein on an immune cell (e.g. T cells).

According to specific embodiments, the agonist induces and/or increases signaling to an immune cell (e.g. T cell) by an immune-check point protein.

The agonist can be a naturally occurring activator or a functional derivative thereof; or non-naturally occurring activator.

According to specific embodiments, the agonist is a full agonist, that is, the effect of the agonist is equivalent to the effect of the naturally occurring activator (i.e. ligand).

According to other specific embodiments, the agonist is a partial agonist, that is, the effect of the agonist is lower than the maximal effect of the naturally occurring activator (i.e. ligand). The effect of the agonist may be lower by at least 5%, at least 10%, at least 20%, at least 30%, at least 40% at least 50%, at least 60%, at least 70%, at least 80% or at least 90% as compared to the maximal effect of the naturally occurring activator.

According to yet other specific embodiments, the agonist is a super agonist, that is, the effect of the agonist is higher than the maximal effect of the naturally occurring activator (i.e. ligand). The effect of the agonist may be higher by at least 5%, at least 10%, at least 20%, at least 30%, at least 40% at least 50%, at least 60%, at least 70%, at least 80%, at least 90% or at least 2 fold, at least 4 fold, at least 5 fold or at least 10 fold as compared to the maximal effect of the naturally occurring activator.

According to specific embodiments, the agonist induces complete activation the biological function (e.g. signal transduction) of the immune-check point protein.

According to other specific embodiments, the agonist increases the biological function (e.g. signal transduction) of the immune-check point protein e.g., as detected by e.g. kinase activity, proliferation assay, cytotoxicity assay or cytokine secretion assay. The increase may be by at least a 10%, at least 20%, at least 30%, at least 40%, at least 50%, at least 60%, at least 70%, at least 80%, at least 90%, at least 95% or at least 99% as compared to same in the absence of the agonist.

According to specific embodiments, the agonist binds directly the immune-check point protein.

According to other specific embodiments, the agonist indirectly binds the immune-check point protein by acting through an intermediary molecule, for example the agonist binds to or modulates a molecule that in turn binds to or modulates the immune-check point protein.

Activating and/or increasing the biological function of an immune-check point protein can be effected at the protein level (e.g., antibodies, small molecules, peptides and the like) but may also be effected at the genomic level (e.g., activation of transcription via promoters, enhancers, regulatory elements) and/or the transcript level using a variety of molecules which promote transcription and/or translation (e.g., correct splicing, polyadenylation, activation of translation) of a co-stimulatory immune-check point protein.

Non limiting examples of agents that can function as agonists are described in details hereinbelow.

Activating and/or Increasing Biological Function at the Polypeptide Level

According to specific embodiments, the agonist is the naturally occurring activator or a functional derivative or variant thereof which retain the ability to specifically bind to the immune-check point protein.

It will be appreciated that a functional analogue of at least a catalytic or binding portion of a co-stimulatory peptide can be also used as an agonist. Thus, according to specific embodiments, the agonist is an exogenous polypeptide including at least a functional portion (e.g. catalytic or interaction) of the co-stimulatory immune-check point protein. Thus, for example, the polypeptide can be a ligand capable of binding and activating the co-stimulatory immune-check point protein receptor.

According to specific embodiments, the agonist is an antibody.

According to specific embodiments the agonistic antibody is capable of specifically binding a co-stimulatory immune-check point protein. According to specific embodiments, the agonistic antibody specifically binds at least one epitope of a co-stimulatory immune-check point protein. A detailed description on antibodies that can be used according to specific embodiments of the present invention is provided hereinabove.

Another agent capable of being an agonist would be a molecule which promotes and/or increases the co-stimulatory immune-check point protein function (e.g. catalytic or interaction) by binding to the immune-check point protein or an intermediate thereof. Such molecules can be, but are not limited to, small molecules, peptides, aptamers, adnectins, affibodies, avimers, anticalins, tetranectins and DARPins, wherein each possibility is a separate embodiment of the invention.

According to specific embodiments, the agonist is a small molecule.

According to specific embodiments, the agonist is a peptide.

Activating and/or Increasing Biological Function at the Nucleic Acid Level

An agonist can also be a molecule which is capable of increasing the transcription and/or translation of an endogenous DNA or mRNA encoding the co-stimulatory immune-check point protein and thus increasing endogenous co-stimulatory immune-check point protein activity.

Another agonistic agent may be an exogenous polynucleotide (DNA or RNA) sequence designed and constructed to express at least a functional portion of the co-stimulatory immune-check point protein.

Several co-stimulatory immune-check points have been cloned from human, rat and mouse sources. Thus, coding sequences information is available from several databases including the GenBank database available through www (dot)ncbi(dot)nlm(dot)nih(dot)gov/.

To express an exogenous co-stimulatory immune-check point protein in mammalian cells, a polynucleotide sequence encoding a specific co-stimulatory immune-check point protein or a homologue thereof which exhibit the desired activity is preferably ligated into a nucleic acid construct suitable for mammalian cell expression. Such a nucleic acid construct includes a promoter sequence for directing transcription of the polynucleotide sequence in the cell in a constitutive [e.g. cytomegalovirus (CMV) and Rous sarcoma virus (RSV)] or inducible (e.g. the tetracycline-inducible promoter) manner.

According to specific embodiments, the promoter utilized by the nucleic acid construct of some embodiments of the invention is active in a specific cell population. Examples of cell type-specific and/or tissue-specific promoters include promoters such as, but not limited to lymphoid specific promoters [Calame et al., (1988) Adv. Immunol. 43:235-275]; in particular promoters of T-cell receptors [Winoto et al., (1989) EMBO J. 8:729-733] and immunoglobulins [Banerji et al. (1983) Cell 33729-740].

The nucleic acid construct (also referred to herein as an "expression vector") of some embodiments of the invention includes additional sequences which render this vector suitable for replication and integration in prokaryotes, eukaryotes, or preferably both (e.g., shuttle vectors). In addition, a typical cloning vectors may also contain a transcription and translation initiation sequence, transcription and translation terminator and a polyadenylation signal. By way of example, such constructs will typically include a 5' LTR, a tRNA binding site, a packaging signal, an origin of second-strand DNA synthesis, and a 3' LTR or a portion thereof. The construct may also include an enhancer element which can stimulate transcription up to 1,000 fold from linked homologous or heterologous promoters. The vector may or may not include a eukaryotic replicon.

The nucleic acid construct of some embodiments of the invention can also include a signal sequence for secretion of the peptide from a host cell in which it is placed. Preferably the signal sequence for this purpose is a mammalian signal sequence or the signal sequence of the polypeptide variants of some embodiments of the invention.

Polyadenylation sequences can also be added to the expression vector in order to increase the efficiency of a co-stimulatory immune-check point mRNA translation. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for some embodiments of the invention include those derived from SV40.

The expression vector of some embodiments of the invention can further include additional polynucleotide sequences that allow, for example, the translation of several proteins from a single mRNA such as an internal ribosome entry site (IRES) and sequences for genomic integration of the promoter-chimeric polypeptide.

Other than containing the necessary elements for the transcription and translation of the inserted coding sequence, the expression construct of some embodiments of the invention can also include sequences engineered to enhance stability, production, or yield of the expressed peptide.

It will be appreciated that the individual elements comprised in the expression vector can be arranged in a variety of configurations.

The type of vector used by some embodiments of the invention will depend on the cell type transformed. The ability to select suitable vectors according to the cell type transformed is well within the capabilities of the ordinary skilled artisan and as such no general description of selection consideration is provided herein.

Recombinant viral vectors are useful for in vivo expression of an immune-check point protein since they offer advantages such as lateral infection and targeting specificity. Viral vectors can also be produced that are unable to spread laterally.

Various methods can be used to introduce the expression vector of some embodiments of the invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et al. [Biotechniques 4 (6): 504-512, 1986]. Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. Other vectors can be used that are non-viral, such as cationic lipids, polylysine, and dendrimers.

As mentioned, the CXCR4 antagonistic peptides of the present invention may be used in combination with an immune-check point regulator for the treatment of cancer. According to specific embodiments, wherein the immune-check protein is an inhibitory protein, the CXCR4 antagonistic peptides of the present invention are administered in combination with an immune-check point antagonist. Following is a list of combinations that may be used in accordance with the present teachings.

Thus, according to an aspect of the present invention there is provided a method of treating cancer in a subject in need thereof, the method comprising:

(a) administering to the subject a therapeutically effective amount of a peptide having an amino acid sequence as set forth in SEQ ID NO: 1 or an analog or derivative thereof; and (b) administering to the subject a therapeutically effective amount of a PD1 antagonist, thereby treating the cancer in the subject.

According to an aspect of the present invention there is provided an article of manufacture identified for use in treating cancer, comprising a packaging material packaging a peptide having an amino acid sequence as set forth in SEQ ID NO: 1 or an analog or derivative thereof and a PD1 antagonist.

According to an aspect of the present invention there is provided a pharmaceutical composition comprising as active ingredients a peptide having an amino acid sequence as set forth in SEQ ID NO: 1 or an analog or derivative thereof and a PD1 antagonist; and a pharmaceutically acceptable carrier or diluent.

PD1 (Programmed Death 1, also known as CD279) is a 55 kDa type I transmembrane protein that is part of the Ig gene superfamily, which is expressed on the surface of several immune cells such as activated T cells, B cells, NK cells and myeloid cells. PD-1 contains a membrane proximal immunoreceptor tyrosine inhibitory motif (ITIM) and a membrane distal tyrosine-based switch motif (ITSM).

The presence of an ITIM on PD-1 indicates that this molecule functions to attenuate antigen receptor signaling by recruitment of cytoplasmic phosphatases.

According to a specific embodiment, the PD1 protein refers to the human protein, such as provided in the following GenBank Number NP_005009. Two ligands for PD-1 have been identified, PD-L1 and PD-L2 (also known as B7-DC).

According to a specific embodiment, the PD-L1 protein refers to the human protein, such as provided in the following GenBank Number NP_001254635 and NP_054862. According to a specific embodiment, the PD-L2 protein refers to the human protein, such as provided in the following GenBank Number NP_079515.

PD1 pattern of expression and function is dependent on the cell type. PD1 expression is induced following effector T cells activation. Upon ligand binding, PD1 inhibits kinases that are involved in T cell activation through e.g. the phosphatase SHP2, thereby transmits an inhibitory signal. Conversely, PD1 is highly expressed on regulatory T cells, where it may enhance their proliferation upon ligand binding. PD-1 is also induced on other activated non-T lymphocyte subsets, including B cells and NK cells, where upon ligand binding it transmits an inhibitory signal which limits their antibody production and lytic activity, respectively [Pardoll (2012) Nature Reviews Cancer 12, 252-264].

Thus, PD1 blockade may enhance the activity of effector T cells, NK cells and antibody production in tissues and in the tumor microenvironment. Because many tumors are highly infiltrated with regulatory T cells that probably further suppress effector immune responses, blockade of the PD1 pathway may also enhance antitumor immune responses by diminishing the number and/or suppressive activity of intra-tumoral regulatory T cells.

As used herein, the term "PD1 antagonist" refers to an antagonistic agent that prevents and/or inhibits the biological function and/or expression of PD1.

According to specific embodiments, the PD1 antagonist prevents and/or inhibits signaling to an immune cell (e.g. T cells, B cells, NK cells) by PD1; thereby suppresses PD1 immune-suppressive activity.

According to specific embodiments, the PD1 antagonist promotes immune response of an effector T cell following TCR activating signal.

According to specific embodiments, the PD1 antagonist of the present invention binds directly PD1 and/or binds a ligand of PD1 and interferes with and/or inhibits the binding of the ligands to PD1.

According to other specific embodiments, the PD1 antagonist indirectly binds PD1 by acting through an intermediary molecule, for example the antagonist binds to or modulates a molecule that in turn binds to or modulates PD1.

According to specific embodiments, the PD1 antagonist binds PD1. According to other specific embodiments, the PD1 antagonist binds at least one of the PD-1 ligands (e.g. PDL-1 or PDL-2), as further described hereinbelow.

In certain embodiments, the PD1 antagonist exhibits one or more desirable functional properties, such as high affinity binding to PD1, e.g., binding to human PD1 with a $K_D$ of $10^{-7}$ M, $10^{-8}$ M, $10^{-9}$ M, $10^{-10}$ M or less; lack of significant cross-reactivity to other immune-check point proteins, e.g., CD28, CTLA-4 and ICOS; the ability to stimulate T cell proliferation; the ability to increase IFN-γ and/or IL-2 secretion; the ability to inhibit binding of one or more PD1 ligands (e.g., PD-L1 and/or PD-L2) to PD1; the ability to stimulate antigen-specific memory responses; the ability to stimulate antibody responses and/or the ability to inhibit growth of tumor cells.

According to a specific embodiment, the PD1 antagonist is an antibody.

According to specific embodiments, the PD1 antagonist is an anti-PD1 antibody. Anti-PD1 antibodies suitable for use in the invention can be generated using methods well known in the art especially in light of the detailed description hereinabove. Alternatively, art recognized anti-PD1 antibodies can be used. Examples of anti-PD1 antibodies are disclosed for example in Topalian, et al. NEJM 2012, U.S. Pat. Nos. 7,488,802; 8,008,449; 8,609,089; 6,808,710; 7,521,051; and 8,168,757, U.S. Patent Application Publication Nos. 20140227262; 20100151492; 20060210567; and 20060034826 and International Patent Application Publication Nos. WO2008156712; WO2010089411; WO2010036959; WO2011159877; WO2013/019906; WO2014159562; WO2011109789; WO01/14557; WO2004/004771; and WO2004/056875, which are hereby incorporated by reference in their entirety.

Specific anti-PD1 antibodies that can be used according to some embodiments of the present invention include, but are not limited to:

Nivolumab (also known as MDX1106, BMS-936558, ONO-4538), marketed by BMY as Opdivo, a fully human IgG4 antibody with the structure described in WHO Drug Information, Vol. 27, No. 1, pages 68-69 (2013) that binds to and blocks the activation of PD-1 by its ligands PD-L1 and PD-L2;

Pembrolizumab (also known as MK-3475, Keytruda, SCH 900475, produced by Merck), a humanized monoclonal IgG4 antibody with the structure described in WHO Drug Information, Vol. 27, No. 2, pages 161-162 (2013) that binds to and blocks the activation of PD1 by its ligands;

Pidilizumab (also known as CT-011, hBAT, hBAT-1, produced by CureTech), a humanized monoclonal IgG1 antibody that binds PD-1;

AMP-514 (also known as MEDI-0680, produced by AZY and MedImmune), a humanized monoclonal IgG4 antibody that binds PD-1.

Humanized antibodies h409A11, h409A16 and h409A17, which are described in PCT Patent Application No. WO2008/156712.

According to a specific embodiment, the antibody competes with any of the above-mentioned antibodies for binding to PD1.

According to a specific embodiment, the antibody competes for binding with and/or binds to the same epitope on PD1 as the above-mentioned antibodies.

According to another specific embodiment, the antibody has at least about 90% variable region amino acid sequence identity with the above-mentioned antibodies.

According to a specific embodiment, the PD1 antagonist is an anti-PDL-1 antibody, as further described hereinbelow.

According to a specific embodiment, the PD1 antagonist is an anti-PDL-2 antibody.

Anti-PDL-2 antibodies suitable for use in the invention can be generated using methods well known in the art especially in light of the detailed description hereinabove. Alternatively, art recognized anti-PDL-2 antibodies can be used. Examples of anti-PD1 antibodies are disclosed for example in International Application Publication Nos. WO03/042402 and WO02/00730, which are hereby incorporated by reference in their entirety.

Other PD1 antagonists include an immunoadhesin that specifically binds to PD-1 or any one of its ligands, such as a fusion protein containing the extracellular or PD1 binding portion of PD-L1 or PD-L2 fused to a constant region such as an Fc region of an immunoglobulin molecule. Examples of immunoadhesin molecules that specifically bind to PD1 are described in International Patent Application Publication Nos. WO2010/027827 and WO2011/066342, which are hereby incorporated by reference in their entirety.

A specific fusion protein that can be used according to some embodiments of the present invention is AMP-224 (also known as B7-DCIg, produced by AZY and GSK), an engineered recombinant fusion protein comprised of human PD-L2 and the Fc domain of human IgG1.

Other PD1 antagonists that can be used according to some embodiments of the present invention including nucleotides, expression vectors, small molecules, peptides, fusion proteins and fragments targeting PD1, PDL-1 or PDL-2, non-functional PD1, soluble PD1 or fragments thereof that bind to PD1 ligands and prevent binding to the endogenous PD1 receptor, are disclosed for examples in U.S. Pat. Nos. 8,609,089 and 6,808,710, U.S. Patent Application Publication Nos. 20140227262; 20100151492; 20040137577; 20030232323; 20030044768; 20030039653; 20020164600; 20020110836; 20020107363; 20020106730; 20090305950 and 20140271677, International Patent Application Publication Nos. WO03042402; WO2010036959; WO2011066342; WO2011082400; WO2011161699; WO2014012479; WO2011109789; and WO2013132317, which are hereby incorporated by reference in their entirety.

According to an aspect of the present invention there is provided a method of treating cancer in a subject in need thereof, the method comprising:

(a) administering to the subject a therapeutically effective amount of a peptide having an amino acid sequence as set forth in SEQ ID NO:1 or an analog or derivative thereof; and (b) administering to the subject a therapeutically effective amount of a PD-L1 antagonist, thereby treating the cancer in the subject.

According to an aspect of the present invention there is provided an article of manufacture identified for use in treating cancer, comprising a packaging material packaging a peptide having an amino acid sequence as set forth in SEQ ID NO: 1 or an analog or derivative thereof and a PD-L1 antagonist.

According to an aspect of the present invention there is provided a pharmaceutical composition comprising as active ingredients a peptide having an amino acid sequence as set forth in SEQ ID NO: 1 or an analog or derivative thereof and a PD-L1 antagonist; and a pharmaceutically acceptable carrier or diluent.

PDL-1 (also known as B7-H1) is a B7 homolog that binds PD1 and B7.1 (CD80). PDL-1 is constitutively expressed on T cells, B cells, dendritic cells, macrophages, mesenchymal stem cells, bone marrow-derived mast cells and also on a wide range of non-hematopoietic cells (e.g., cornea, lung, vascular epithelium, liver non-parenchymal cells, pancreatic islets, placental synctiotrophoblasts, keratinocytes, etc.) and is upregulated on a number of cell types after activation [Yamazaki et al., J. Immunol. 169: 5538-45 (2002); Keir et al., Annu. Rev. Immunol. 26: 677-704 (2008)]. In addition, many cancerous cells such as, but not limited to, melanoma, ovarian and lung cancerous cells express PDL-1 [Pardoll (2012) Nature Reviews Cancer 12, 252-264]. According to a specific embodiment the PDL-1 protein refers to the human protein, such as provided in the following GenBank accession Numbers NP_054862 and NP_054862.

Binding of PDL-1 to PD1 or B7.1 has been shown to downregulate T cell activation [Butte et al. (2007) Immunity 27: 111-22]. It has also been shown that the interaction between PD-1 and PD-L1 results in a decrease in tumor infiltrating lymphocytes, a decrease in T-cell receptor mediated proliferation, and immune evasion by the cancerous cells (Dong et al. (2003) J. Mol. Med. 81:281-7; Blank et al. (2005) Cancer Immunol. Immunother. 54:307-314; Konishi et al. (2004) Clin. Cancer Res. 10:5094-100).

As used herein, the term "PDL-1 antagonist" refers to an antagonistic agent that prevents and/or inhibits the biological function and/or expression of PDL-1.

According to specific embodiments, the PDL-1 antagonist prevents and/or inhibits signaling to an immune cell (e.g. T cells, B cells, NK cells) by the interaction of PDL-1 with at least one of its binding partners (e.g. PD-1 and B7.1); thereby suppresses PDL-1 immune-suppressive activity.

According to specific embodiments, the PDL-1 antagonist binds to or inhibits PD-L1 from binding and/or activating its binding partner.

According to specific embodiments, the PDL-1 antagonist binds PDL-1 and interferes with and/or inhibits the binding of PDL-1 to PD1 and/or B7.1.

According to specific embodiments, the PDL-1 antagonist binds PDL-1 and prevents and/or inhibits PD1 and/or B7.1 activation by the PDL-1.

According to other specific embodiments, the PDL-1 antagonist indirectly binds PDL-1 by acting through an intermediary molecule, for example the antagonist binds to or modulates a molecule that in turn binds to or modulates PDL-1.

According to specific embodiments, the PDL-1 antagonist exhibits one or more desirable functional properties, such as high affinity binding to PDL-1, e.g., binding to human PDL-1 with a $K_D$ of $10^{-7}$ M, $10^{-8}$ M, $10^{-9}$ M, $10^{-10}$ M or less; lack of significant cross-reactivity to other immune-check point proteins; the ability to stimulate T cell proliferation; the ability to increase IFN-γ and/or IL-2 secretion; the ability to stimulate antibody responses and/or the ability to inhibit growth of tumor cells.

According to a specific embodiment, the PDL-1 antagonist is an anti-PDL-1 antibody.

Anti-PDL-1 antibodies suitable for use in the invention can be generated using methods well known in the art especially in light of the detailed description hereinabove. Alternatively, art recognized anti-PDL-1 antibodies can be used. Examples of anti-PDL-1 antibodies are disclosed for example in Brahmer, et al. NEJM 2012, U.S. Pat. Nos. 7,943,743; 8,217,149; 8,741,295; 8,552,154; and 8,383,796, U.S. Patent Application Publication Nos. 20140227262; and 20030232323, International Patent Application Publication Nos. WO2014066834; WO2010036959; WO2011066342; WO2013/019906, WO2010/077634; WO2002079499; WO2003042402, WO2002086083; WO2001039722; WO2007005874 WO2011109789; and WO2007005874, which are hereby incorporated by reference in their entirety.

Specific anti-PDL-1 antibodies that can be used according to some embodiments of the present invention include, but are not limited to:

MPDL3280A (also known as RG7446, produced by Roche/Genentech), a human, Fc optimized, monoclonal antibody that binds PD-L1 and prevents its binding to and activation of PD1 and B7.1. This antibody contains an engineered Fc domain designed to optimize efficacy and safety by minimizing antibody-dependent cellular cytotoxicity (ADCC);

BMS-936559 (produced by BMS), a fully human IgG4 anti-PD-L1 monoclonal antibody that inhibits the binding of the PD-L1 to both PD-1 and B7.1;

MEDI4736 (also known as Anti-B7-H1, produced by AstraZeneca), a monoclonal antibody that binds PDL-1;

Avelumab (also known as MSB0010718C, produced by Merck KGaA), a fully human anti-PD-L1 IgG1 monoclonal antibody; and Monoclonal antibodies 12A4, 3G10, 10A5, 5F8, 10H10, 1B12, 7H1, 11E6, 12B7, and 13G4 described in International Application Publication No. WO2007/005874 and U.S. Pat. No. 7,943,743.

According to a specific embodiment, the antibody competes with any of the above-mentioned antibodies for binding to PDL-1.

According to a specific embodiment, the antibody competes for binding with and/or binds to the same epitope on PDL-1 as the above-mentioned antibodies.

According to another specific embodiment, the antibody has at least about 90% variable region amino acid sequence identity with the above-mentioned antibodies.

Other PDL-1 antagonists that can be used according to some embodiments of the present invention include nucleotides, expression vectors, small molecules, peptides, immunoadhesins, fusion proteins and fragments targeting PDL-1, non-functional PDL-1 or fragments thereof that bind to but do not promote signaling by PD1, are disclosed for examples in U.S. Pat. No. 6,808,710; U.S. Patent Application Publication Nos. 20140227262; 20030232323; 20030039653; and 20140271677; International Patent Application Publication Nos. WO2011066342; WO2013/019906; and WO2011109789, which are hereby incorporated by reference in their entirety.

According to an aspect of the present invention there is provided a method of treating cancer in a subject in need thereof, the method comprising:

(a) administering to the subject a therapeutically effective amount of a peptide having an amino acid sequence as set forth in SEQ ID NO:1 or an analog or derivative thereof; and (b) administering to the subject a therapeutically effective amount of a CTLA-4 antagonist, thereby treating the cancer in the subject.

According to an aspect of the present invention there is provided an article of manufacture identified for use in treating cancer, comprising a packaging material packaging a peptide having an amino acid sequence as set forth in SEQ ID NO: 1 or an analog or derivative thereof; and a CTLA-4 antagonist.

According to an aspect of the present invention there is provided a pharmaceutical composition comprising as active ingredients a peptide having an amino acid sequence as set forth in SEQ ID NO: 1 or an analog or derivative thereof; and a CTLA-4 antagonist; and a pharmaceutically acceptable carrier or diluent.

CTLA4 is a member of the immunoglobulin superfamily, which is expressed on the surface of T cells (e.g. CD4+ helper T cells) and transmits an inhibitory signal to T cells upon ligand binding. According to a specific embodiment the CTLA-4 protein refers to the human protein, such as provided in the following GenBank Number NP_001032720. Two ligands for CTLA-4 have been identified, B7.1 (also known as CD80) and B7.2 (also known as CD86). According to a specific embodiment the B7.1 protein refers to the human protein, such as provided in the following GenBank Number NP_005182. According to a specific embodiment the B7.2 protein refers to the human protein, such as provided in the following GenBank Number NP_001193853.

CTLA4 is expressed on both activated CD4+ helper and $CD8^+$ cytotoxic effector T cells, however the major physiological role of CTLA4 seems to be through distinct effects on the two major subsets of $CD4^+$ T cells: down-modulation of helper T cell activity and enhancement of regulatory T cell immunosuppressive activity.

Typically, Naive and memory T cells express high levels of cell surface CD28 but do not express CTLA4 on their surface. After the TCR is triggered by antigen encounter, CTLA4 is transported to the cell surface. Binding of any of the CTL4 ligands to CTLA4 on effector cell results in the inhibition of IL-2 synthesis and progression through the cell cycle and termination of T-cell responses [Walunas et al., J. Exp. Med. 183: 2541-2550 (1996); Greenwald et al., Immunity 14: 145-155 (2001)]. Regulatory T cells, on the contrary, express CTLA4 constitutively and CTLA4 engagement on regulatory T cell enhances its suppressive function [Pardoll (2012) Nature Reviews Cancer 12, 252-264].

Thus, CTLA4 blockade may enhance the activity of effector $CD4^+$ T cell activity and/or inhibit regulatory T cell-dependent immunosuppression.

As used herein, the term "CTLA4 antagonist" refers to an antagonistic agent that prevents and/or inhibits the biological function and/or expression of CTLA4.

According to specific embodiments, the CTLA4 antagonist prevents and/or inhibits signaling to an immune cell (e.g. T cells) by CTLA4; thereby suppresses CTLA4 immune-suppressive activity.

According to specific embodiments, the CTLA4 antagonist promotes immune response of a helper T cell following TCR activating signal.

According to specific embodiments, the CTLA4 antagonist inhibits immune suppressive effect of a regulatory T cell.

According to specific embodiments, the CTLA4 antagonist of the present invention binds directly CTLA4 and/or binds ligands of CTLA4 and interferes with and/or inhibits the binding of the ligands to CTLA4.

According to other specific embodiments, the CTLA4 antagonist indirectly binds CTLA4 by acting through an intermediary molecule, for example the antagonist binds to or modulates a molecule that in turn binds to or modulates CTLA4.

According to specific embodiments, the CTLA4 antagonist binds CTLA4.

According to other specific embodiments, the CTLA4 antagonist binds at least one of the CTLA4 ligands (e.g. B7.1 and B7.2).

In certain embodiments, the CTLA4 antagonist exhibits one or more desirable functional properties, such as high affinity binding to CTLA4 or its ligand, e.g., binding to human CTLA4 with a $K_D$ of $10^{-7}$ M, $10^{-8}$ M, $10^{-9}$ M, $10^{-10}$ M or less; lack of significant cross-reactivity to other immune-check point proteins, e.g., CD28 and ICOS; the ability to stimulate T cell proliferation; the ability to increase IFN-γ and/or IL-2 secretion; the ability to inhibit binding of one or more CTLA4 ligands (e.g., B7.1 and B7.2) to CTLA4; the ability to inhibit regulatory T cell response; and/or the ability to inhibit growth of tumor cells.

According to a specific embodiment, the CTLA4 antagonist is an antibody.

According to specific embodiments, the CTLA4 antagonist is an anti-CTLA4 antibody. Anti-CTLA4 antibodies suitable for use in the invention can be generated using methods well known in the art especially in light of the detailed description hereinabove. Alternatively, art recognized anti-CTLA4 antibodies can be used.

Examples of anti-CTLA4 antibodies are disclosed for example in Hurwitz et al. (1998) Proc. Natl. Acad. Sci. USA 95(17): 10067-10071; Camacho et al. (2004) J. Clin. Oncology 22(145): Abstract No. 2505 (antibody CP-675206); and Mokyr et al. (1998) Cancer Res. 58:5301-5304; U.S. Pat. Nos. 5,811,097; 5,855,887; 6,051,227; 6,207,157; 6,207,156; 6,682,736; 6,984,720; 5,977,318; 7,109,003; 7,132,281; 8,993,524 and 7,605,238, U.S. Patent Application Publication Nos. 09/644,668; 2005/0201994; 2002/086014, International Application Publication Nos. WO2014066834; WO01/14424 and WO00/37504; WO2002/0039581; WO98/42752; WO00/37504; WO2004/035607; and WO01/14424, and European Patent No. EP1212422B1, which are hereby incorporated by reference in their entirety.

Specific anti-CTLA4 antibodies that can be used according to some embodiments of the present invention include, but are not limited to:

Ipilimumab (also known as 10D1, MDX-D010), marketed by BMS as Yervoy™, a fully human monoclonal IgG antibody that binds to CTLA-4; and Tremelimumab, (ticilimumab, CP-675,206, produced by MedImmune and Pfizer), a human IgG2 monoclonal antibody that binds CTLA4.

According to a specific embodiment, the antibody competes with any of the above-mentioned antibodies for binding to CTLA4.

According to a specific embodiment, the antibody competes for binding with and/or binds to the same epitope on CTLA4 as the above-mentioned antibodies.

According to another specific embodiment, the antibody has at least about 90% variable region amino acid sequence identity with the above-mentioned antibodies.

Other CTLA4 antagonists that can be used according to some embodiments of the invention include nucleotides, expression vectors, small molecules, peptides, fusion proteins and fragments targeting CTL4 or any of its ligands, non-functional CTLA4, soluble CTLA4 or fragments thereof that bind to CTLA4 ligands and prevent binding to the endogenous CTLA4 receptor, such as disclosed for examples in U.S. Pat. No. 8,993,524, U.S. Patent Application Publication Nos. 20030232323; 20020106730; and 20140271677, International Patent Application Publication Nos. WO2014012479; and WO2014089113, which are hereby incorporated by reference in their entirety.

According to an aspect of the present invention there is provided a method of treating cancer in a subject in need thereof, the method comprising:

(a) administering to the subject a therapeutically effective amount of a peptide having an amino acid sequence as set forth in SEQ ID NO:1 or an analog or derivative thereof; and (b) administering to the subject a therapeutically effective amount of a LAG-3 antagonist, thereby treating the cancer in the subject.

According to an aspect of the present invention there is provided an article of manufacture identified for use in treating cancer, comprising a packaging material packaging a peptide having an amino acid sequence as set forth in SEQ ID NO: 1 or an analog or derivative thereof and a LAG-3 antagonist.

According to an aspect of the present invention there is provided a pharmaceutical composition comprising as active ingredients a peptide having an amino acid sequence as set forth in SEQ ID NO: 1 or an analog or derivative thereof and a LAG-3 antagonist; and a pharmaceutically acceptable carrier or diluent.

LAG-3 (also known as CD223) is a member of the immunoglobulin superfamily which is expressed on the surface of several immune cells such as activated T cells, natural killer cells, B cells and plasmacytoid dendritic cells.

According to a specific embodiment the LAG-3 protein refers to the human protein, such as provided in the following GenBank Number NP_002277. The only currently known ligand for LAG-3 is MHC class II molecules, which are upregulated on tumor-infiltrating macrophages and dendritic cells and also on some cancers such as epithelial cancers [Pardoll (2012) Nature Reviews Cancer 12, 252-264].

Upon ligand binding LAG-3 inhibits e.g. effector T cell activation, proliferation and function and also has a role in enhancing the function of regulatory T cells. The LAG-3 MHC class II interaction has also roles in modulating dendritic cell function. Thus, LAG3 blockade may enhance the activity of effector T cell activity and inhibit regulatory T cell cell-dependent immunosuppression.

As used herein, the term "LAG-3 antagonist" refers to an antagonistic agent that prevents and/or inhibits the biological function and/or expression of LAG-3.

According to specific embodiments, the LAG-3 antagonist prevents and/or inhibits signaling to an immune cell (e.g. T cells) by LAG-3; thereby suppresses LAG-3 immune-suppressive activity.

According to specific embodiments, the LAG-3 antagonist promotes immune response of an effector T cell following TCR activating signal.

According to specific embodiments, the LAG-3 antagonist of the present invention binds directly LAG-3 and/or binds ligands of LAG-3 and interferes with and/or inhibits the binding of the ligands to LAG-3.

According to other specific embodiments, the LAG-3 antagonist indirectly binds LAG-3 by acting through an intermediary molecule, for example the antagonist binds to or modulates a molecule that in turn binds to or modulates LAG-3.

According to specific embodiments, the LAG-3 antagonist binds LAG-3.

In certain embodiments, the LAG-3 antagonist exhibits one or more desirable functional properties, such as high affinity binding to LAG-3, e.g., binding to human LAG-3 with a $K_D$ of $10^{-7}$ M, $10^{-8}$ M, $10^{-9}$ M, $10^{-10}$ M or less; lack of significant cross-reactivity to other immune-check point proteins; the ability to stimulate T cell proliferation; the ability to increase IFN-γ, IL-4 and/or IL-2 secretion; the ability to inhibit binding of MHC class II to LAG-3; and/or the ability to inhibit growth of tumor cells.

According to a specific embodiment, the LAG-3 antagonist is an antibody.

According to specific embodiments, the LAG-3 antagonist is an anti-LAG-3 antibody. Anti-LAG-3 antibodies suitable for use in the invention can be generated using methods well known in the art especially in light of the detailed description hereinabove. Alternatively, art recognized anti-LAG-3 antibodies can be used. Examples of anti-LAG-3 antibodies are disclosed for example in Blackburn et al. (2009) Nat Immunol. 10(1): 29-37, Woo et al. (2012) Cancer Res, 72: 917-927, U.S. Pat. Nos. 6,143,273; 5,955,300; and RE38313, U.S. Application Publication No. 20110150892, International Application Publication Nos. WO2014008218; WO2014144666; WO2003035682; WO2011109789; and WO2014140180, which are hereby incorporated by reference in their entirety.

Specific anti-LAG-3 antibodies that can be used according to some embodiments of the present invention include, but are not limited to:

BMS-986016 (produced by BMS), a monoclonal antibody that binds LAG-3; and

IMP701 (produced by Immutep), an antagonist antibody that binds LAG-3.

According to a specific embodiment, the antibody competes with any of the above-mentioned antibodies for binding to LAG-3.

According to a specific embodiment, the antibody competes for binding with and/or binds to the same epitope on LAG-3 as the above-mentioned antibodies.

According to another specific embodiment, the antibody has at least about 90% variable region amino acid sequence identity with the above-mentioned antibodies.

Other LAG-3 antagonists that can be used according to some embodiments of the present invention include nucleotides, expression vectors, small molecules, peptides, fusion proteins and fragments targeting LAG-3, non-functional LAG-3 (such as LAG-3 molecule lacking the intracellular KIEELE domain), soluble LAG-3 or fragments thereof that bind to a LAG-3 ligand and prevent binding to the endogenous LAG-3 receptor, such as disclosed for example in Goldberg and Drake (2011) Curr Top Microbiol Immunol. 344:269-78, EP Patent No. EP0893507, U.S. Pat. No. 6,482, 925 and RE38313; U.S. Application Publication No. 20140271677, International Application Publication Nos: WO2003035682; WO2014012479; and WO2011109789, which are hereby incorporated by reference in their entirety.

According to an aspect of the present invention there is provided a method of treating cancer in a subject in need thereof, the method comprising:

(a) administering to the subject a therapeutically effective amount of a peptide having an amino acid sequence as set forth in SEQ ID NO:1 or an analog or derivative thereof; and (b) administering to the subject a therapeutically effective amount of a TIM-3 antagonist, thereby treating the cancer in the subject.

According to an aspect of the present invention there is provided an article of manufacture identified for use in treating cancer, comprising a packaging material packaging a peptide having an amino acid sequence as set forth in SEQ ID NO: 1 or an analog or derivative thereof and a TIM-3 antagonist.

According to an aspect of the present invention there is provided a pharmaceutical composition comprising as active ingredients a peptide having an amino acid sequence as set forth in SEQ ID NO: 1 or an analog or derivative thereof and a TIM-3 antagonist; and a pharmaceutically acceptable carrier or diluent.

TIM-3 is a type I transmembrane protein having a structurally conserved immunoglobulin variable (IgV) domain and a mucin domain expressed on the surface of several immune cells such as T cells (mainly Th1 cells) macrophages and dendritic cells. According to a specific embodiment the TIM-3 protein refers to the human protein, such as provided in the following GenBank Number NP_116171. A ligand for TIM-3 have been identified, glectin-9. It has been shown that galectin 9 is upregulated in various types of cancer, including breast cancer [Pardoll (2012) Nature Reviews Cancer 12, 252-264]. According to a specific embodiment the galectin-9 protein refers to the human protein, such as provided in the following GenBank Numbers NP_002299 and NP_033665.

Binding of TIM-3 to its ligand negatively regulates Th1 cell immunity by specifically inducing cell death in effector Th1 cells.

As used herein, the term "TIM-3 antagonist" refers to an antagonistic agent that prevents and/or inhibits the biological function and/or expression of TIM-3.

According to specific embodiments, the TIM-3 antagonist prevents and/or inhibits signaling to an immune cell (e.g. T cells, e.g. Th1 cells) by TIM-3; thereby suppresses TIM-3 immune-suppressive activity.

According to specific embodiments, the TIM-3 antagonist promotes immune response of an effector T cell (e.g. Th1 cells) following TCR activating signal.

According to specific embodiments, the TIM-3 antagonist of the present invention binds directly TIM-3 and/or that binds ligands of TIM-3 and interferes with and/or inhibits the binding of the ligands to TIM-3.

According to other specific embodiments, the TIM-3 antagonist indirectly binds TIM-3 by acting through an intermediary molecule, for example the antagonist binds to or modulates a molecule that in turn binds to or modulates TIM-3.

According to specific embodiments, the TIM-3 antagonist binds TIM-3.

According to other specific embodiments, the TIM-3 antagonist binds a TIM-3 ligand (e.g. galectin-9).

In certain embodiments, the TIM-3 antagonist exhibits one or more desirable functional properties, such as high affinity binding to TIM-3, e.g., binding to human TIM-3 with a $K_D$ of $10^{-7}$ M, $10^{-8}$ M, $10^{-9}$ M, $10^{-10}$ M or less; lack of significant cross-reactivity to other immune-check point proteins; the ability to increase Th1 mediated immune-response; the ability to stimulate T cell proliferation; the ability to increase IFN-γ secretion; the ability to inhibit binding of galectin-9 to TIM-3; and/or the ability to inhibit growth of tumor cells.

According to a specific embodiment, the TIM-3 antagonist is an antibody.

According to specific embodiments, the TIM-3 antagonist is an anti-TIM-3 antibody. Anti-TIM-3 antibodies suitable for use in the invention can be generated using methods well known in the art especially in light of the detailed description hereinabove. Alternatively, art recognized anti-TIM-3 antibodies can be used. Examples of anti-TIM3 antibodies are disclosed for example in Ngiow et al. (2011) Cancer Res 71:3540-51; Sakuishi et al. (2010) Exp Med 207: 2187-94 U.S. Pat. Nos. 8,647,623; 8,841,418; 8,709,412, U.S. Patent Application Publication No. 20120189617, International Application Publication Nos. WO2011159877; WO2005033144 and WO2014022332, which are hereby incorporated by reference in their entirety.

According to a specific embodiment, the antibody competes with any of the above-mentioned antibodies for binding to TIM-3.

According to a specific embodiment, the antibody competes for binding with and/or binds to the same epitope on TIM-3 as the above-mentioned antibodies.

According to another specific embodiment, the antibody has at least about 90% variable region amino acid sequence identity with the above-mentioned antibodies.

According to a specific embodiment, the TIM-3 antagonist is an anti-galectin-9 antibody.

Other TIM-3 antagonists that can be used according to specific embodiments of the present invention include nucleotides, expression vectors, small molecules, peptides, fusion proteins and fragments targeting TIM-3 or it's ligand, such as disclosed for examples in U.S. Pat. No. 8,709,412, U.S. Application Publication Nos: 20140271677; 20100061992, International Patent Application Publication Nos: WO2014022332; and WO2005033144, which are hereby incorporated by reference in their entirety.

It has also been suggested that CEACAM1 is a TIM-3 ligand, thus a TIM-3 antagonist can be an agent that prevents signaling mediated by the interaction of TIM-3 with CEACAM1 (see International Patent Application Publication No. WO2014022332).

According to an aspect of the present invention there is provided a method of treating cancer in a subject in need thereof, the method comprising:

(a) administering to the subject a therapeutically effective amount of a peptide having an amino acid sequence as set forth in SEQ ID NO:1 or an analog or derivative thereof; and (b) administering to the subject a therapeutically effective amount of a KIR antagonist, thereby treating the cancer in the subject.

According to an aspect of the present invention there is provided an article of manufacture identified for use in treating cancer, comprising a packaging material packaging a peptide having an amino acid sequence as set forth in SEQ ID NO: 1 or an analog or derivative thereof and a KIR antagonist.

According to an aspect of the present invention there is provided a pharmaceutical composition comprising as active ingredients a peptide having an amino acid sequence as set forth in SEQ ID NO: 1 or an analog or derivative thereof and a KIR antagonist; and a pharmaceutically acceptable carrier or diluent.

KIRs (killer cell Ig-like receptors) are cell surface glycoproteins, comprising one to three extracellular immunoglobulin-like domains, which are expressed by some T cells as well as most human NK cells. KIRs interact with determinants in the MHC class I molecules and upon interaction KIRs deliver an inhibitory or an activating signal. KIR genes are characterized by the number of Ig domains (2D or 3D) and by the length of their cytoplasmic tail: Long-tailed KIRs (2DL or 3DL) contain immuno-receptor tyrosine-based inhibition motifs (ITIMs), which recruit the phosphatase SHP-1 upon receptor engagement and induce inhibitory signals; Short-tailed KIRs (2DS or 3DS) lack ITIMs and send activating signals to NK cells by association with the adaptor signaling molecule DAP12 via a charged amino acid in the transmembrane region.

A number of KIRs are well characterized (see, e.g., Carrington and Norman, The KIR Gene Cluster, May 28, 2003, available through the National Center for Biotechnology Information (NCBI) web site at www(dot)ncbi(dot)nlm(dot)nih(dot)gov/books/bookres(dot)fcgi/mono_003/ch1d1(dot)pdf).

The sequences of human KIR genes and cDNAs, as well as their protein products, are available in public databases, including GenBank. Non-limiting exemplary GenBank entries of human KIRs have the following accession numbers: KIR2DL1: Genbank accession number U24076, NM_014218, AAR16197, L41267 or NP_055033; KIR2DL2: Genbank accession number U24075, L76669 or NP_055034; KIR2DL3: Genbank accession number U24074, L41268 or NP_056952; KIR2DL4: Genbank accession number X97229; and KIR3DL1: Genbank accession number L41269.

KIRs appear to interact with different subsets of MHC antigens depending upon the KIR subtype. In humans, for example, KIRs having two Ig domains (KIR2D) recognize HLA-C allotypes, KIR2DL2 and KIR2DL3 recognize an epitope shared by group 1 HLA-C allotypes, KIR2DL1 recognizes an epitope shared by the reciprocal group 2 HLA-C allotypes, and KIR3DL2 recognizes HLA-A3 and -A11. Typically, an individual cell (e.g. NK cell) expresses several different KIRs and specifically binds to certain MHC allotypes.

As used herein, the term "KIR" refers to a KIR that delivers an inhibitory signal to the cell. Typically, the inhibitory KIR has two or three extracellular Ig domains with a long intra-cytoplasmic tail (KIR2DL, KIR3DL).

According to specific embodiments, the KIR protein refers to KIR2DL1, KTR2DL2 and/or KTR2DL3.

As used herein, the term "KIR antagonist" refers to an antagonistic agent that prevents and/or inhibits the biological function and/or expression of KIR.

According to specific embodiments, the KIR antagonist prevents and/or inhibits signaling to an immune cell (e.g. NK cells) by KIR; thereby suppresses KIR immune-suppressive activity.

According to specific embodiments, the KIR antagonist promotes immune response of a NK cell.

The KIR antagonist of the present invention encompasses an antagonist that binds directly KIR and/or that binds ligands of KIR (e.g. NHC class I) and interferes with and/or inhibits the binding of the ligand to KIR.

According to specific embodiments, the KIR antagonist binds KIR.

According to a specific embodiment, the KIR antagonist binds a specific KIR with no cross-reactivity to other KIRs.

According to a specific embodiment, the KIR antagonist binds at least two, at least three different KIRs (e.g. human KIR receptors KIR2DL1, KIR2DL2, KIR2DL3).

According to other specific embodiments, the KIR antagonist binds at least one of an MHC class I allotype.

According to other specific embodiments, the KIR antagonist indirectly binds KIR by acting through an intermediary molecule, for example the antagonist binds to or modulates a molecule that in turn binds to or modulates KIR.

In certain embodiments, the KIR antagonist exhibits one or more desirable functional properties, such as high affinity binding to KIR, e.g., binding to human KIR2DL1, KTR2DL2 and/or KTR2DL3 with a $K_D$ of $10^{-7}$ M, $10^{-8}$ M, $10^{-9}$ M, $10^{-10}$ M or less; lack of significant cross-reactivity to other immune-check point proteins; the ability to stimulate NK cell cytotoxicity and/or the ability to inhibit growth of tumor cells.

According to a specific embodiment, the KIR antagonist is an antibody.

According to specific embodiments, the KIR antagonist is an anti-KIR antibody.

According to a specific embodiment, the anti-KIR antibody specifically binds one of the KIR receptors.

Anti-KIR antibodies suitable for use in the invention can be generated using methods well known in the art especially in light of the detailed description hereinabove. Alternatively, art recognized anti-KIR antibodies can be used. Examples of anti-KIR antibodies are disclosed for example in Romagne et al. (2009) Blood. 114: 2667-77, Vey et al. (2009) Blood 114: 632, International Patent Application Publication Nos. WO2014012479; WO2012160448; WO2006072625; WO2006003179; WO2006072626; WO2005003172; WO2005003168; WO2004056392; WO2005105849; WO2005009465; WO2005079766; WO2005003168; WO2005003172; WO2005037306 and WO2012160448, U.S. Patent Application Publication Nos. 20100189723; 20050037002, and U.S. Pat. No. 8,637,258, which are hereby incorporated by reference in their entirety.

Specific anti-KIR antibodies that can be used according to some embodiments of the present invention include, but are not limited to:

Lirilumab (also known as IPH2102; BMS-986015, produced by BMY), a fully human monoclonal antibody that binds KIR, specifically KIR2DL1/2/3; and IPH2101 (also known as 1-7F9, produced by Innate Pharma), a fully human IgG4 anti-KIR monoclonal antibody that binds KIR, specifically, KIR2DL1/2/3.

According to a specific embodiment, the antibody competes with any of the above-mentioned antibodies for binding to KIR.

According to a specific embodiment, the antibody competes for binding with and/or binds to the same epitope on KIR as the above-mentioned antibodies.

According to another specific embodiment, the antibody has at least about 90% variable region amino acid sequence identity with the above-mentioned antibodies.

Other KIR antagonists that can be used according to specific embodiments of the invention include nucleotides, expression vectors, small molecules, peptides, fusion proteins and fragments targeting KIR, such as disclosed for examples in U.S. Application Publication No. 20140271677; International Patent Application Publication No. WO2014012479; WO2012160448; and WO2006050270, and U.S. Patent Application Publication No. 20110091482, which are hereby incorporated by reference in their entirety.

Specific antagonistic peptides that can be used according to some embodiments of the present invention are VAPWNDAL and VAPWSNDYL, which were shown to be inhibitors of KIR2DL3 [Fadda et al. (2010) Proc Natl Acad Sci USA, 107(22):10160-5; and Gwenoline et al. (2013) J Immunol. 190(6): 2924-2930].

According to an aspect of the present invention there is provided a method of treating cancer in a subject in need thereof, the method comprising:

(a) administering to the subject a therapeutically effective amount of a peptide having an amino acid sequence as set forth in SEQ ID NO:1 or an analog or derivative thereof; and (b) administering to said subject a therapeutically effective amount of a IDO antagonist, thereby treating the cancer in the subject.

According to an aspect of the present invention there is provided an article of manufacture identified for use in treating cancer, comprising a packaging material packaging a peptide having an amino acid sequence as set forth in SEQ ID NO: 1 or an analog or derivative thereof and a IDO antagonist.

According to an aspect of the present invention there is provided a pharmaceutical composition comprising as active ingredients a peptide having an amino acid sequence as set forth in SEQ ID NO: 1 or an analog or derivative thereof and a IDO antagonist; and a pharmaceutically acceptable carrier or diluent.

IDO (indoleamine 2,3-dioxygenase), EC 1.13.11.52, is a heme-containing intracellular enzyme that catalyzes the first and rate-determining step in the degradation of the essential amino acid L-tryptophan to N-formyl-kynurenine.

According to a specific embodiment, the IDO protein refers to the human protein, such as provided in the following GenBank Number NP_002155.

Tryptophan is an amino acid which is essential for cell proliferation and survival. By locally depleting tryptophan and increasing proapoptotic kynurenines, IDO expressed by e.g. dendritic cells or tumor cells can affect immune cell (e.g. T-cell) proliferation and survival.

As used herein, the term "IDO antagonist" refers to an antagonistic agent that prevents and/or inhibits the biological function and/or expression of IDO. The term also encompasses antagonists of the IDO isoenzymes, including for example TDO (tryptophan (2,3)-dioxygenase) and/or ID02. Thus, the IDO antagonist for use in the present invention may inhibit, directly or indirectly, IDO and/or TDO and/or ID02.

Methods of evaluating IDO enzymatic activity are well known in the art and include e.g. measurement of the production kynurenine (the hydrolysis product of N-formyl-kynurenine) from tryptophan (see e.g. Daubener, W., et al. (1994) J. Immunol. Methods 168:39-47).

According to specific embodiments, the IDO antagonist prevents and/or inhibits deprivation of tryptophan and/or elevation of kyurenine from an immune cell (e.g. T cells); thereby prevents and/or inhibits the suppressive activity of IDO on an immune cell (e.g. T cells).

According to specific embodiments, the IDO antagonist binds IDO.

According to other specific embodiments, the IDO antagonist indirectly binds IDO by acting through an intermediary molecule, for example the antagonist binds to or modulates a molecule that in turn binds to or modulates IDO.

The IDO antagonist may be a reversible or an irreversible antagonist.

According to a specific embodiment, the IDO antagonist is a reversible antagonist i.e. reversibly inhibits IDO enzyme activity either at the catalytic site or at a non-catalytic site.

According to another specific embodiment, the IDO antagonist is an irreversible antagonist i.e. irreversibly destroys IDO enzymatic activity by forming a covalent bond with the enzyme.

Suitable IDO inhibitors include those based on natural products, such as the cabbage extract brassinin, the marine hydroid extract annulin B and the marine sponge extract exiguamine A, including synthetic derivatives thereof.

According to specific embodiments, the IDO antagonist is a small molecule. Such inhibitors include the tryptophan mimetic 1-methyl tryptophan (1-MT, see e.g. U.S. Pat. No. 8,383,613, the content of which are incorporated herein in its entirety). 1-MT occurs as two stereoisomers: the L isomer significantly inhibits IDOI, while the D isomer is more specific for ID02. Examples of other small molecules targeting IDO include, but are not limited to, oxadiazole and other heterocyclic IDO inhibitors which are disclosed in U.S. Patent Application Publication Nos. 20060258719 and 20070185165, alpha-methyl-tryptophan (disclosed in e.g. International Patent Application Publication No. WO2011100295), 1-methyl-DL-tryptophan, p-(3-benzofuranyl)-DL-alanine, p-[3-benzo(b)thienyl]-DL-alanine, and 6-nitro-L-tryptophan) [disclosed e.g. in Munn et al. (1999)], hydroxyanthranilic acid (disclosed e.g. in International Patent Application Publication No. WO2009063241), INCB24360 (a hydroxyamidine small-molecule inhibitor) and cannabinoids (disclosed e.g. in European Patent No. EP2341903). Other small molecules that can be used as IDO inhibitors are disclosed in International Patent Application Publication Nos. WO2014150677; WO2014150646; WO2014066834; WO2012142237; WO2008115804 and WO2004094409; WO2014081689; WO2008068621; WO2000066764, U.S. Patent Application Publication Nos. 20110053941, and U.S. Pat. Nos. 8,088,803; 8,748,469; 8,389,568; 7,799,776; 8,476,454; and 7,705,022, which are incorporated herein in their entirety.

Specific small molecules that can be used according to some embodiments of the present invention include, but are not limited to:

NLG919 (RG6078, produced by Roche);
F001287 (produced by BMY);
Indoximod (D-1MT/NLG8189, produced by NewLink Genetics);
NLG-919 (produced by NewLink Genetics); and
INCB-024360 (produced by Incyte).

Other IDO antagonists that can be used according to specific embodiments of the present invention include, but are not limited to, nucleotides, expression vectors, small molecules, peptides, antibodies, fusion proteins and fragments targeting IDO.

Exemplary expression vectors that can be used are disclosed in U.S. Application Publication No. 20140271677, which is hereby incorporated by reference it's their entirety.

Exemplary siRNA that can be used is disclosed in U.S. Pat. No. 8,389,708, which is hereby incorporated by reference it's their entirety.

Exemplary peptides that can be used are disclosed in U.S. Pat. No. 8,658,603, which is hereby incorporated by reference it's their entirety.

As the immune-check point protein can be a co-stimulatory protein, according to specific embodiments, wherein the immune-check protein is a co-stimulatory protein, the CXCR4 antagonistic peptides of the present invention are administered in combination with an immune-check point agonist. Following is a list of combinations that may be used in accordance with the present teachings.

According to an aspect of the present invention there is provided a method of treating cancer in a subject in need thereof, the method comprising:

(a) administering to the subject a therapeutically effective amount of a peptide having an amino acid sequence as set forth in SEQ ID NO:1 or an analog or derivative thereof; and (b) administering to the subject a therapeutically effective amount of a OX40 agonist, thereby treating the cancer in the subject.

According to an aspect of the present invention there is provided an article of manufacture identified for use in treating cancer, comprising a packaging material packaging a peptide having an amino acid sequence as set forth in SEQ ID NO: 1 or an analog or derivative thereof and a OX40 agonist.

According to an aspect of the present invention there is provided a pharmaceutical composition comprising as active ingredients a peptide having an amino acid sequence as set forth in SEQ ID NO: 1 or an analog or derivative thereof and a OX40 agonist; and a pharmaceutically acceptable carrier or diluent.

OX40 (also known as CD134, TNFRSF4) is a co-stimulatory receptor which belongs to the TNF receptor super family, expressed on the surface of several immune cells such as activated CD4+ and CD8+ TCR T cells. According to a specific embodiment, the OX40 protein refers to the human protein, such as provided in the following GenBank Number NP_003318. A ligand for OX40 has been identified, OX40L (also known as CD134L, CD252, TNFSF4). According to a specific embodiment, the OX40L protein refers to the human protein, such as provided in the following GenBank Number NP_003317.

As used herein, the term "OX40 agonist" refers to an agonistic agent that induces and/or increases the biological function and/or expression of OX40.

According to specific embodiments, the OX40 agonist induces and/or increases signaling to an immune cell (e e.g. T cells) by OX40; thereby induces and/or increases OX40 immune co-stimulatory activity.

According to specific embodiments, the OX40 agonist promotes immune response of an effector T cell (e.g. CD4+ and CD8+ T cell) following TCR activating signal.

According to specific embodiments, the OX40 agonist binds and activates OX40.

According to specific embodiments, the OX40 agonist binds ligands of OX40 and increases the binding (e.g. affinity) of the ligands to OX40 and/or activation of OX40 by the ligand.

According to other specific embodiments, the OX40 agonist indirectly binds OX40 by acting through an intermediary molecule, for example the agonist binds to or modulates a molecule that in turn binds to or modulates OX40.

In certain embodiments, the OX40 agonist exhibits one or more desirable functional properties, such as high affinity binding to OX40, e.g., binding to human OX40 with a $K_D$ of $10^{-7}$ M, $10^{-8}$ M, $10^{-9}$ M, $10^{-10}$ M or less; lack of significant cross-reactivity to other immune-check point proteins; the ability to stimulate T cell differentiation and/or proliferation; the ability to increase IFN-γ and/or IL-2 secretion; the ability to increase T cell cytotoxicity; the ability to generate memory T cells; the ability to inhibit regulatory T cell function and/or the ability to inhibit growth of tumor cells.

According to a specific embodiment, the OX40 agonist is the naturally occurring ligand (e.g. OX40L) or a functional derivative or variant thereof which retain the ability to specifically bind to the OX40. Thus, example, the OX40 agonist can be a entire OX40L, soluble OX40L or fragments thereof (e.g. a soluble molecule comprising the extracellular OX40L domains) and fusion proteins comprising a functionally active portion of OX40L covalently linked to a second protein domain, that binds to and activates OX40, such as described in U.S. Pat. Nos. 5,457,035; 7,622,444; 6,312,700 and International Patent Application Publication No. WO95/21915; which are hereby incorporated by reference in their entirety.

According to a specific embodiment, the OX40 agonist is an antibody.

According to specific embodiments, the OX40 agonist is an anti-OX40 antibody. Anti-OX40 antibodies suitable for use in the invention can be generated using methods well known in the art especially in light of the detailed description hereinabove. Alternatively, art recognized anti-OX40 antibodies can be used. Examples of anti-OX40 antibodies are disclosed for example in Weinberg, A. et al. (2000) Immunol 164: 2160-2169, Weinberg, A. D., et al. (2006) J Immunother 29, 575-585, International Patent Application Publication Nos. WO2011109789; WO2013038191; WO95/12673 and WO95/21915, and U.S. Pat. No. 7,504,101, which are hereby incorporated by reference in their entirety.

Specific anti-OX40 antibodies that can be used according to some embodiments of the present invention include, but are not limited to:

MOXR0916 (also known as RG7888, produced by Roche), a humanized monoclonal antibody that binds OX40;

MEDI0562 (produced by AZY/MedImmune), a humanized monoclonal antibody that binds OX40;

MEDI6469 (produced by AZY/MedImmune), a murine-based antibody that binds OX40; and 9B12 (described in Weinberg, A. D., et al. (2006) J. Immunother 29, 575-585], a murine IgG1 monoclonal antibody directed against the extracellular domain of human OX40.

According to a specific embodiment, the antibody competes with any of the above-mentioned antibodies for binding to OX40.

According to a specific embodiment, the antibody competes for binding with and/or binds to the same epitope on OX40 as the above-mentioned antibodies.

According to another specific embodiment, the antibody has at least about 90% variable region amino acid sequence identity with the above-mentioned antibodies.

According to other specific embodiments, the OX40 agonist is a fusion protein in which one or more domains of OX40L is covalently linked to one or more additional protein domains. Exemplary OX40L fusion proteins that can be used as OX40 agonists are described in U.S. Pat. Nos. 6,312,700; 7,622,444, International Patent Application Publication Nos. WO2011109789; and WO2010105068, the disclosures of which are incorporated herein by reference in their entirety.

According to specific embodiments, the OX40 agonist includes an OX40L fusion polypeptide that self-assembles into a multimeric (e.g., trimeric or hexameric) OX40L fusion protein. Such fusion proteins are described, e.g., in Morris et al. (2007) Mol Immunol. 44(12): 3112-3121, U.S. Pat. No. 7,959,925, which is incorporated by reference herein in its entirety.

According to specific embodiments, the OX40 agonist is a OX40 polypeptide agonist linked to an agonistic polypeptide of another co-stimulatory check point protein, for example, a polypeptide agonist for OX40 linked to a polypeptide agonist for CD40 or CD137, such as disclosed in International Patent Application Publication No. WO2014121099 and WO2012109203, respectively, which are incorporated by reference herein in their entirety.

A specific fusion protein that can be used according to some embodiments of the present invention is MEDI6383 (produced by AZY/MedImmune), a human OX40 ligand fusion protein.

Other OX40 agonists that can be used according to specific embodiments of the present invention include nucleotides, expression vectors and peptides, such as disclosed for example in Linch et al. (2015) Front Oncol. 5: 34, U.S. Pat. No. 6,312,700 and U.S. Application Publication No. 20140271677, which are hereby incorporated by reference in their entirety.

According to an aspect of the present invention there is provided a method of treating cancer in a subject in need thereof, the method comprising:

(a) administering to the subject a therapeutically effective amount of a peptide having an amino acid sequence as set forth in SEQ ID NO:1 or an analog or derivative thereof; and (b) administering to the subject a therapeutically effective amount of a CD137 agonist, thereby treating the cancer in the subject.

According to an aspect of the present invention there is provided an article of manufacture identified for use in treating cancer, comprising a packaging material packaging a peptide having an amino acid sequence as set forth in SEQ ID NO: 1 or an analog or derivative thereof and a CD137 agonist.

According to an aspect of the present invention there is provided a pharmaceutical composition comprising as active ingredients a peptide having an amino acid sequence as set forth in SEQ ID NO: 1 or an analog or derivative thereof and a CD137 agonist; and a pharmaceutically acceptable carrier or diluent.

CD137 (also known as 4-1BB and TNFRSF9), a member of the tumor necrosis factor receptor superfamily of co-stimulatory molecules, is a membrane glycoprotein that is inducibly expressed on several immune cells such as activated T cells, B cells, dendritic cells and natural killer (NK) cells. According to a specific embodiment the CD137 protein refers to the human protein, such as provided in the following GenBank Number NP_001552. A ligand for CD137 have been identified, CD137L (also known as 4-1BBL and TNFSF9), which is expressed on activated antigen-presenting cells, myeloid progenitor cells, and hematopoietic stem cells.

According to a specific embodiment the CD137L protein refers to the human protein, such as provided in the following GenBank Number NP_003802.

The interaction of CD137 with its ligand has been shown to co-stimulate proliferation of T lymphocytes, enhances B cells proliferation and immunoglobulin synthesis, also induces proliferation of monocytes.

As used herein, the term "CD137 antagonist" refers to an agonistic agent that induces and/or increases the biological function and/or expression of CD137.

According to specific embodiments, the CD137 agonist induces and/or increases signaling to an immune cell (e.g. T cells) by CD137; thereby induces and/or increases CD137 immune co-stimulatory activity.

According to specific embodiments, the CD137 agonist promotes immune response of an effector T cell following TCR activating signal.

According to specific embodiments, the CD137 agonist binds directly CD137 and activates the receptor.

According to specific embodiments, the CD137 agonist binds ligands of CD137 and increases the binding (e.g. affinity) of the ligands to CD137 and/or activation of CD137 by the ligand.

According to other specific embodiments, the CD137 agonist indirectly binds CD137 by acting through an intermediary molecule, for example the agonist binds to or modulates a molecule that in turn binds to or modulates CD137.

In certain embodiments, the CD137 agonist exhibits one or more desirable functional properties, such as high affinity binding to CD137, e.g., binding to human CD137 with a $K_D$ of $10^{-7}$ M, $10^{-8}$ M, $10^{-9}$ M, $10^{-10}$ M or less; lack of significant cross-reactivity to other immune-check point proteins; the ability to stimulate T cell proliferation; the ability to increase IFN-γ secretion; the ability to increase T cells cytotoxic activity; the ability to prevent activation induced cell death; and/or the ability to inhibit growth of tumor cells.

According to a specific embodiment, the CD137 agonist is the naturally occurring ligand (e.g. CD137L) or a functional derivative or variant thereof which retain the ability to specifically bind to the CD137. Thus, for example the GITR agonist can be an entire CD137L, soluble CD137L or fragments thereof and fusion proteins comprising a functionally active portion of CD137L covalently linked to a second protein domain, that binds to and activates CD137.

According to a specific embodiment, the CD137 agonist is an antibody.

According to specific embodiments, the CD137 agonist is an anti-CD137 antibody. Anti-CD137 antibodies suitable for use in the invention can be generated using methods well known in the art especially in light of the detailed description hereinabove. Alternatively, art recognized anti-CD137 antibodies can be used. Examples of anti-CD137 antibodies are disclosed for example in Melero, I. et al. (1997) Nature Medicine 3: 682-685 (1997), International Patent Application Publication Nos. WO2014144666; WO2006088447; WO2006088464; U.S. Patent Application Publication Nos. 20080166336; 20050095244, U.S. Pat. Nos. 7,214,493; 6,887,673; 8,337,850; 8,821,867; 7,288,638; 6,303,121; 6,569,997; 6,905,685; 6,355,476; 6,362,325; 6,974,863; 6,210,669; 5,928,893, which are hereby incorporated by reference in their entirety.

Specific anti-CD137 antibodies that can be used according to some embodiments of the present invention include, but are not limited to:

BMS-666513 (also known as urelumab, produced by BMY), a fully human $IgG_4$ monoclonal antibody that binds human CD137;

BMS-663031, BMS-469492; or BMS-469497; (produced by BMY, described in U.S. Pat. Nos. 7,288,638; and 6,362,325;

XmAb-5592 (Xencor); a Fc-engineered and humanized anti-CD137 antibody; and

PF-05082566 (produced by Pfizer), a fully human IgG2 monoclonal antibody that binds to the extracellular domain of human CD137.

According to a specific embodiment, the antibody competes with any of the above-mentioned antibodies for binding to CD137.

According to a specific embodiment, the antibody competes for binding with and/or binds to the same epitope on CD137 as the above-mentioned antibodies.

According to another specific embodiment, the antibody has at least about 90% variable region amino acid sequence identity with the above-mentioned antibodies.

According to other specific embodiments, the CD137 agonist is a fusion protein in which one or more domains of CD137L is covalently linked to one or more additional protein domains. Exemplary CD137 fusion proteins that can be used as CD137 agonists are described in International Application Publication No. WO2014012479; WO2011109789; WO2012109203, which are hereby incorporated by reference in their entirety.

According to specific embodiments, the CD137 agonist is a CD137 polypeptide agonist linked to an agonistic polypeptide of another co-stimulatory check point protein, for example, a polypeptide agonist for CD137 linked to a polypeptide agonist for e.g. OX40, CD40, ICOS, CD28, CD27, CD70 and GITR such as disclosed in International Patent Application Publication No. WO2012109203, which is incorporated by reference herein in its entirety.

According to other specific embodiments, the CD137 agonist is an aptamer. Exemplary aptamers that can be used as CD137 agonists are described in McNamara et al. (2008) J. Clin. Invest. 1 18: 376-386 and International Application Publication No. WO2007035518, which are hereby incorporated by reference in their entirety.

Other CD137 agonists that can be used according to some embodiments of the present invention include nucleotides and expression vectors such as disclosed for examples in U.S. Application Publication No. 20140271677, which is hereby incorporated by reference in its entirety.

It has also been suggested that galectin-9 is a CD137 ligand, thus a CD137 agonist can be an agent that promotes signaling mediated by the interaction of CD137 with galectin-9 (see International Patent Application Publication No. WO2012177788).

According to an aspect of the present invention there is provided a method of treating cancer in a subject in need thereof, the method comprising:

(a) administering to the subject a therapeutically effective amount of a peptide having an amino acid sequence as set forth in SEQ ID NO:1 or an analog or derivative thereof; and (b) administering to the subject a therapeutically effective amount of a CD27 agonist, thereby treating the cancer in the subject.

According to an aspect of the present invention there is provided an article of manufacture identified for use in treating cancer, comprising a packaging material packaging a peptide having an amino acid sequence as set forth in SEQ ID NO: 1 or an analog or derivative thereof and a CD27 agonist.

According to an aspect of the present invention there is provided a pharmaceutical composition comprising as active ingredients a peptide having an amino acid sequence as set forth in SEQ ID NO: 1 or an analog or derivative thereof and a CD27 agonist; and a pharmaceutically acceptable carrier or diluent.

CD27 (also known as TNFRSF7, S152), a member of the tumor necrosis factor receptor superfamily, is a type I transmembrane protein expressed on the surface of several immune cells such as T cells, B cells and NK cells. According to a specific embodiment, the CD27 protein refers to the human protein, such as provided in the following GenBank Number NP_001233. A ligand for CD27 has been identified, CD70 (also known as TNFSF7). CD70 is transiently expressed following cell activation on dendritic cells, T cells, B cells and NK cells; and also on a variety of transformed cells including lymphoma B cells, Hodgkin's and Reed-Sternberg cells, malignant cells of neural origin, and a number of carcinomas. According to a specific embodiment the CD70 protein refers to the human protein, such as provided in the following GenBank Number NP_001243.

The interaction of CD27 with its ligand has been shown to activate the NF-kp signaling pathways that in turn stimulates B cell and T cell proliferation, cytokine secretion, plasma cell differentiation and subsequent antibody secretion (see e.g. Yamamoto, H. 1998 J Immunol. 161(9): 4753-9).

As used herein, the term "CD27 antagonist" refers to an agonistic agent that induces and/or increases the biological function and/or expression of CD27.

According to specific embodiments, the CD27 agonist induces and/or increases signaling to an immune cell (e.g. T cells, B cells, NK cells) by CD27; thereby induces and/or increases CD27 immune co-stimulatory activity.

According to specific embodiments, the CD27 agonist promotes immune response of an effector T cell following TCR activating signal.

According to specific embodiments, the CD27 agonist promotes immune response of a B cell.

According to specific embodiments, the CD27 agonist binds directly CD27 and activates the receptor.

According to specific embodiments, the CD27 agonist binds ligands of CD27 and increases the binding (e.g. affinity) of the ligands to CD27 and/or activation of CD27 by the ligand.

According to other specific embodiments, the CD27 agonist indirectly binds CD27 by acting through an intermediary molecule, for example the agonist binds to or modulates a molecule that in turn binds to or modulates CD27.

In certain embodiments, the CD27 agonist exhibits one or more desirable functional properties, such as high affinity binding to CD27, e.g., binding to human CD27 with a $K_D$ of $10^{-7}$ M, $10^{-8}$ M, $10^{-9}$ M, $10^{-10}$ M or less; lack of significant cross-reactivity to other immune-check point proteins; the ability to stimulate T cell proliferation; the ability to increase IFN-γ, IL-4 and/or IL-2 secretion; the ability to stimulate antigen-specific memory responses; the ability to stimulate antibody responses and/or the ability to inhibit growth of tumor cells.

According to a specific embodiment, the CD27 agonist is the naturally occurring ligand (e.g. CD70) or a functional derivative or variant thereof which retain the ability to specifically bind to the CD27. Thus, for example the CD27 agonist can be an entire CD70, soluble CD70 or fragments thereof and fusion proteins comprising a functionally active portion of CD70 covalently linked to a second protein domain, that binds to and activates CD27.

According to a specific embodiment, the CD27 agonist is an antibody.

According to specific embodiments, the CD27 agonist is an anti-CD27 antibody. Anti-CD27 antibodies suitable for use in the invention can be generated using methods well known in the art especially in light of the detailed description hereinabove. Alternatively, art recognized anti-CD27 antibodies can be used.

Examples of anti-CD27 antibodies are disclosed for example in Van Lier et al., 1987, J Immunol 139:1589-96, International Patent Application Publication Nos. WO2012004367; and WO2008/051424, U.S. Patent Application Publication Nos. 20120213771; and 20120093805, which are hereby incorporated by reference in their entirety.

Specific anti-CD27 antibodies that can be used according to some embodiments of the present invention include, but are not limited to:

Varlilumab (also known as CDX-1127, produced by Celldex), a fully human monoclonal antibody that binds CD27.

According to a specific embodiment, the antibody competes with any of the above-mentioned antibodies for binding to CD27.

According to a specific embodiment, the antibody competes for binding with and/or binds to the same epitope on CD27 as the above-mentioned antibodies.

According to another specific embodiment, the antibody has at least about 90% variable region amino acid sequence identity with the above-mentioned antibodies.

Other CD27 agonists that can be used according to some embodiments of the present invention include nucleotides and expression vectors, such as disclosed for examples in U.S. Application Publication No. 20140271677, which are hereby incorporated by reference in their entirety.

According to an aspect of the present invention there is provided a method of treating cancer in a subject in need thereof, the method comprising:

(a) administering to the subject a therapeutically effective amount of a peptide having an amino acid sequence as set forth in SEQ ID NO:1 or an analog or derivative thereof; and (b) administering to the subject a therapeutically effective amount of a CD40 agonist, thereby treating the cancer in the subject.

According to an aspect of the present invention there is provided an article of manufacture identified for use in treating cancer, comprising a packaging material packaging a peptide having an amino acid sequence as set forth in SEQ ID NO: 1 or an analog or derivative thereof and a CD40 agonist.

According to an aspect of the present invention there is provided a pharmaceutical composition comprising as active ingredients a peptide having an amino acid sequence as set forth in SEQ ID NO: 1 or an analog or derivative thereof and a CD40 agonist; and a pharmaceutically acceptable carrier or diluent.

CD40 is a co-stimulatory receptor expressed on the surface of several immune cells such as antigen presenting cells. According to a specific embodiment the CD40 protein refers to the human protein, such as provided in the following GenBank Number NP_001241. A ligand for CD40 has been identified, CD40L (also known as CD154), which is mainly expressed on T cells. According to a specific embodiment the CD40L protein refers to the human protein, such as provided in the following GenBank Number NP_000065.

The interaction of CD40 with its ligand has been shown to enhance antigen presenting cells maturation, antigen-presenting function, co-stimulatory potential and stimulate cytolytic activity of immune cells. Specifically, CD40 engagement increases release of immunoregulatory cytokines such as IL-6 IL-12 IL-15, increased expression of MHC class I and II, and increased expression of adhesion molecules (e.g., ICAM) and costimulatory molecules (e.g., B7).

In addition to enhancement of cellular and immune function, the effects of CD40 activation induce apoptosis of CD40 positive cells.

As used herein, the term "CD40 agonist" refers to an agonistic agent that induces and/or increases the biological function and/or expression of CD40.

According to specific embodiments, the CD40 agonist induces and/or increases signaling to an immune cell (e.g. B cell, dendritic cells) by CD40; thereby induces and/or increases CD40 immune co-stimulatory activity.

According to specific embodiments, the CD40 agonist promotes immune response of an immune cell e.g. dendritic cell, B cell, NK cell and/or effector T cell.

According to specific embodiments, the CD40 agonist promotes cell death of a CD40 positive cell.

According to specific embodiments, the CD40 agonist binds directly CD40 and activates the receptor.

According to specific embodiments, the CD40 agonist binds a ligand of CD40 and increases the binding (e.g. affinity) of the ligand to CD40 and/or activation of CD40 by the ligand.

According to other specific embodiments, the CD40 agonist indirectly binds CD40 by acting through an intermediary molecule, for example the agonist binds to or modulates a molecule that in turn binds to or modulates CD40.

In certain embodiments, the CD40 agonist exhibits one or more desirable functional properties, such as high affinity binding to CD40, e.g., binding to human CD40 with a $K_D$ of $10^{-7}$ M, $10^{-8}$ M, $10^{-9}$ M, $10^{-10}$ M or less; lack of significant cross-reactivity to other immune-check point proteins; the ability to increase IL-8, IL-12, IL-15, IL-18 and IL-23 secretion; the ability to enhance tumor antigen processing and presentation by dendritic cells, the ability to increase the cytolytic activity of T cells and NK cells; the ability to induces cell death of CD40 positive cells; the ability to stimulate antibody responses; and/or the ability to inhibit growth of tumor cells.

According to a specific embodiment, the CD40 agonist is the naturally occurring ligand (e.g. CD40L) or a functional derivative or variant thereof which retain the ability to specifically bind to the CD40. Thus, for example the CD40 agonist can be an entire CD40L, soluble CD40L or fragments thereof and fusion proteins comprising a functionally active portion of CD40L covalently linked to a second protein domain, that binds to and activates CD40, such as described in U.S. Pat. Nos. 6,410,711; 6,391,637; 5,981,724; 5,961,974, U.S. Patent Application Publication No. 20040006006, and International Application Publication Nos. WO2001016180; WO1996026735; WO1993008207, which are hereby incorporated by reference in their entirety.

According to a specific embodiment, the CD40 agonist is an antibody.

According to specific embodiments, the CD40 agonist is an anti-CD40 antibody. Agonistic anti-CD40 antibodies can exert their function by at least one of several mechanisms, including immune-enhancing effect by co-stimulation of CD40 positive cells, as well as direct killing of CD40 positive cells by induction of apoptosis or by stimulating a humoral response leading to ADCC. Anti-CD40 antibodies suitable for use in the invention can be generated using methods well known in the art especially in light of the detailed description hereinabove. Alternatively, art recognized anti-CD40 antibodies can be used. Examples of anti-CD40 antibodies are disclosed for example in Schlossman et al., Leukocyte Typing, 1995, 1:547-556, Hirano A. et al., Blood 93:2999-3007 (1999), French R. R. et al., Nature Medicine 5:548-53 (1999), Tutt A. L. et al., J. of Immunol. 161:3176-85 (1998), Funakoshi S. et al., J. of Immunotherapy with Emphasis on Tumor Immunol. 19:93-101 (1996), International Patent Application Publication Nos. WO2003040170; WO2005063289; WO2013034904; WO2003040170; WO2014070934; WO2012149356; WO2001037870, U.S. Patent Application Publication Nos. 20110311525; 20120263732; 20120263732; 20030059427; 20090074711; 20130024956; 20100098694 and U.S. Pat. Nos. 7,563,442; 7,338,660, 6,843,989, 7,172,759; 7,547, 438; 8,778,345; 8,388,971; 7,288,251; 7,618,633, which are hereby incorporated by reference in their entirety.

Specific anti-CD40 antibodies that can be used according to some embodiments of the present invention include, but are not limited to:

CP-870,893 (produced by Pfizer), a fully human IgG2 monoclonal antibody that binds CD40;

Dacetuzumab (produced by Seattle Genetics Inc), a humanized monoclonal antibody that binds CD40;

ADC-1013 (produced by Alligator Bioscience AB), a human monoclonal IgG1 anti-CD40 antibody; and CD40.4 (5C3, produced by PharMingen).

According to a specific embodiment, the antibody competes with any of the above-mentioned antibodies for binding to CD40.

According to a specific embodiment, the antibody competes for binding with and/or binds to the same epitope on CD40 as the above-mentioned antibodies.

According to another specific embodiment, the antibody has at least about 90% variable region amino acid sequence identity with the above-mentioned antibodies.

According to other specific embodiments, the CD40 agonist is a fusion protein in which one or more domains of CD40L is covalently linked to one or more additional protein domains. According to specific embodiments, the CD40 agonist includes a multimeric CD40L fusion polypeptide. Exemplary CD40L fusion proteins that can be used as CD40 agonists are described in International Patent Application Publication Nos: WO2007120368, WO2001016180, the disclosures of which are incorporated herein by reference in their entirety.

According to specific embodiments, the CD40 agonist is a CD40 polypeptide agonist linked to an agonistic polypeptide of another co-stimulatory check point protein, for example, a polypeptide agonist for CD40 linked to a polypeptide agonist for CD40, such as disclosed in International Patent Application Publication No. WO2014121099, which is incorporated by reference herein in its entirety.

Other CD40 agonists that can be used according to some embodiments of the present invention include nucleotides, expression vectors, polypeptides, small molecules, and methods of obtaining them, such as disclosed for examples in U.S. Application Publication Nos. 20140271677; and 20060287229 and International Application Publication No. WO2001016180, which are hereby incorporated by reference in their entirety.

According to an aspect of the present invention there is provided a method of treating cancer in a subject in need thereof, the method comprising:

(a) administering to the subject a therapeutically effective amount of a peptide having an amino acid sequence as set forth in SEQ ID NO: 1 or an analog or derivative thereof; and (b) administering to the subject a therapeutically effective amount of a GITR agonist, thereby treating the cancer in the subject.

According to an aspect of the present invention there is provided an article of manufacture identified for use in treating cancer, comprising a packaging material packaging a peptide having an amino acid sequence as set forth in SEQ ID NO: 1 or an analog or derivative thereof and a GITR agonist.

According to an aspect of the present invention there is provided a pharmaceutical composition comprising as active ingredients a peptide having an amino acid sequence as set forth in SEQ ID NO: 1 or an analog or derivative thereof and a GITR agonist; and a pharmaceutically acceptable carrier or diluent.

GITR [glucocorticoid-induced tumor necrosis factor receptor, also known as TNF receptor superfamily 18 (TNFRSF18)] is a type I transmembrane protein expressed on the surface of several immune cells such as T cells, NK cells, macrophages, B cells, dendritic cells, mast cells and monocytes. GITR expression on T cells is upregulated upon T cell activation. According to a specific embodiment the GITR protein refers to the human protein, such as provided in the following GenBank Numbers NP_004186, NP_683699, NP_683700. A ligand for GITR has been identified, GITRL (also known as TNFSF18). GITRL is a type II transmembrane protein as is typical for most TNF ligand family members, expressed primarily on antigen presenting cells including macrophages, B cells, dendritic cells and endothelial cells. According to a specific embodiment the GITRL protein refers to the human protein, such as provided in the following GenBank Number NP_005083.

It has been shown that the interaction of GITR with its ligand triggers a co-stimulatory signal which enhances effector T cells proliferation, survival and effector functions while inhibits the suppressive activity of regulatory T cells.

As used herein, the term "GITR agonist" refers to an agonistic agent that induces and/or increases the biological function and/or expression of GITR.

According to specific embodiments, the GITR agonist induces and/or increases signaling to an immune cell (e.g. T cells) by GITR; thereby induces and/or increases GITR immune co-stimulatory activity.

According to specific embodiments, the GITR agonist promotes immune response of an effector T cell following TCR activating signal.

According to specific embodiments, the GITR agonist binds directly GITR and activates the receptor.

According to specific embodiments, the GITR agonist binds ligands of GITR and increases the binding (e.g. affinity) of the ligands to GITR and/or activation of GITR by the ligand.

According to other specific embodiments, the GITR agonist indirectly binds GITR by acting through an intermediary molecule, for example the agonist binds to or modulates a molecule that in turn binds to or modulates GITR.

In certain embodiments, the GITR agonist exhibits one or more desirable functional properties, such as high affinity binding to GITR, e.g., binding to human GITR with a $K_D$ of $10^{-7}$ M, $10^{-8}$ M, $10^{-9}$ M, $10^{-10}$ M or less; lack of significant cross-reactivity to other immune-check point proteins; lack of significant reactivity to other tumor necrosis factor receptors; the ability to stimulate T cell proliferation; the ability to stimulate antibody responses and/or the ability to inhibit growth of tumor cells.

According to a specific embodiment, the GITR agonist is the naturally occurring ligand (e.g. GITRL) or a functional derivative or variant thereof which retain the ability to specifically bind to the GITR. Thus, for example the GITR agonist can be an entire GITRL, soluble GITRL or fragments thereof and fusion proteins comprising a functionally active portion of GITRL covalently linked to a second protein domain, that binds to and activates GITR, such as described in International Patent Application Publication No. WO2005007190, the contents of which is hereby incorporated by reference in their entirety.

According to a specific embodiment, the GITR agonist is an antibody.

According to specific embodiments, the GITR agonist is an anti-GITR antibody. Anti-GITR antibodies suitable for use in the invention can be generated using methods well known in the art especially in light of the detailed description hereinabove. Alternatively, art recognized anti-GITR antibodies can be used. Examples of anti-GITR antibodies are disclosed for example in International Patent Application Publication Nos. WO2005007190; WO2011109789; WO2013039954; WO2015031667, U.S. Patent Application Publication Nos. 20070098719; 20140348841; 20140220002, U.S. Pat. Nos. 8,709,424; 8,591,886; 7,618,632; 7,812,135; and 8,388,967, which are hereby incorporated by reference in their entirety.

Specific anti-GITR antibodies that can be used according to some embodiments of the present invention include, but are not limited to:

MK-4166 (produced by Merck), a monoclonal antibody that binds GITR; and

TRX518 (produced by GITR Inc.), a humanized monoclonal antibody that binds human GITR.

According to a specific embodiment, the antibody competes with any of the above-mentioned antibodies for binding to GITR.

According to a specific embodiment, the antibody competes for binding with and/or binds to the same epitope on GITR as the above-mentioned antibodies.

According to another specific embodiment, the antibody has at least about 90% variable region amino acid sequence identity with the above-mentioned antibodies.

According to other specific embodiments, the GITR agonist is a fusion protein in which one or more domains of GITRL is covalently linked to one or more additional protein domains. Exemplary GITRL fusion proteins that can be used as GITR agonists are described in International Patent Application Publication No. WO2011109789, the contents of which are incorporated herein by reference in their entirety.

According to specific embodiments, the GITR agonist includes a multimeric GITRL fusion polypeptide, such as disclosed for examples in International Patent Application Publication No. WO2007120368, which is incorporated by reference herein in its entirety.

Other GITR agonists that can be used according to some embodiments of the present invention include nucleotides, expression vectors, small molecules and peptides such as disclosed for examples in U.S. Application Publication No. 20140271677, U.S. Pat. Nos. 7,618,632; 8,586,023, which are hereby incorporated by reference in their entirety.

According to an aspect of the present invention there is provided a method of treating cancer in a subject in need thereof, the method comprising:

(a) administering to the subject a therapeutically effective amount of a peptide having an amino acid sequence as set forth in SEQ ID NO: 1 or an analog or derivative thereof; and (b) administering to said subject a therapeutically effective amount of a CD28 agonist, thereby treating the cancer in the subject.

According to an aspect of the present invention there is provided an article of manufacture identified for use in treating cancer, comprising a packaging material packaging a peptide having an amino acid sequence as set forth in SEQ ID NO: 1 or an analog or derivative thereof and a CD28 agonist.

According to an aspect of the present invention there is provided a pharmaceutical composition comprising as active ingredients a peptide having an amino acid sequence as set forth in SEQ ID NO: 1 or an analog or derivative thereof and a CD28 agonist; and a pharmaceutically acceptable carrier or diluent.

CD28 is a co-stimulatory molecule expressed on the surface of several immune cells such as T cells. According to a specific embodiment the CD28 protein refers to the human protein, such as provided in the following GenBank Numbers NP_001230006, NP_001230007, NP_006130. Several ligands for CD28 have been identified, B7.1 (also known as CD80) and B7.2 (also known as CD86). According to a specific embodiment the B7.1 protein refers to the human protein, such as provided in the following GenBank Number NP_005182. According to a specific embodiment the B7.2 protein refers to the human protein, such as provided in the following GenBank Number NP_001193853.

The interaction of CD28 with its ligand triggers a co-stimulatory signal that synergizes with the TCR signal to promote T-cell activation, proliferation and function. CD28 signaling was shown to regulate the threshold for T-cell activation and decrease the number of TCR engagements needed for T-cell activation.

As used herein, the term "CD28 agonist" refers to an agonistic agent that induces and/or increases the biological function and/or expression of CD28.

According to specific embodiments, the CD28 agonist induces and/or increases signaling to an immune cell (e.g. T cells) by CD28; thereby induces and/or increases CD28 immune co-stimulatory activity.

According to specific embodiments, the CD28 agonist promotes immune response of an effector T cell following TCR activating signal.

According to specific embodiments, the CD28 agonist binds directly CD28 and activates the receptor.

According to specific embodiments, the CD28 agonist binds ligands of CD28 (e.g. B7.1 and B7.2) and increases the binding (e.g. affinity) of the ligands to CD28 and/or activation of CD28 by the ligand.

According to other specific embodiments, the CD28 agonist indirectly binds CD28 by acting through an intermediary molecule, for example the agonist binds to or modulates a molecule that in turn binds to or modulates CD28.

In certain embodiments, the CD28 agonist exhibits one or more desirable functional properties, such as high affinity binding to CD28, e.g., binding to human CD28 with a $K_D$ of $10^{-7}$ M, $10^{-8}$ M, $10^{-9}$ M, $10^{-10}$ M or less; lack of significant cross-reactivity to other immune-check point proteins, e.g., CTLA-4 and ICOS; the ability to stimulate T cell proliferation; the ability to increase IFN-γ and/or IL-2 secretion; the ability to stimulate antigen-specific memory responses; the ability to stimulate antibody responses and/or the ability to inhibit growth of tumor cells.

According to a specific embodiment, the CD28 agonist is the naturally occurring ligand (e.g. B7.1 or B7.2) or a functional derivative or variant thereof which retain the ability to specifically bind to the CD28. Thus, for example the CD28 agonist can be an entire B7.1 or B7.2, soluble B7.1 or B7.2 or fragments thereof and fusion proteins comprising a functionally active portion of B7.1 or B7.2 covalently linked to a second protein domain, that binds to and activates CD28, such as disclosed for example in U.S. Patent Application Publication No. 20030232323; and International Application Publication No. WO1995003408, which are hereby incorporated by reference in their entirety.

According to specific embodiments, the B7.1 or B7.2 functional derivative or variant specifically binds CD28 with not cross reactivity to CTLA4.

According to a specific embodiment, the CD28 agonist is an antibody.

According to specific embodiments, the CD28 agonist is an anti-CD28 antibody. The anti-CD28 antibody can be a superagonistic anti-CD28 antibody or a conventional anti-CD28 antibody.

As used herein, the phrase "conventional anti-CD28 antibody" refers to an antibody which binds CD28 (e.g., in a domain outside the basolateral domain) and co-stimulates T cells in a TCR-dependent mechanism.

As used herein, the phrase "superagonistic anti-CD28 antibody" refers to an antibody which binds CD28 through the basolateral domain resulting in a polyclonal activation of T lymphocytes even in the absence of TCR stimulation.

Anti-CD28 antibodies suitable for use in the invention can be generated using methods well known in the art especially in light of the detailed description hereinabove. Alternatively, art recognized anti-CD28 antibodies can be used. Examples of anti-CD28 antibodies are disclosed for example in Poirier et al. (2012) American Journal of Transplantation 12(7): 1682-1690, Cell Immunol. 2005 July-August; 236(1-2): 154-60, which are hereby incorporated by reference in their entirety.

Specific anti-CD28 antibodies that can be used according to some embodiments of the present invention include, but are not limited to TAB08 (previously known as TGN1412, produced by TheraMAB), a humanized monoclonal antibody directed against human CD28.

According to a specific embodiment, the antibody competes with any of the above-mentioned antibodies for binding to CD28.

According to a specific embodiment, the antibody competes for binding with and/or binds to the same epitope on CD28 as the above-mentioned antibodies.

According to another specific embodiment, the antibody has at least about 90% variable region amino acid sequence identity with the above-mentioned antibodies.

According to other specific embodiments, the CD28 agonist is an aptamer. Exemplary aptamers that can be used as CD28 agonists are described in Pastor et al. Mol Ther Nucleic Acids. (2013) Jun. 11; 2:e98, which is hereby incorporated by reference in its entirety.

According to specific embodiments, other CD28 agonists include nucleotides, expression vectors, small molecules, peptides, fusion proteins and fragments targeting CD28, are disclosed for examples in U.S. Application Publication Nos. 20140271677; 20040137577; 20020106730; 20100303811 and International Application Publication No. WO2014089009 which are hereby incorporated by reference in their entirety.

According to an aspect of the present invention there is provided a method of treating cancer in a subject in need thereof, the method comprising:

(a) administering to the subject a therapeutically effective amount of a peptide having an amino acid sequence as set forth in SEQ ID NO: 1 or an analog or derivative thereof; and (b) administering to said subject a therapeutically effective amount of a ICOS agonist, thereby treating the cancer in the subject.

According to an aspect of the present invention there is provided an article of manufacture identified for use in treating cancer, comprising a packaging material packaging a peptide having an amino acid sequence as set forth in SEQ ID NO: 1 or an analog or derivative thereof and a ICOS agonist.

According to an aspect of the present invention there is provided a pharmaceutical composition comprising as active ingredients a peptide having an amino acid sequence as set forth in SEQ ID NO: 1 or an analog or derivative thereof and a ICOS agonist; and a pharmaceutically acceptable carrier or diluent.

ICOS (also known as CD278) is a co-stimulatory molecule expressed on the surface of several immune cells such as activated T cells. According to a specific embodiment the ICOS protein refers to the human protein, such as provided in the following GenBank Number NP_036224. A ligand for ICOS has been identified, ICOSL (also known as B7-H2, B7RP1, CD275). According to a specific embodiment the ICOSL protein refers to the human protein, such as provided in the following GenBank Numbers NP_001269979, NP_001269980, NP_001269981, NP_056074. The interaction of ICOS with its ligand triggers a co-stimulatory signal that promotes T-helper cell differentiation and effector function, and is particularly important for interleukin-10 (IL-10) production.

As used herein, the term "ICOS agonist" refers to an agonistic agent that induces and/or increases the biological function and/or expression of ICOS.

According to specific embodiments, the ICOS agonist induces and/or increases signaling to an immune cell (e.g. T cells) by ICOS; thereby induces and/or increases ICOS immune co-stimulatory activity.

According to specific embodiments, the ICOS agonist promotes immune response of an effector T cell following TCR activating signal.

According to specific embodiments, the ICOS agonist binds directly ICOS and activates the receptor.

According to specific embodiments, the ICOS agonist binds ligands of ICOS and increases the binding (e.g. affinity) of the ligands to ICOS and/or activation of ICOS by the ligand.

According to other specific embodiments, the ICOS agonist indirectly binds ICOS by acting through an intermediary molecule, for example the agonist binds to or modulates a molecule that in turn binds to or modulates ICOS.

In certain embodiments, the ICOS agonist exhibits one or more desirable functional properties, such as high affinity binding to ICOS, e.g., binding to human ICOS with a $K_D$ of $10^{-7}$ M, $10^{-8}$ M, $10^{-9}$ M, $10^{-10}$ M or less; lack of significant cross-reactivity to other immune-check point proteins, e.g., CD28 and CTLA-4; the ability to stimulate T cell proliferation; the ability to increase IL-10 secretion; and/or the ability to inhibit growth of tumor cells.

According to a specific embodiment, the ICOS agonist is the naturally occurring ligand (e.g. ICOSL) or a functional derivative or variant thereof which retain the ability to specifically bind to the ICOS. Thus, for example the ICOS agonist can be an entire ICOSL, soluble ICOSL or fragments thereof and fusion proteins comprising a functionally active portion of ICOSL covalently linked to a second protein domain, that binds to and activates ICOS, such as described in U.S. Application Publication Nos. 20040137577; 20020106730, the contents of which are hereby incorporated by reference in their entirety.

According to specific embodiments, the ICOS agonist is a tumor cell or membranes thereof expressing ICOSL that is used as an anti-tumor vaccine, such as disclosed e.g. in U.S. Pat. No. 8,709,417, which is hereby incorporated by reference in its entirety.

According to a specific embodiment, the ICOS agonist is an antibody.

According to specific embodiments, the ICOS agonist is an anti-ICOS antibody. Anti-ICOS antibodies suitable for use in the invention can be generated using methods well known in the art especially in light of the detailed description hereinabove. Alternatively, art recognized anti-ICOS antibodies can be used. Examples of anti-ICOS antibodies are disclosed for example in Hutloff, A. et al. (1999) Nature 397: 262-266, Deng et al. Hybrid Hybridomics. 2004 June; 23(3):176-82, Sakthivel et al. PLoS One. 2014 Jul. 16; 9(7):e100970, Redoglia et al. Eur J Immunol 1996 26: 2781-2789, U.S. Pat. Nos. 8,709,417; 6,803,039, International Application Publication Nos. WO2012131004; WO2014089113; WO2008137915, which are hereby incorporated by reference in their entirety.

Specific anti-ICOS antibodies that can be used according to some embodiments of the present invention include, but are not limited to an agonistic anti-ICOS antibody developed by Jounce Therapeutics.

According to a specific embodiment, the antibody competes with any of the above-mentioned antibodies for binding to ICOS.

According to a specific embodiment, the antibody competes for binding with and/or binds to the same epitope on ICOS as the above-mentioned antibodies.

According to another specific embodiment, the antibody has at least about 90% variable region amino acid sequence identity with the above-mentioned antibodies.

Other ICOS agonists that can be used according to specific embodiments of the present invention include nucleotides, expression vectors, peptides, fusion proteins and fragments targeting ICOS, functional ICOSL, are disclosed for examples in U.S. Application Publication Nos. 20140271677; 20040137577; 20020106730, International Application Publication No. WO2014089113, which are hereby incorporated by reference in their entirety.

The order in which the CXCR4 antagonistic peptide and the immune-check point regulator are administered to the subject can vary according to the method of treating.

Thus, according to a specific embodiment, step (a) is effected prior to step (b).

According to another specific embodiment, step (a) is effected following step (b).

According to yet another specific embodiment, step (a) is effected concomitantly with step (b).

Multiple rounds of administration according to the methods of the present invention and multiple doses of the CXCR4 antagonistic peptide and the immune-check point regulator can be administered. According to specific embodiments step (a) is effected multiple times. Thus, according to specific embodiments, administration of the immune-check point regulator is effected following at least one administration of the CXCR4 antagonistic peptide. According to specific embodiments step (B) is effected multiple times. Thus, according to specific embodiments, administering the CXCR4 antagonistic peptide of the present invention is effected following at least one administration of the immune-check point regulator. According to specific embodiments, administering the CXCR4 antagonistic peptide of the present invention is effected in a sequential order with administration of the immune-check point regulator.

According to specific embodiments, the CXCR4 antagonistic peptide can be administered to a subject in combination with several of the immune-check point regulators selected from the list of combinations described hereinabove.

According to specific embodiments, the CXCR4 antagonistic peptide and the immune-check point regulator of the invention can be administered to a subject in combination with other established or experimental therapeutic regimen to treat cancer including analgetics, chemotherapeutic agents, radiotherapeutic agents, hormonal therapy, immune modulators and other treatment regimens (e.g., surgery, cell transplantation e.g. hematopoietic stem cell transplantation) which are well known in the art.

According to some embodiments of the invention the method further comprises administering a vaccine and optionally wherein the vaccine is an HPV vaccine.

According to a specific embodiment, the vaccine is a human papiloma virus (HPV, e.g., HPV 16 vaccine) typically targeting E6 and/or E7. The vaccine may be a preventive vaccine or a therapeutic vaccine. Detailed examples of HPV vaccines which can be used along with the present teachings can be found in Lin et al. *J Formos Med Assoc.* 2010 January; 109(1): 4-24; and Rice et al. *Cancer Gene Therapy* 22, 454-462.

According to a specific embodiment, the preventive vaccines utilize the capsid proteins L1 and L2 as target antigens, inducing antibodies to neutralize and prevent entry of HPV into cells. Expression of recombinant L1, the major component of the capsid, in various cell types results in spontaneous assembly of virus-like particles (VLPs), which are immunologically and morphologically similar to HPV virions.

According to another specific embodiment, the vaccines is Gardasil™ or Cervarix™ Gardasil is a quadrivalent vaccine containing recombinant L1 VLPs for HPV genotypes 6, 11, 16 and 18 whereas the bivalent vaccine Cervarix contains L1 VLPs for HPV-16 and 18.

According to another specific embodiment, the vaccine is a monovalent HPV-16 L1 vaccine with an aluminium hydroxyphosphate sulfate adjuvant.

Exemplary, non-limiting, therapeutic vaccines comprise HPV E6 and E7 antigens. These represent ideal targets for therapeutic vaccines since these are constitutively expressed in HPV-infected cells and not healthy cells. E6 and E7 are essential to the induction and maintenance of cellular transformation, and thus are unlikely to be lost in an attempt to evade the immune system.

According to a specific embodiment, the therapeutic vaccines target E6 and/or E7.

Therapeutic vaccines typically include:

Live vector vaccines—Vector-based vaccines can deliver the antigens E6 and E7 to the dendritic cells (DCs), stimulating antigen expression through MHC class I (to CD8+ cytotoxic T cells) and MHC class II (to CD4+ helper T cells). Viral vectors used adenovirus, adeno-associated virus, vaccinia virus and alphaviruses, such as the Venezuelan equine encephalitis (VEE) virus;

Peptide/protein-based vaccines—Administered peptides and proteins derived from HPV antigens (e.g., E6 and/or E7) are taken up by DCs, processed and expressed via MHC II and/or I to the appropriate CD4+/CD8+ T cells;

Cell-based vaccines—dendritic cell-based or tumor cell based vaccines; and

Nucleic acid-based vaccines e.g., naked DNA based vaccines (e.g., ZYC-101 and ZYC-101a), naked RNA replicon vaccines.

The CXCR4 antagonistic peptides and/or the immune-check point regulators (e.g. PD1 antagonist, PDL-1 antagonist, CTLA-4 antagonist, LAG-3 antagonist, TIM-3 antagonist, KIR antagonist, IDO antagonist, OX40 agonist, CD137 agonist, CD27 agonist, CD40 agonist, GITR agonist, CD28 agonist and ICOS agonist) described hereinabove can be administered to the subject per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the CXCR4 antagonistic peptides and/or the immune-check point regulators accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, intradermal, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient.

The CXCR4 antagonistic peptide of the invention, the immune-check point regulator or the pharmaceutical composition comprising same can be administered in the same route or in separate routes.

According to a specific embodiment, the CXCR4 antagonistic peptide of the invention or the pharmaceutical composition comprising same is administered subcutaneously.

According to another specific embodiment, the CXCR4 antagonistic peptide of the invention or the pharmaceutical composition comprising same is administered intravenously.

According to a specific embodiment, the immune-check point regulator or the pharmaceutical composition comprising same is administered intravenously.

According to a specific embodiment, the immune-check point regulator or the pharmaceutical composition comprising same is administered via a subcutaneous route.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes.

Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Alternative embodiments include depots providing sustained release or prolonged duration of activity of the active ingredient in the subject, as are well known in the art.

Pharmaceutical compositions suitable for use in context of some embodiments of the invention include compositions wherein the active ingredients are contained in an amount effective to achieve the intended purpose. More specifically, according to specific embodiments, a therapeutically effective amount means an amount of active ingredients effective to prevent, alleviate or ameliorate symptoms of a disorder (e.g., cancer) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p.1).

Dosage amount and interval may be adjusted individually to provide levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

According to specific embodiments the CXCR4 antagonistic peptide of the invention or the pharmaceutical composition comprising same is administered in a dose ranging between 0.1 to 10 mg/kg of body weight, between 0.1 to 2 mg/kg of body weight, between 0.1 to 1 mg/kg of body weight, between 0.3 to 10 mg/kg of body weight, between 0.3 to 2 mg/kg of body weight, between 0.3 to 1 mg/kg of body weight or between 0.3 to 0.9 mg/kg of body weight.

According to a specific embodiment, the CXCR4 antagonistic peptide of the invention or the pharmaceutical composition comprising same is administered in a dose ranging between 0.5-2.0 mg/kg.

According to specific embodiments, the immune-check point regulator or the pharmaceutical composition comprising same is administered in a dose ranging between 0.001 to 30 mg/kg body weight, between 0.001 to 20 mg/kg body weight, between 0.001 to 10 mg/kg body weight, between 0.001 to 1 mg/kg body weight, between 0.01 to 30 mg/kg body weight, between 0.01 to 20 mg/kg body weight, between 0.01 to 10 mg/kg body weight, between 0.01 to 1 mg/kg body weight, between 0.1 to 30 mg/kg body weight, between 0.1 to 20 mg/kg body weight, between 0.1 to 10 mg/kg body weight, between 0.1 to 1 mg/kg body weight, between 1 to about 30 mg/kg, between 1 to about 20 mg/kg or between 1 to about 10 mg/kg.

The desired dose can be administered at one time or divided into sub-doses, e.g., 2-4 sub-doses and administered over a period of time, e.g., at appropriate intervals through the day or other appropriate schedule.

According to specific embodiments, the CXCR4 antagonistic peptide of the invention, the immune-check point regulator or the pharmaceutical composition comprising same is administered multiple times e.g. 2-10, over a period of time e.g. for several days to several weeks at appropriate intervals e.g. once a day, twice a week, once a week, once every two weeks, once a month, once every 3 to 6 months.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

According an aspect of the present invention there is provided an article of manufacture or a kit identified for use in treating cancer, comprising a packaging material packaging a peptide having an amino acid sequence as set forth in SEQ ID NO: 1 or an analog or derivative thereof and an immune-check point regulator (e.g. PD1 antagonist, PDL-1 antagonist, CTLA-4 antagonist, LAG-3 antagonist, TIM-3 antagonist, KIR antagonist, IDO antagonist, OX40 agonist, CD137 agonist, CD27 agonist, CD40 agonist, GITR agonist, CD28 agonist and ICOS agonist.

The peptide and the immune-check point regulator may be packaged in the same container or in separate containers; each possibility represents a separate embodiment of the present invention.

According to specific embodiments, the peptide and the immune-check point regulator are in separate formulations.

According to other specific embodiments, the peptide and the immune-check point regulator are in a co-formulation.

It is expected that during the life of a patent maturing from this application many relevant immune-check point regulators will be developed and the scope of the term "immune-check point regulator" is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5 and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Use of BL-8040 for Treating Cancer

BL-8040 is safe and well tolerated drug that was shown to induce rapid mobilization of hematopoietic stem/progenitor cells and mesenchymal stem cells as well as T cells, B cells, NK cells, NKT cells and ImDC to the peripheral blood. Therefore, BL-8040 can be used to induce the mobilization and dissemination of immature DC, NK cells, B cells, monocytes/macrophages and T effector and memory cells into tumors.

Experimental Procedures

According to one protocol, BL-8040 is injected into a cancer patient at a dose of 0.5-2.0 mg/kg for 3-10 days and then 1-3 times a week in combination with immunomodulatory antibodies that antagonize with an inhibitory check point molecule such as anti-CTLA4 (such as produced by MedImmune or BMS), anti-PD-1 (such as produced by BMY, AZY, Merck or Curetech), anti-PDL-1 (such as produced by Roche, Merck Serono, AZY or BMS), anti-LAG-3 (such as produced by BMS or Immutep), and anti-KIR (such as produced by BMY or Innate Pharma).

According to another protocol, BL-8040 is injected into a cancer patient at a dose of 0.5-2.0 mg/kg for 3-10 days and then 1-3 times a week in combination with a fusion protein targeting an inhibitory check point molecule such as PD1 (such as produced by AZY).

According to another protocol BL-8040 is injected into a cancer patient at a dose of 0.5-2.0 mg/kg for 3-10 days and then 1-3 times a week in combination with a small molecule that antagonizes with an inhibitory check point molecule such as IDO [such as NLG919 (produced by Roche), F001287 (produced by BMY), Indoximod (produced by NewLink Genetics), NLG-919 (produced by NewLink Genetics) and INCB-024360 (produced by Incyte)].

According to another protocol BL-8040 is injected into a cancer patient at a dose of 0.5-2.0 mg/kg for 3-10 days and then 1-3 times a week in combination with immunomodulatory antibodies that activates a co-stimulatory check point molecule such as CD40 (such as produced by Pfizer or Seattle Genetics Inc.), 4-1BB (such as produced by BMY or Merck Serono), GITR (such as produced by Merck or GITR Inc.), OX40 (such as produced by AZY or Roche), and CD27 (such as produced by Celldex).

According to another protocol, BL-8040 is injected into a cancer patient at a dose of 0.5-2.0 mg/kg for 3-10 days and then 1-3 times a week in combination with a fusion protein targeting a co-stimulatory check point molecule such as OX-40 (such as produced by AZY).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of treating cancer in a human subject in need thereof, the method comprising:
   (a) administering to the human subject a therapeutically effective amount of a peptide having an amino acid sequence as set forth in SEQ ID NO: 1;
   (b) administering to the human subject a therapeutically effective amount of a PD1 antagonist; and
   (c) administering to the human subject a therapeutically effective amount of a chemotherapeutic agent,
   thereby treating the cancer in the human subject.

2. The method of claim 1, wherein said cancer is pancreatic cancer.

3. The method of claim 1, wherein said PD1 antagonist is an anti-PD1 antibody.

4. The method of claim 1, wherein said cancer is pancreatic cancer, wherein said PD1 antagonist is an anti-PD1 antibody and wherein said peptide is as set forth in SEQ ID NO: 1.

* * * * *